(12) United States Patent
Asconeguy et al.

(10) Patent No.: US 12,402,901 B2
(45) Date of Patent: Sep. 2, 2025

(54) INTRAVASCULAR LITHOTRIPSY CATHETER

(71) Applicant: IV-X Medical, LLC, Menlo Park, CA (US)

(72) Inventors: Alexander Joseph Asconeguy, Eagle, ID (US); Ricardo David Roman, Chula Vista, CA (US); Michael Christopher Oliveira, Escondido, CA (US); Josef V. Koblish, Sunnyvale, CA (US); Jeremy Durack, New York, NY (US)

(73) Assignee: IV-X Medical, LLC, Menlo Park, CA (US)

( * ) Notice: Subject to any disclaimer, the term of this patent is extended or adjusted under 35 U.S.C. 154(b) by 0 days.

(21) Appl. No.: 19/047,456

(22) Filed: Feb. 6, 2025

(65) Prior Publication Data

US 2025/0255628 A1 Aug. 14, 2025

Related U.S. Application Data

(60) Provisional application No. 63/718,155, filed on Nov. 8, 2024, provisional application No. 63/647,485, filed
(Continued)

(51) Int. Cl.
*A61B 17/22* (2006.01)
*A61B 17/00* (2006.01)

(52) U.S. Cl.
CPC ............ *A61B 17/2202* (2013.01); *A61B 2017/00893* (2013.01); *A61B 2017/22021* (2013.01);
(Continued)

(58) Field of Classification Search
CPC .......... A61B 17/2202; A61B 17/22022; A61B 2017/22021; A61B 2017/22025
See application file for complete search history.

(56) References Cited

U.S. PATENT DOCUMENTS

| 4,445,509 A | 5/1984 | Auth |
| 4,990,134 A | 2/1991 | Auth |

(Continued)

FOREIGN PATENT DOCUMENTS

| CN | 104582621 | 4/2017 |
| CN | 104619272 | 1/2018 |

(Continued)

OTHER PUBLICATIONS

Extended European Search Report for EP Application No. 22169681.8 dated Jul. 22, 2022; 5 pages.
(Continued)

*Primary Examiner* — Brigid K Byrd
(74) *Attorney, Agent, or Firm* — Knobbe, Martens, Olson & Bear, LLP

(57) ABSTRACT

An intravascular lithotripsy catheter can include a sheath, first and second insulated wires, and a carrier. The first and second insulated wires can include exposed portions of an electrically conductive member and can be wound around the sheath. Exposed portions of the first and second insulated wires that form an emitter can be circumferentially offset from each other and can be longitudinally offset from each other. The carrier can encase the first and second insulated wires and the sheath and can comprise a plurality of carrier openings aligned with the exposed portions of the first and second insulated wires. The catheter can electrically connect to an energy generator that is operable to cause a spark to travel longitudinally along the catheter and circumferentially around the catheter between the exposed portions.

20 Claims, 44 Drawing Sheets

Related U.S. Application Data on May 14, 2024, provisional application No. 63/551,482, filed on Feb. 8, 2024.

(52) U.S. Cl.
CPC ............ *A61B 2017/22025* (2013.01); *A61B 2017/22062* (2013.01); *A61B 2017/22082* (2013.01)

(56) References Cited

U.S. PATENT DOCUMENTS

| | | |
|---|---|---|
| 5,116,227 A | 5/1992 | Levy |
| 5,152,768 A | 10/1992 | Bhatta |
| 5,368,591 A | 11/1994 | Lennox et al. |
| 5,454,809 A | 10/1995 | Janssen |
| 5,498,238 A | 3/1996 | Shapland et al. |
| 5,584,843 A | 12/1996 | Wulfman et al. |
| 5,891,089 A | 4/1999 | Katz et al. |
| 6,132,444 A | 10/2000 | Shturman et al. |
| 6,364,894 B1 | 4/2002 | Healy et al. |
| 6,456,888 B1 | 9/2002 | Skinner et al. |
| 6,494,890 B1 | 12/2002 | Shturman et al. |
| 6,652,547 B2 | 11/2003 | Rabiner et al. |
| 6,755,821 B1 | 6/2004 | Fry |
| 7,244,225 B2 | 7/2007 | Loeb et al. |
| 7,309,324 B2 | 12/2007 | Hayes et al. |
| 7,569,032 B2 | 8/2009 | Naimark et al. |
| 7,850,685 B2 | 12/2010 | Kunis et al. |
| 8,177,801 B2 | 5/2012 | Kallok et al. |
| 8,353,923 B2 | 1/2013 | Shturman |
| 8,600,499 B2 | 12/2013 | Shuros et al. |
| 8,709,075 B2 | 4/2014 | Adams et al. |
| 8,728,091 B2 | 5/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,072,534 B2 | 7/2015 | Adams et al. |
| 9,138,249 B2 | 9/2015 | Adams et al. |
| 9,180,280 B2 | 11/2015 | Hawkins et al. |
| 9,220,521 B2 | 12/2015 | Hawkins et al. |
| 9,289,173 B2 | 3/2016 | Splinter |
| 9,333,000 B2 | 5/2016 | Hakala et al. |
| 9,421,025 B2 | 8/2016 | Hawkins et al. |
| 9,474,676 B2 | 10/2016 | Bonuttti |
| 9,522,012 B2 | 12/2016 | Adams |
| 9,642,673 B2 | 5/2017 | Adams et al. |
| 9,713,730 B2 | 7/2017 | Mathur et al. |
| 9,717,513 B2 | 8/2017 | Golan |
| 9,814,476 B2 | 11/2017 | Adams et al. |
| 9,826,996 B2 | 11/2017 | Meinke et al. |
| 9,867,629 B2 | 1/2018 | Hawkins |
| 9,993,292 B2 | 6/2018 | Adams et al. |
| 10,010,666 B2 | 7/2018 | Rubinsky et al. |
| 10,039,561 B2 | 8/2018 | Adams et al. |
| 10,058,340 B2 | 8/2018 | Cioanta et al. |
| 10,076,384 B2 | 9/2018 | Kasprzyk et al. |
| 10,149,690 B2 | 12/2018 | Hawkins et al. |
| 10,159,505 B2 | 12/2018 | Hakala et al. |
| 10,182,838 B2 | 1/2019 | Shimokawa et al. |
| 10,201,387 B2 | 2/2019 | Grace et al. |
| 10,226,265 B2 | 3/2019 | Ku et al. |
| 10,299,820 B2 | 5/2019 | Kohler et al. |
| 10,357,264 B2 | 7/2019 | Kat-Kuoy |
| 10,383,683 B2 | 8/2019 | Ogata et al. |
| 10,420,569 B2 | 9/2019 | Adams |
| 10,426,835 B2 | 10/2019 | Morganstern et al. |
| 10,441,300 B2 | 10/2019 | Hawkins |
| 10,478,214 B2 | 11/2019 | Eaton |
| 10,517,620 B2 | 12/2019 | Adams |
| 10,517,621 B1 | 12/2019 | Hakala et al. |
| 10,561,428 B2 | 2/2020 | Eggert et al. |
| 10,646,240 B2 | 5/2020 | Betelia et al. |
| 10,668,208 B2 | 6/2020 | Rubinsky et al. |
| 10,682,178 B2 | 6/2020 | Adams et al. |
| 10,702,293 B2 | 7/2020 | Adams et al. |
| 10,736,603 B2 | 8/2020 | Messas et al. |
| 10,758,255 B2 | 9/2020 | Adams |
| 10,765,440 B2 | 9/2020 | Tozzi |
| 10,786,267 B2 | 9/2020 | Wasdyke et al. |
| 10,786,661 B2 | 9/2020 | Grace |
| 10,850,078 B2 | 12/2020 | Grace et al. |
| 10,856,893 B2 | 12/2020 | Eggert et al. |
| 10,888,715 B2 | 1/2021 | Cioanta et al. |
| 10,898,213 B2 | 1/2021 | Grace et al. |
| 10,898,214 B2 | 1/2021 | Schoenle |
| 10,959,743 B2 | 3/2021 | Adams et al. |
| 10,966,737 B2 | 4/2021 | Nguyen |
| 10,973,538 B2 | 4/2021 | Hakala et al. |
| 10,973,570 B2 | 4/2021 | Mathur et al. |
| 11,006,996 B2 | 5/2021 | Walzman |
| 11,020,135 B1 | 6/2021 | Hawkins |
| 11,026,707 B2 | 6/2021 | Ku et al. |
| 11,065,645 B2 | 7/2021 | Brouillette et al. |
| 11,076,874 B2 | 8/2021 | Hakala et al. |
| 11,179,169 B2 | 11/2021 | Brouillette et al. |
| 11,246,659 B2 | 2/2022 | Grace et al. |
| 11,266,425 B2 | 3/2022 | McCaffrey et al. |
| 11,278,300 B2 | 3/2022 | Bahmanyar et al. |
| 11,337,713 B2 | 5/2022 | Nguyen et al. |
| 11,364,042 B2 | 6/2022 | Maxwell et al. |
| 11,419,619 B2 | 8/2022 | Brouillette et al. |
| 11,432,834 B2 | 9/2022 | Adams |
| 11,484,327 B2 | 11/2022 | Anderson et al. |
| 11,517,337 B2 | 12/2022 | Betelia et al. |
| 11,517,338 B2 | 12/2022 | Hawkins |
| 11,534,187 B2 | 12/2022 | Bonutti |
| 11,596,424 B2 | 3/2023 | Hakala et al. |
| 11,602,363 B2 | 3/2023 | Nguyen |
| 11,622,780 B2 | 4/2023 | Nguyen et al. |
| 11,633,200 B2 | 4/2023 | Anderson et al. |
| 11,771,449 B2 | 10/2023 | Adams et al. |
| 11,779,363 B2 | 10/2023 | Vo |
| 2002/0082553 A1 | 6/2002 | Duchamp |
| 2003/0176873 A1 | 9/2003 | Chernenko et al. |
| 2005/0194583 A1 | 9/2005 | Taylor et al. |
| 2005/0251131 A1 | 11/2005 | Lesh |
| 2006/0106449 A1 | 5/2006 | Ben Muhvar |
| 2006/0106450 A1 | 5/2006 | Ben Muhvar |
| 2006/0190022 A1 | 8/2006 | Beyar et al. |
| 2006/0221528 A1 | 10/2006 | Li et al. |
| 2007/0005053 A1 | 1/2007 | Dando |
| 2007/0239082 A1 | 10/2007 | Schultheiss et al. |
| 2007/0239182 A1 | 10/2007 | Glines et al. |
| 2008/0039904 A1 | 2/2008 | Bulkes et al. |
| 2008/0065009 A1 | 3/2008 | Ben-Muvhar |
| 2008/0249595 A1 | 10/2008 | McDaniel |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0137754 A1 | 6/2010 | Zhou |
| 2010/0160903 A1 | 6/2010 | Krespi |
| 2010/0229792 A1 | 9/2010 | Yamasaki et al. |
| 2011/0196412 A1 | 8/2011 | Levit et al. |
| 2011/0245841 A1 | 10/2011 | Shohat et al. |
| 2012/0116289 A1 | 5/2012 | Hawkins et al. |
| 2012/0203255 A1 | 8/2012 | Hawkins et al. |
| 2012/0221013 A1 | 8/2012 | Hawkins et al. |
| 2012/0277698 A1 | 11/2012 | Andrew et al. |
| 2013/0030431 A1 | 1/2013 | Adams |
| 2013/0041355 A1 | 2/2013 | Heeren et al. |
| 2014/0005576 A1* | 1/2014 | Adams ................. A61B 18/00 601/4 |
| 2014/0039513 A1 | 2/2014 | Hakala et al. |
| 2014/0039514 A1 | 2/2014 | Adams et al. |
| 2014/0046229 A1 | 2/2014 | Hawkins et al. |
| 2014/0046353 A1 | 2/2014 | Adams |
| 2014/0052145 A1 | 2/2014 | Adams et al. |
| 2014/0052147 A1 | 2/2014 | Hakala et al. |
| 2014/0074111 A1 | 3/2014 | Hakala et al. |
| 2014/0074113 A1 | 3/2014 | Hakala et al. |

(56) References Cited

U.S. PATENT DOCUMENTS

| | | |
|---|---|---|
| 2014/0163592 A1 | 6/2014 | Hawkins et al. |
| 2014/0214061 A1 | 7/2014 | Adams et al. |
| 2014/0243820 A1 | 8/2014 | Adams et al. |
| 2014/0243847 A1 | 8/2014 | Hakala et al. |
| 2014/0288570 A1 | 9/2014 | Adams |
| 2015/0039002 A1 | 2/2015 | Hawkins |
| 2015/0073430 A1 | 3/2015 | Hakala et al. |
| 2015/0080995 A1 | 3/2015 | Seeley et al. |
| 2015/0238208 A1 | 8/2015 | Adams et al. |
| 2015/0238209 A1 | 8/2015 | Hawkins et al. |
| 2015/0320432 A1 | 11/2015 | Adams |
| 2016/0101280 A1 | 4/2016 | Thakkar et al. |
| 2016/0135828 A1 | 5/2016 | Hawkins et al. |
| 2016/0151081 A1 | 6/2016 | Adams et al. |
| 2016/0183957 A1 | 6/2016 | Hakala et al. |
| 2016/0235463 A1 | 8/2016 | Ogata et al. |
| 2016/0324534 A1 | 11/2016 | Hawkins et al. |
| 2016/0331389 A1 | 11/2016 | Hakala et al. |
| 2016/0354144 A1 | 12/2016 | Caplan et al. |
| 2017/0056035 A1 | 3/2017 | Adams |
| 2017/0086867 A1 | 3/2017 | Adams |
| 2017/0135709 A1* | 5/2017 | Nguyen ............ A61B 17/22004 |
| 2017/0258523 A1 | 9/2017 | Adams et al. |
| 2017/0303946 A1* | 10/2017 | Ku .................. A61B 17/22029 |
| 2017/0311965 A1 | 11/2017 | Adams |
| 2018/0021084 A1 | 1/2018 | Onik et al. |
| 2018/0028208 A1 | 2/2018 | Adams et al. |
| 2018/0078243 A1* | 3/2018 | Rocha-Singh ..... A61B 17/1635 |
| 2018/0098779 A1* | 4/2018 | Betelia ............ A61B 17/22022 |
| 2018/0153568 A1 | 6/2018 | Kat-Kuoy |
| 2018/0256250 A1 | 9/2018 | Adams et al. |
| 2018/0303501 A1 | 10/2018 | Hawkins |
| 2018/0304053 A1 | 10/2018 | Eggert et al. |
| 2018/0317946 A1 | 11/2018 | Adams et al. |
| 2018/0360482 A1 | 12/2018 | Nguyen |
| 2019/0069916 A1 | 3/2019 | Hawkins et al. |
| 2019/0125932 A1 | 5/2019 | Leonhardt et al. |
| 2019/0150960 A1 | 5/2019 | Nguyen et al. |
| 2019/0175198 A1 | 6/2019 | Ku et al. |
| 2019/0254692 A1 | 8/2019 | Hakala et al. |
| 2019/0269426 A1 | 9/2019 | Hakala et al. |
| 2019/0365400 A1 | 12/2019 | Adams et al. |
| 2019/0388110 A1 | 12/2019 | Nguyen et al. |
| 2020/0000484 A1 | 1/2020 | Hawkins |
| 2020/0022716 A1 | 1/2020 | Hakala et al. |
| 2020/0085458 A1 | 3/2020 | Nguyen et al. |
| 2020/0085459 A1 | 3/2020 | Adams |
| 2020/0129231 A1* | 4/2020 | McCaffrey ....... A61B 17/22004 |
| 2020/0129742 A1 | 4/2020 | Cope et al. |
| 2020/0229831 A1 | 7/2020 | Leonhardt et al. |
| 2020/0246032 A1 | 8/2020 | Betelia et al. |
| 2020/0297366 A1 | 9/2020 | Nguyen et al. |
| 2020/0383724 A1 | 12/2020 | Adams et al. |
| 2020/0406010 A1 | 12/2020 | Massimini et al. |
| 2021/0008263 A1 | 1/2021 | Leonhardt |
| 2021/0008354 A1 | 1/2021 | Bhamanyar |
| 2021/0038237 A1 | 2/2021 | Adams |
| 2021/0085347 A1 | 3/2021 | Phan et al. |
| 2021/0085348 A1 | 3/2021 | Nguyen |
| 2021/0085349 A1 | 3/2021 | Cioanta et al. |
| 2021/0085353 A1 | 3/2021 | Kovac et al. |
| 2021/0085383 A1 | 3/2021 | Vo et al. |
| 2021/0113224 A1 | 4/2021 | Dinh |
| 2021/0145447 A1 | 5/2021 | Stefanov |
| 2021/0153883 A1 | 5/2021 | Casey et al. |
| 2021/0153885 A1 | 5/2021 | Spector et al. |
| 2021/0177445 A1 | 6/2021 | Nguyen |
| 2021/0186540 A1 | 6/2021 | Taff et al. |
| 2021/0186613 A1 | 6/2021 | Cook et al. |
| 2021/0220528 A1 | 7/2021 | Jalgaonkar et al. |
| 2021/0228222 A1 | 7/2021 | Porter |
| 2021/0236190 A1 | 8/2021 | Taff et al. |
| 2021/0251648 A1 | 8/2021 | Kugler et al. |
| 2021/0259860 A1 | 8/2021 | Walzman |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290305 A1 | 9/2021 | Cook et al. |
| 2021/0307828 A1 | 10/2021 | Schultheis et al. |
| 2021/0315639 A1 | 10/2021 | Manucherhabadi et al. |
| 2021/0330384 A1 | 10/2021 | Cook et al. |
| 2021/0338258 A1 | 11/2021 | Hawkins et al. |
| 2021/0338329 A1 | 11/2021 | Narula et al. |
| 2021/0346040 A1 | 11/2021 | Panian |
| 2021/0353314 A1 | 11/2021 | Porter |
| 2021/0353359 A1 | 11/2021 | Cook et al. |
| 2021/0369348 A1 | 12/2021 | Cook et al. |
| 2021/0378743 A1 | 12/2021 | Massimini et al. |
| 2021/0378744 A1 | 12/2021 | Fanier et al. |
| 2021/0379354 A1 | 12/2021 | Tansley et al. |
| 2021/0386439 A1 | 12/2021 | Spence |
| 2021/0386440 A1 | 12/2021 | Ogle |
| 2021/0386479 A1 | 12/2021 | Massimini et al. |
| 2021/0393276 A1 | 12/2021 | Whelan |
| 2022/0008130 A1 | 1/2022 | Massimini et al. |
| 2022/0015785 A1 | 1/2022 | Hakala et al. |
| 2022/0031287 A1 | 2/2022 | Ebbini et al. |
| 2022/0054150 A1 | 2/2022 | Dholakia et al. |
| 2022/0054194 A1 | 2/2022 | Bacher et al. |
| 2022/0062588 A1 | 3/2022 | Mintz |
| 2022/0111183 A1 | 4/2022 | Gray |
| 2022/0117719 A1 | 4/2022 | Leonhardt |
| 2022/0125450 A1 | 4/2022 | Sirhan et al. |
| 2022/0151646 A1 | 5/2022 | Dholakia et al. |
| 2022/0151647 A1 | 5/2022 | Dolendo et al. |
| 2022/0152355 A1 | 5/2022 | Dolendo et al. |
| 2022/0152364 A1 | 5/2022 | Cope et al. |
| 2022/0160942 A1 | 5/2022 | Skujins et al. |
| 2022/0175404 A1 | 6/2022 | Mintz et al. |
| 2022/0175450 A1 | 6/2022 | Laudenslager et al. |
| 2022/0183708 A1 | 6/2022 | Phan et al. |
| 2022/0183756 A1 | 6/2022 | Milner et al. |
| 2022/0192737 A1 | 6/2022 | Altmann et al. |
| 2022/0192739 A1 | 6/2022 | Deen et al. |
| 2022/0192741 A1 | 6/2022 | Reinders et al. |
| 2022/0202431 A1 | 6/2022 | Davidson et al. |
| 2022/0211983 A1 | 7/2022 | Giasolli et al. |
| 2022/0218372 A1 | 7/2022 | Nguyen et al. |
| 2022/0218562 A1 | 7/2022 | Capelli et al. |
| 2022/0226114 A1 | 7/2022 | Hou et al. |
| 2022/0257268 A1 | 8/2022 | Culbert et al. |
| 2022/0280171 A1 | 9/2022 | Teigen et al. |
| 2022/0280172 A1 | 9/2022 | Girdhar et al. |
| 2022/0280237 A1 | 9/2022 | Efremkin |
| 2022/0280244 A1 | 9/2022 | Zheng et al. |
| 2022/0280765 A1 | 9/2022 | Tabiliran et al. |
| 2022/0287730 A1 | 9/2022 | Chisena et al. |
| 2022/0287731 A1 | 9/2022 | Tan et al. |
| 2022/0287732 A1* | 9/2022 | Anderson ............ A61M 25/104 |
| 2022/0296261 A1 | 9/2022 | Panian |
| 2022/0313359 A1 | 10/2022 | Schultheis et al. |
| 2022/0323087 A1 | 10/2022 | Konstantino et al. |
| 2022/0338889 A1 | 10/2022 | Sirhan et al. |
| 2022/0338890 A1 | 10/2022 | Anderson et al. |
| 2022/0339339 A1 | 10/2022 | Nair et al. |
| 2022/0354528 A1 | 11/2022 | Jalgaonkar et al. |
| 2022/0354578 A1 | 11/2022 | Cook et al. |
| 2022/0361901 A1 | 11/2022 | De Leon et al. |
| 2023/0037716 A1 | 2/2023 | Batchelder et al. |
| 2023/0038308 A1 | 2/2023 | Batchelder et al. |
| 2023/0038388 A1 | 2/2023 | Batchelder et al. |
| 2023/0038663 A1 | 2/2023 | Batchelder et al. |
| 2023/0040190 A1 | 2/2023 | Batchelder et al. |
| 2023/0040420 A1 | 2/2023 | Batchelder et al. |
| 2023/0043475 A1 | 2/2023 | Adams |
| 2023/0044926 A1 | 2/2023 | Batchelder et al. |
| 2023/0107690 A1 | 4/2023 | Nguyen |
| 2023/0123003 A1* | 4/2023 | Vo .................... A61B 17/22022 606/128 |
| 2023/0165598 A1 | 6/2023 | Nguyen et al. |
| 2023/0190316 A1 | 6/2023 | Nguyen |
| 2023/0404605 A1 | 12/2023 | Vo |

(56) References Cited

U.S. PATENT DOCUMENTS

2023/0405268 A1* 12/2023 Beach .............. A61B 17/22022
2024/0058586 A1  2/2024 Wilson et al.

FOREIGN PATENT DOCUMENTS

| | | |
|---|---|---|
| CN | 110811761 | 2/2020 |
| CN | 111067591 | 4/2020 |
| CN | 111184553 | 5/2020 |
| CN | 109788965 | 7/2022 |
| CN | 115153753 | 10/2022 |
| CN | 115252050 | 11/2022 |
| CN | 115445057 | 12/2022 |
| CN | 218510479 | 2/2023 |
| CN | 115779286 | 3/2023 |
| CN | 218552622 | 3/2023 |
| CN | 218979060 | 5/2023 |
| CN | 218979061 | 5/2023 |
| CN | 218979088 | 5/2023 |
| CN | 218979918 | 5/2023 |
| CN | 116456916 | 7/2023 |
| CN | 118055734 | 5/2024 |
| DE | 30 38 445 | 6/1990 |
| EP | 0 571 306 | 11/1993 |
| EP | 3 809 988 | 6/2023 |
| EP | 4 034 004 | 12/2023 |
| ES | 2 914 851 | 6/2022 |
| JP | 62-275446 | 11/1987 |
| JP | 2016-195821 | 11/2016 |
| JP | 2022-190013 | 12/2022 |
| WO | WO 2015/167360 | 11/2015 |
| WO | WO 2019/174625 | 9/2019 |
| WO | WO 2021/025624 | 2/2021 |
| WO | WO 2021/225743 | 11/2021 |
| WO | WO 2022/125807 | 6/2022 |
| WO | WO 2022/182640 | 9/2022 |
| WO | WO 2022/182645 | 9/2022 |
| WO | WO 2023/284213 | 1/2023 |
| WO | WO 2023/015047 | 2/2023 |
| WO | WO 2023/059967 | 4/2023 |

OTHER PUBLICATIONS

International Search Report for International Application No. PCT/US22/71341, dated Aug. 11, 2022; 4 pages.

Touya et al., "Development of subsonic electrical discharges in water and measurements of the associated pressure waves," J. Phys. D: Appl. Phys. 39 (2006) 5236-5244; 10 pages.

International Search report and Written Opinion for International application No. PCT/US2025/014851, dated Apr. 9, 2025; in 17 pages.

* cited by examiner

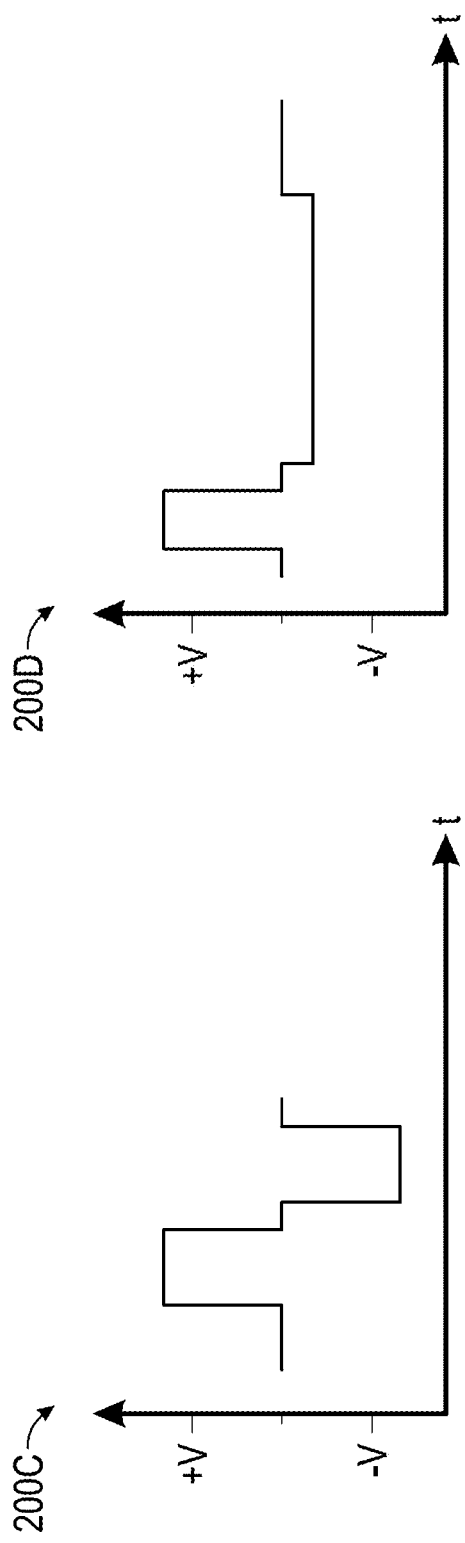
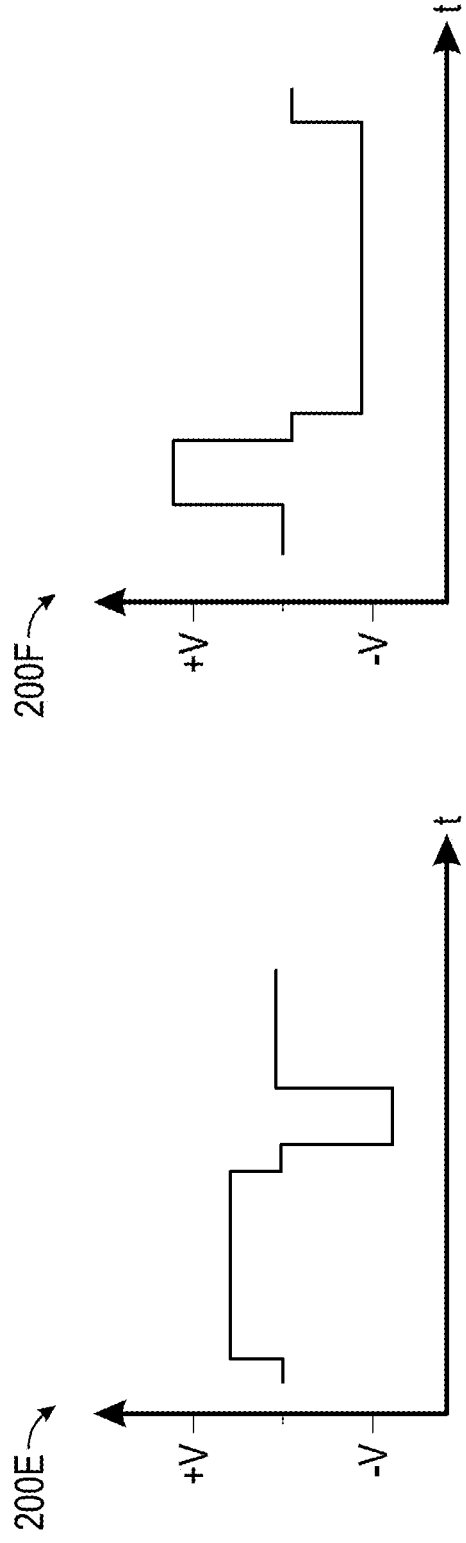
FIG. 2C
FIG. 2D
FIG. 2E
FIG. 2F

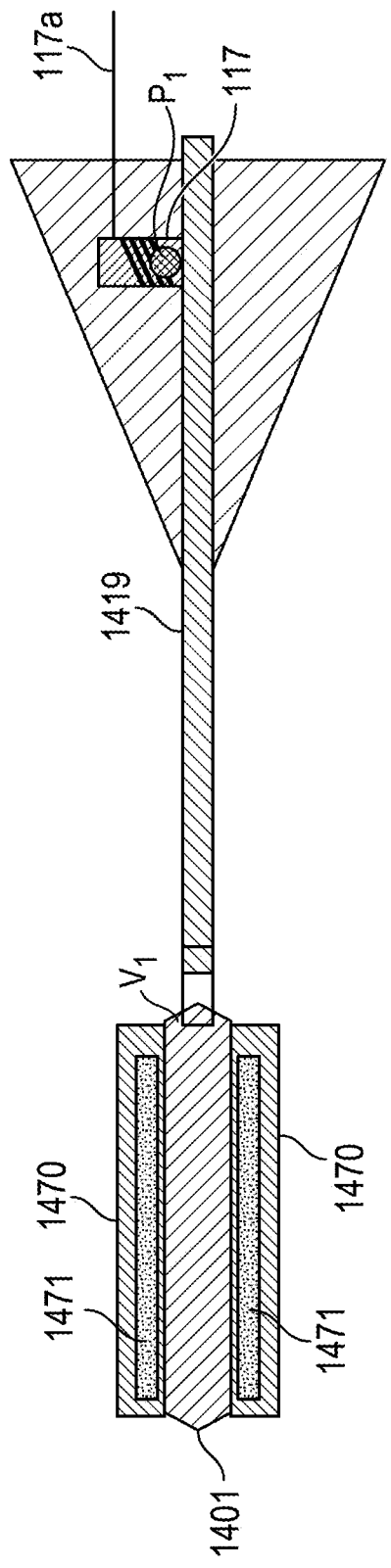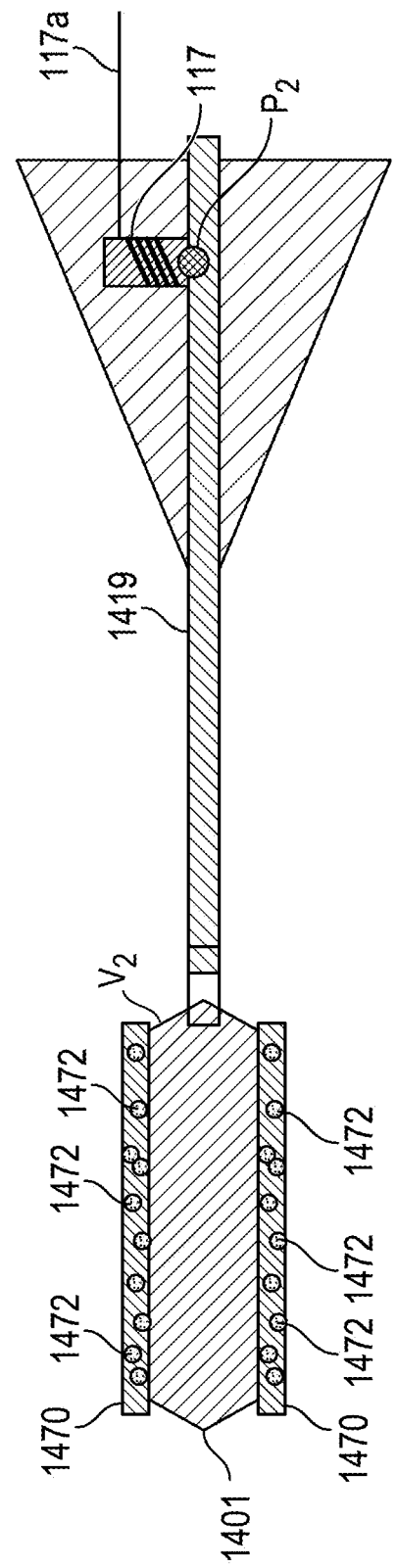
FIG. 14A
FIG. 14B

FIG. 18B

INTRAVASCULAR LITHOTRIPSY CATHETER

CROSS REFERENCE TO RELATED APPLICATIONS

Any and all applications for which a foreign or domestic priority claim is identified in the Application Data Sheet as filed with the present application are hereby incorporated by reference under 37 CFR 1.57 for all purposes and for all that they contain.

TECHNICAL FIELD

The present disclosure relates generally to intravascular lithotripsy catheters. More specifically, the present disclosure relates to multiple intravascular lithotripsy catheter implementations and associated systems that can selectively control the firing of one or more emitters.

BACKGROUND

An intravascular lithotripsy (IVL) catheter may be used to treat calcified lesions within the cardiovascular system. IVL catheters can be used to enhance the effectiveness of percutaneous cardiovascular interventions in cases where heavily calcified lesions present challenges for traditional treatment methods. An IVL catheter can include a balloon, which when inflated with a saline solution, can deliver mechanical pressure waves to break up and/or modify calcified lesions, making it easier to dilate an artery during balloon angioplasty and/or stent placement procedures.

SUMMARY

The systems, methods, and devices described herein each have several aspects, no single one of which is solely responsible for its desirable attributes. Without limiting the scope of this disclosure, several non-limiting features will now be discussed briefly.

Described herein are an improved IVL catheter implementations and systems that can safely deliver one or more sonic pressure waves (hereinafter "sonic waves") within blood vessels of a cardiovascular system.

Disclosed herein is an intravascular lithotripsy system configured to modify calcified plaque within a blood vessel of a subject. The system can comprise: a sheath comprising a lumen configured to receive a guidewire; at least three insulated wires; and an energy generator. Each of the at least three insulated wires can comprise at least two exposed portions spaced from one another along a length of the insulated wire, wherein the at least three insulated wires are helically wound around an outer surface of the sheath and independently electrically connected with the energy generator, the exposed portions of the at least three insulated wires defining a plurality of emitters spaced from one another along a length of the sheath and independently operable by the energy generator. The energy generator can induce a spark via each of the plurality of emitters.

In some implementations, the plurality of emitters comprises: a first emitter defined by a first exposed portion of a first one of the at least three insulated wires and a first exposed portion of a second one of the at least three insulated wires; a second emitter defined by a second exposed portion of the first one of the at least three insulated wires and a first exposed portion of a third one of the at least three insulated wires; and a third emitter defined by a second exposed portion of the second one of the at least three insulated wires and a second exposed portion of the third one of the at least three insulated wires.

In some implementations, each of the at least three insulated wires is configured to form at least one of the plurality of emitters with each of the other at least three insulated wires.

In some implementations, the plurality of emitters are formed from the at least three insulated wires without any other insulated wires.

In some implementations, the at least three insulated wires comprises at least four insulated wires, wherein the plurality of emitters comprises more emitters than the at least four insulated wires.

In some implementations, the at least three insulated wires does not include a dedicated return wire.

In some implementations, the energy generator is configured to drive voltage on the at least three insulated wires independently to cause each of the at least three insulated wires to transition between operating at least as a live wire conducting current from the energy generator or as a return wire conducting current to the energy generator.

In some implementations, the system comprises a balloon around at least a portion of the sheath and configured to be expanded with a conductive fluid configured to conduct a sonic wave originating from a spark.

In some implementations, the system comprises a carrier encasing the at least three insulated wires and the sheath, the carrier comprising carrier openings aligned with the exposed portions of the at least three insulated wires.

Disclosed herein is an intravascular lithotripsy catheter for modifying calcified plaque within a blood vessel of a subject. The intravascular lithotripsy catheter can comprise a sheath, a first insulated wire, a second insulated wire, and a carrier. The sheath can comprise a lumen configured to receive a guidewire, wherein a longitudinal axis of the intravascular lithotripsy catheter extends through the lumen. The first insulated wire can be wound around and can contact an outer surface of the sheath. The first insulated wire can comprise an electrically conductive member, an insulative member encasing the electrically conductive member, and an insulative member opening forming an exposed portion of the electrically conductive member. The second insulated wire can be wound around and can contact the outer surface of the sheath. The second insulated wire can be arranged adjacent the first insulated wire and can comprise an electrically conductive member, an insulative member encasing the electrically conductive member of the second insulated wire, and an insulative member opening forming an exposed portion of the electrically conductive member of the second insulated wire. The exposed portion of the second insulated wire can be circumferentially offset from the exposed portion of the first insulated wire by an angle originating at the longitudinal axis. The exposed portion of the second insulated wire can be longitudinally offset from the exposed portion of the first insulated wire by a longitudinal distance extending along the intravascular lithotripsy catheter parallel to the longitudinal axis. The carrier can encase the first and second insulated wires and the sheath. The carrier can comprise: a first carrier opening aligned with the exposed portion of the electrically conductive member of the first insulated wire; and a second carrier opening spaced from the first carrier opening and aligned with the exposed portion of the electrically conductive member of the second insulated wire. The intravascular lithotripsy catheter can be configured to be electrically connect to an energy generator that is operable to cause a spark to travel longitudinally along the intravascular lithotripsy catheter and circumferentially around the intravascular lithotripsy catheter between the exposed portions of the first and second insulated wires.

In some implementations, the carrier comprises an inner surface configured to contact the first and second insulated wires and an outer surface opposite the inner surface, wherein the intravascular lithotripsy catheter is configured such that the spark travels from the exposed portion of the first insulated wire, through the first carrier opening, above the outer surface of the carrier, through the second carrier opening, and to the exposed portion of the second insulated wire.

Disclosed herein is an intravascular lithotripsy catheter for modifying calcified plaque within a blood vessel of a subject. The intravascular lithotripsy catheter can comprise a sheath configured to receive a guidewire through a lumen of the sheath, a longitudinal axis extending through the lumen of the sheath, a first insulated wire, a second insulated wire, and a carrier. The first insulated wire can comprise an electrically conductive member, an insulative member encasing the electrically conductive member, and an insulative member opening forming an exposed portion of the electrically conductive member. The second insulated wire can be arranged adjacent the first insulated wire and can comprise an electrically conductive member, an insulative member encasing the electrically conductive member of the second insulated wire, and an insulative member opening forming an exposed portion of the electrically conductive member of the second insulated wire. The first and second insulated wires can be wrapped around the sheath. The exposed portion of the second insulated wire can be arranged at a different longitudinal location than the exposed portion of the first insulated wire relative to said longitudinal axis relative to said longitudinal axis. The exposed portion of the second insulated wire can be arranged at a different angular location than the exposed portion of the first insulated wire relative to a plane defined normal to said longitudinal axis.

Disclosed herein is an intravascular lithotripsy catheter for modifying calcified plaque within a blood vessel of a subject. The intravascular lithotripsy catheter can comprise a sheath with a lumen configured to receive a guidewire, a longitudinal axis extending through the lumen of the sheath, a first insulated wire, a second insulated wire, and a carrier. The first insulated wire can comprise an electrically conductive member, an insulative member encasing the electrically conductive member, and an insulative member opening forming an exposed portion of the electrically conductive member. The second insulated wire can be arranged adjacent the first insulated wire and can comprise an electrically conductive member, an insulative member encasing the electrically conductive member of the second insulated wire, and an insulative member opening forming an exposed portion of the electrically conductive member of the second insulated wire. The first and second insulated wires can be wrapped around the sheath. A transverse cross-section through the intravascular lithotripsy catheter that is perpendicular to said longitudinal axis passes through the exposed portion of the first insulated wire without passing through the exposed portion of the second insulated wire. A longitudinal cross-section through the intravascular lithotripsy catheter that is parallel to said longitudinal axis passes through the exposed portion of the first insulated wire without passing through the exposed portion of the second insulated wire.

Various combinations of the above and below recited features, embodiments, implementations, and aspects are also disclosed and contemplated by the present disclosure.

Additional implementations of the disclosure are described below in reference to the appended claims and/or clauses, which may serve as an additional summary of the disclosure.

BRIEF DESCRIPTION OF THE DRAWINGS

Various implementations will be described hereinafter with reference to the accompanying drawings. These implementations are illustrated and described by example only, and are not intended to limit the scope of the disclosure. In the drawings, similar elements may have similar reference numerals.

FIG. 2C-2F illustrate example graphs of asymmetric energy that may be emitted by an IVL catheter.

FIGS. 14A-14B depict an example implementation of a system for indicating the effectiveness of sonic pressure waves on a calcified lesion.

FIG. 18B is a schematic diagram illustrating insulated wires of an IVL catheter with electrodes forming emitters.

DETAILED DESCRIPTION

Figure 1:
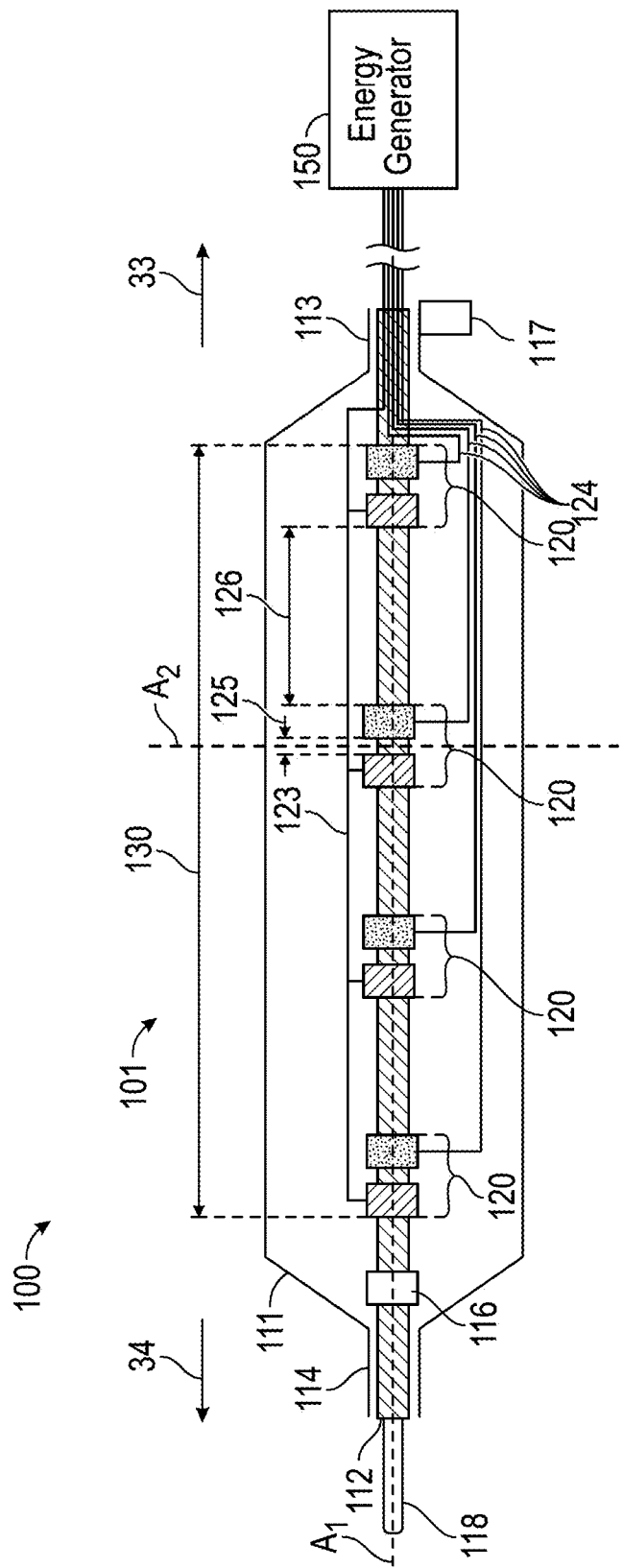
FIG. 1 illustrates an example implementation of a system that can be used to modify calcified lesions in blood vessels of a patient.

The present disclosure will now be described with reference to the accompanying figures, wherein like numerals may refer to like elements throughout. The following description is merely illustrative in nature and is in no way intended to limit the disclosure, its application, or uses. Furthermore, the devices, systems, and/or methods disclosed herein can include several novel features, no single one of which is solely responsible for its desirable attributes or which is essential to practicing the devices, systems, and/or methods disclosed herein. Additionally, the structures, systems, and/or devices described herein may be embodied as integrated components or as separate components.

Some aspects and/or implementations have been described in connection with the accompanying drawings. The scale of the figures is not limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps. Various steps within a method may be executed in different order without altering the principles of the present disclosure.

Several medical procedures have been developed to modify and/or treat calcified lesions in blood vessels. In the context of cardiovascular interventions, these procedures aim to make the calcified plaque more amendable to subsequent treatments, such as balloon angioplasty and stent placement. Some common methods for modifying a calcified lesion include rotational atherectomy, balloons (e.g., cutting, scoring, high-pressure and/or the like), excimer laser atherectomy, and/or intravascular lithotripsy (IVL), for example.

Each method has certain advantages and/or pitfalls. For example, rotational atherectomy (e.g., via a rotablator device) involves the use of a high-speed rotational device to abrade and remove calcified plaque. A rotablator device can be equipped with a diamond-coated burr that rotates at high speeds to grind away the calcifications. A rotablator process can provide one or more benefits, such as for example, by preparing a vessel wall for subsequent angioplasty.

However, the use of a rotablator has several downfalls, including a risk of dissection, where the highspeed rotational devices can potentially cause vessel dissection (e.g., a tear in the arterial wall) if not used carefully, especially in the presence of heavily calcified lesions. Further, rotational action of the rotablator device can generate plaque debris or micro-particles. Plaque debris may be released into the bloodstream causing further complications including possible downstream occlusions. In some cases, a rotablator device may not completely modify a calcified lesion as some heavily calcified lesions may be resistant to modifications. Additionally, the use of rotational blades may extend procedural time, exposing patients and physicians to prolonged safety risks associated with percutaneous procedures.

Another conventional method includes the use of several types of balloons, such as a cutting balloon, a scoring balloon, and/or a high-pressure balloon. Cutting balloons can modify calcified lesions by the use of small blades and/or microsurgical blades mounted on the balloon's surface. When a balloon is inflated, these blades create inclusions in calcified plaque, allowing for better vessel expansion during angioplasty. In some cases, a high-pressure balloon can be used. A high-pressure balloon has a rigid structure allowing for greater force during inflation to modify calcified lesions. While balloons may be effective in some context, high-pressure balloons may still carry the risk of vessel dissection or rupture if applied excessively. Scoring balloons, can pose challenges in achieving uniform scoring, potentially leaving some areas untreated. Furthermore, these balloons may generate plaque debris. Additionally, balloons may be structurally rigid, limiting a physician's ability to navigate the balloon through arteries, reducing the reachability of the balloon and versatility depending on the location of a calcified lesion.

Excimer laser atherectomy is a conventional technique using laser energy to vaporize and ablate calcified plaque. The laser energy is delivered through optical fibers within the catheter, breaking down the calcifications into smaller particles. Common issues associated with the use of a laser can include arterial perforation, where the laser's ablative action may weaken the arterial wall, increasing the risk of intended perforations. The laser may generate plaque debris and/or micro particles as described above. Further, lasers may be ineffective at ablating extremely dense calcifications. Additionally, lasers can have a limited depth of penetration when attempting to modify deep and/or extensive calcifications. Further the cost of using a laser and/or the necessary equipment associated with the use of lasers can be expensive in comparison to other methods.

An IVL catheter employs sonic waves to disrupt and modify calcified plaque by introducing the IVL catheter to, for example, a coronary artery through, a guiding catheter (guidewire). The IVL catheter can include a balloon, positioned within or adjacent to calcified plaque. A balloon can be inflated (typically with a conductive solution such as saline and/or the like), such that fluid within the balloon serves as a medium for sonic waves generated by one or more emitters within the IVL catheter. Emitters can include electrodes (e.g., wherein an electrical arc across a spark gap results in sonic waves), lasers emitting energy causing sonic waves, and/or mechanical means such as acoustic pressure causing sonic waves. Sonic waves are translated from electrode pairs, through saline, and to the outer surface of the balloon, where the energy is transferred to the walls of blood vessels. Sonic waves can generate fractures within calcified plaque, destroying the rigid structure of calcifications.

Unlike a few of the example methods for modifying calcified lesions mentioned above (e.g., rotational atherectomy, cutting balloons, scoring balloons, high-pressure balloons, excimer laser atherectomy, and/or the like), an IVL catheter can fracture associated plaque while reducing the risk of causing serious trauma to the surrounding vessel walls, as the energy source is generated within a balloon. Moreover, an IVL catheter can reduce the likelihood of particles in the bloodstream as the primary energy source is not applied directly to the vessel wall. Additionally, IVL catheters can provide a physician with more precise control over dissipated energy, thus reducing procedure time.

However, IVL catheters do suffer from performance issues that must be optimized to enhance procedural safety and efficacy. For example, emitter configurations within an IVL catheter may not optimally direct energy (e.g., sonic waves) to a specific location, resulting in poor and/or nonexistent directional control of sonic waves, dispersed energy densities, and prolonged procedures for physicians and patients alike. IVL catheters may emit energy radially, axially, longitudinally, and/or in all directions, dispersing the energy to targeted calcified lesions and/or non-targeted areas. Thus, procedural time may increase as physicians may not be able to effectively target an area having, for example, non-symmetrical calcified plaque (e.g., calcifications not uniformly distributed around the circumference of a vessel). Further, in some scenarios, when electrode pairs are not optimized to transfer energy to a specified target location, a physician may be required to generate an excessive number of sonic waves while attempting to fracture calcified plaque.

Ineffective treatment as described can increase the possibility of exceeding a IVL catheter's lifespan, increase heat generated by the IVL catheter in a blood vessel, and/or expose a patient to greater health risks associated with excessive electrical arcing (e.g., a spark when using electrodes). If, in the event that an IVL catheter's lifespan is exceeded during a procedure, the IVL catheter must be removed and replaced, thus prolonging a procedure and increasing safety and health risks to a patient. Further, the lifespan of an IVL catheter can be limited in certain circumstances when an electrode pair generates an arc in one direction. For example, when a mono-phasic energy source is used as part of an IVL catheter, electrical arcs across electrode pairs may result in burns and/or scarring at the surface of one electrode, reducing the useable life of the IVL catheter. Moreover, mono-phasic energy can induce muscular contraction leading to heart attacks.

In addition to issues associated with controlling the directionality of sonic waves, conventional IVL catheter designs may inefficiently control one or more characteristics of sonic waves. Depending on the size, shape, and location of calcified plaque, a physician may require a sonic wave having varying characteristics. Specifically, a physician may desire to alter the intensity, duration, and/or frequency of a sonic wave to optimize IVL catheter performance during a procedure. Further, conventional IVL catheters may lack the ability to alter the origin of sonic waves within the IVL catheter. For example, a physician may seek to generate sonic waves from one or more electrode pairs within the IVL catheter, to fracture a targeted grouping of calcified plaque, while seeking to prevent sonic waves generated from other electrode pairs. Conventional IVL catheter designs do not facilitate the selectivity and control that physicians desire because electrode pairs and/or each electrode within an IVL catheter may not be individually wired to an energy generation source (e.g., individually electrically connected and/or the like), nor are the electrode pairs and/or electrodes multiplexed at an associated energy source.

Conventional IVL catheter designs may be too rigid and/or too large (e.g., increased cross-sectional area) to reach and treat all the desired calcified lesions. In some scenarios, an overly rigid IVL catheter may not be able to reach highly tortuous and/or heavily calcified vessels, small vessels where navigational challenges exist, areas associated with bifurcated lesions where a single vessel divides into two branches, proximal lesions located near the origin of proximal part of the coronary arteries, and/or areas where the IVL catheter must cross occluded segments. For example, conventional manufacturing techniques for an IVL catheter can result in an excessively rigid catheter when polyethylene terephthalate (PET) tubing is used with one or more sections of the carrier and/or sheath. In some examples, manufacturers include PET tubing between electrode pairs, to protect the associated wiring from damage, however, the use of PET tubing increases the rigidity of the IVL catheter, limiting the usefulness and range of locations accessible by the IVL catheter. Further, conventional methods of manufacturing an IVL catheter may place electrode pairs outside and/or adjacent to the sheath, increasing the cross-sectional area of an IVL catheter, thus preventing the catheter from fitting into, for example, occluded segments.

Conventional IVL catheters may limit the number of pulses a physician may emit (e.g., a cycle count), as electrical arcing occurring during each pulse may slowly degrade and/or erode the surface of an electrode within an electrode pair. For example, a physician may be limited to 300 pulses during a procedure with conventional IVL catheters. Pulse limitations may result in "pulse rationing," where a physician elects to limit a number of pulses for a first calcified lesion, regardless of the effectiveness of the pulses on the first calcified lesion, in order to conserve pulses for subsequent calcified lesions. Physicians may pulse ration to reduce the number of procedures a patient may endure, reduce costs associated with having to replace an IVL catheter during a procedure, and/or as covered by a patient's medical insurance. Regardless of the reasoning, a patients may not obtain the most effective treatment due to the limited cycles associated with conventional IVL catheters.

In summary, inefficiencies associated with conventional catheters may result in ineffective treatment for a patient from low energy densities, high-energy emissions, increased procedural times, and/or broad applications of sonic waves to modify plaque, in the same way a sledgehammer relies on a user's physical strength and control to modify concrete. Whereas in contrast, one or more IVL catheters as disclosed herein can provide functionality, efficiency, longevity, and/or precision analogous to a jackhammer, by applying a targeted energy source to plaque, to quickly modify plaque while reducing risk to a patient. The issues associated with conventionally manufactured IVL catheters, and their associated systems can be overcome by one or more IVL catheter implementations and associated system designs incorporating one or more of the features as described herein. For example, an IVL catheter can be created that is flexible and/or small enough to allow physicians to navigate the IVL catheter into a broad range of desired locations within the body. An IVL catheter can maximize its useful life while efficiently targeting and fracturing calcified lesions by individually wiring electrodes to an energy generation source, incorporating a multiplexed energy generator to selectively energize electrode pairs, and/or by providing an energy source that enables a physician to configure one or more characteristics of the emitted energy (e.g., mono-phasic and/or bi-phasic pulses, changing the intensity, duration, and frequency of emitted energy, and/or the like). Further, an IVL catheter can optimize procedural time and/or procedural efficiency by controlling the directionality of sonic waves based on one or more electrode pair configurations as described herein.

The present disclosure includes example implementations and methods using an IVL catheter and/or system, to treat calcified lesions in blood vessels. Blood vessels can include arterial or veinous vasculature. Blood vessels can include coronary vessels (e.g., proximal to the heart and/or that supply blood to the heart) or peripheral blood vessels (e.g., distal to the heart such as in the arms or legs). Treating calcified lesions, deposits, plaque, build-up, etc. can include modifying said deposits. Modifying deposits etc. can refer to changing a physical structure of said deposits such as fragmenting, disintegrating, cracking, breaking, dissolving, rupturing, etc. said deposits. IVL catheters can be used in percutaneous interventions, which are procedures performed to treat blockages or narrowing in the blood vessels, such as coronary interventions or peripheral interventions. For example, a guidewire may be threaded through the vascular access site (e.g., femoral and/or radial artery) and navigated to the blood vessel treatment site with a guidewire under fluoroscopic guidance via one or more markers. An IVL catheter can be advanced over the guidewire to the site of the calcified lesion. Once in position, an IVL catheter can be activated, producing sonic waves to disrupt calcium deposits, making the deposits more manageable for subsequent interventions. Example embodiments of IVL catheters and/or one or more associated systems and/or subsystems are described below with reference to the figures.

FIG. 1 illustrates an example implementation of a system 100 that can be used to modify lesions in blood vessels of a patient. A system 100 can include an IVL catheter 101 in electrical communication with an energy generator 150. An IVL catheter 101 can include a proximal end 33 and a distal end 34. An IVL catheter 101 can be percutaneously inserted into a patient's artery by a physician. An IVL catheter 101 can be positioned in an artery where one or more calcified lesions exist. Once in position, a physician may generate one or more electrical arcs, originating from an energy generator 150 to modify a calcified lesion of a patient.

An IVL catheter 101 can include a balloon 111. A balloon 111 can have a composition including a high-quality polymer such as for example, polyethylene and/or polyamide and/or any other suitable composition. Balloon 111 can be, for example, transparent and/or opaque. A balloon 111 can have a distal end 34 and a proximal end 33. A balloon 111 can include a central portion, extending longitudinally along a carrier 112 from a proximal 33 to a distal end 34. In some examples, balloon 111 can be radially symmetric along a first axis $A_1$. A balloon 111 may have a seal 114 at a distal end and/or a seal 113 at a proximal end. Seal 113 and/or 114 can be, for example, an ultraviolet adhesive. Seal 113 and/or 114 can prevent a balloon 111 from moving axially, longitudinally, and/or radially along a carrier 112, and/or prevent loss of a solution (e.g., conductive fluid) within the balloon 111 during a procedure. In some implementations, a balloon 111 may be inflated (e.g., expanded) with a solution such as saline at a proximal end 33. Further, a balloon 111 can be deflated at a proximal end 33. In some implementations a balloon 111 can be deflated in less than three seconds. Inflation and/or deflation times for a balloon 111 may vary depending on, for example, a number of source wires 124 and/or common wires 123 (e.g., wires including a common ground) utilized as part of an IVL catheter 101. As mentioned above, a conductive solution can be used to translate one or more sonic waves from electrode pairs 120 to an outer wall of a balloon 111. In some examples, a conductive solution can enhance one or more sonic waves produced by electrode pairs 120. For examples, increasing and/or decreasing the conductivity of the conductive solution can concentrate and/or disperse one or more sonic waves produced by electrode pair 120.

A balloon 111 may deliver medication (e.g., a drug) to a target area. A surface of a balloon 111 may be coated with a drug. When a balloon 111 coated with a drug is inflated, the balloon 111 may deliver medication to a target area (e.g., cells of a blood vessel). In some cases a balloon 111 may be coated with a medication to treat, among other things, edema. Edema is a swelling, which may be caused by an IVL catheter during a procedure. Swelling may reduce the effectiveness of treatment and/or access to certain calcified lesions at a down-stream location in a blood vessel. In some examples, when a balloon 111 is coated with a drug to treat edema, the likelihood of success during a procedure can be drastically improved.

A balloon 111 can include one or more shapes as described herein. In some examples, a balloon 111 is cylindrical as depicted in FIG. 1. However the balloon 111 can be another shape such as semi-compliant and/or non-compliant shape (e.g., the balloon 111 may conform to irregularities of a blood vessels and/or remains in a given shape when inflated) along a first axis A1. A length 130 of a balloon 111 can vary based on, for example, the number of electrode pairs 120, electrode pair spacing 26, a spark gap 125, a location of one or more calcified lesions, and/or the like. In some implementations a balloon 111 can have a length 130 of about 60 mm, while in some implementations the length 130 of the balloon 111 can be approximately 58 mm. In some implementations, a balloon 111 can have an outer diameter of approximately mm, however the outer diameter can be more or less. An IVL catheter 101 can include one, two, three or more balloons 111. In some implementations, the IVL catheter 101 may not include a balloon 111.

An IVL catheter 101 can further include a carrier 112. A carrier 112 can be a flexible, elongated shaft centered along a first axis A1. A carrier 112 can facilitate the advancement and positioning of an IVL catheter 101 within a blood vessel. A cross-sectional area of a carrier 112 can have, for example, a circular, square, rectangular, hexagonal, conical, and/or any other shape along a plane intersecting a first axis A1 and/or a second axis A2 (e.g., an asymmetrical shape along a first axis A1 and/or a second axis A2). A carrier 112 can include a solid composite material. In some examples a carrier 112 can be created by a first layered composite material and a second composite material. In some examples a carrier 112 can be created with multiple layers. A carrier 112 can have a hollow channel (e.g., a lumen) extending longitudinally along a first axis A1. A hollow channel of a carrier 112 can support a guidewire 118. A guidewire 118 can assist a physician in positioning an IVL catheter 101 in a blood vessel, by allowing a carrier 112 to advance over the guidewire 118. In some implementations, a carrier 112 can have an outer diameter of approximately 0.018" although dimensions may vary depending on intended use.

An IVL catheter 101 can include electrode pairs 120. An IVL catheter 101 (e.g., as part of a system 100) can generate electrical arcing between two or more electrode pairs 120. Electrical arcing in turn generates sonic waves, transmitting energy to an outer wall of a balloon 111 to modify calcified lesions. Electrode pairs 120 can be coupled to a carrier 112 along a first axis A1. Electrodes as part of electrode pairs 120 as illustrated in FIG. 1, can be ring electrodes, however electrode pairs 120 (and/or an individual electrode of electrode pairs 120) may be any type and/or a combination of electrode types as described and/or illustrated herein. Electrodes as part of electrode pair 120 can be one or more of, and/or a combination of gold, platinum-iridium alloy, stainless steel, a nickel-titanium alloy, and/or the like. In some examples, electrode pair 120 is not adjacent to a hollow channel of a carrier 112 (e.g., not adjacent to a lumen).

Emitter spacing 126 (e.g., the spacing between two emitters) can be for example, approximately 10 mm. In another example implementation, emitter spacing 126 can be more and/or less than 10 mm depending on, for example, the intensity and/or concentration of sonic waves desired in a given location along an IVL catheter 101. FIG. 1 depicts four electrode pairs 120, however, in one implementation, an IVL catheter 101 can have five electrode pairs 120. In some implementations, emitter spacing 126 can be 11.5 mm between a first and second electrode pair, 10.5 mm between a second and third electrode pair, 9.5 mm between a third and fourth electrode pair, and/or 7.5 mm between a fourth and fifth electrode pair, beginning at a distal end 34 and/or a proximal end 33. In some examples, one or more electrodes of an electrode pair 120 can have a width of approximately 1 mm, although the width of electrodes can vary depending on the intensity and/or concentration of sonic waves desired.

Electrode pairs 120 can have a spark gap 125. A spark gap 125 may be a space between two electrodes in an electrode pair 120 (e.g., on a first and second side of, for example, a first axis A1 and/or a second axis A2), that facilitates a controlled electrical arc (e.g., electrical discharge) when electrical energy is applied to one or more electrode pairs 120. In some implementations, a spark gap 125 can be 1 mm. In some implementations a spark gap 125 can be 0.5, 1, 2, 3, 4, 5, and/or more mm. In some implementations a spark gap 125 can vary from one electrode pair 120 to another electrode pair 120. Further, a spark gap 125 can be more or less than 1 mm depending on the desired intensity and/or concentration of desired pressure sonic waves at a given location in an IVL catheter 101. Advantageously, a spark gap 125 can be designed to direct sonic waves toward a calcified plaque as described below.

Electrode pairs 120 can further include a common wire 123 and source wires 124. Wire 123 and/or 124 can be electrically connected to one or more electrodes of an electrode pair 120 and to an energy generator 150. Wires 123 and/or 124 can carry electrical energy from an energy generator 150 to an electrode pair 120 to generate an electrical arc across spark gap 125. In some implementations, a system 100 can include individual wires 123 and/or 124 for each electrode in an electrode pair 120, enabling an energy generator 150 to individually control each electrode pair 120 (e.g., an N×2 configuration where "N" is the number of electrode pairs 120). However, individually wiring each electrode pair 120 may result in an increased diameter of the overall dimensions of an IVL catheter 101, as two wires may be fitted in the IVL catheter 101 for each electrode pair 120. Advantageously, an N×2 configuration can be used to selectively generate a spark gap 125 between any two electrodes within an IVL catheter 101. In some implementations, a system 100 can have one common wire 123 and individual source wires 124, as depicted in FIG. 1. For example, one electrode of each electrode pair 120 can be individually wired to an energy generator 150, and a second electrode of each electrode pair 120 can be electrically connected together with a common wire 123 (e.g., an N+1 configuration where "N" is the number of electrode pairs 120). Advantageously, wiring electrode pairs 120 in an N+1 configuration can reduce the number of wires 123 and/or 124 within an IVL catheter 101 in comparison to individually wired electrode pairs 120 as mentioned above. For example, the number of wires 123 and/or 124 decreases for a number of electrode pairs 120 as one moves from a proximal end 33 to a distal end 34 of an IVL catheter 101, as depicted in FIG. 1. In addition to a reduced overall diameter for an IVL catheter 101, an N+1 wiring configuration enables an energy generator 150 to individually control each electrode pair 120 as only one of the electrodes are individually wired, via source wire 124, to an energy generator 150 as further described with reference to FIGS. 2A-2B below. As illustrated in FIG. 1, common wire 123 and/or source wires 124 can be routed outside the carrier 112. In some implementations, wire 123 and/or 124 can be routed within (e.g., beneath an outer surface, embedded, and/or the like) a carrier 112.

An IVL catheter 101 can further include markers 116. Markers 116 can used during a procedure to help a physician visualize and position IVL catheter 101. Markers 116 can be radiopaque markers that can be visible under fluoroscopy and/or X-ray imaging. Further, markers 116 can be alignment markers used to position IVL catheter 101 accurately within specific anatomical landmarks to the target calcified lesion within a blood vessel. Markers 116 can be positioned at a distal end 34, a proximal end 33 and/or at any other part of an IVL catheter 101. Further, there can be one or more markers 116, each positioned at varying locations within an IVL catheter to assist a physician in alignment and treatment such as on a carrier 112, a balloon 111, and/or any other area.

An IVL catheter 101 may include an indicator 117. An indicator 117 can be a check valve, a pressure sensor, a flow indicator, temperature sensor, and/or another sensor to determine a change in state of an IVL catheter 101. An indicator can be coupled to an inner surface, an outer surface, and/or within an inner surface of a balloon 111. Alternatively and/or optionally an indicator 117 may be at another location within a system 100 such as positioned along the carrier 112, as part of and/or along a proximal seal 114 and/or a distal seal 113, as part of an energy generator 150, coupled to a hollow channel as defined by the carrier 112, along a inflation lumen (depicted as part of FIG. 14A-14B), and/or the like.

An indicator 117 may sense a change in state, (e.g., a physical property) such as a change in pressure, flow, temperature, motion (e.g., a vibration), volume, and/or the like, of one or more components of an IVL catheter 101. In some examples, the indicator 117 may detect a pressure change in the balloon 111. A balloon 111 may experience a pressure fluctuation once a calcified lesion is successfully broken. As an illustrative example, during a successful treatment of a calcified lesion by an IVL catheter 101, a balloon 111 may expand in volume, and thus experience a pressure decrease within the balloon 111. Indicator 117 may sense a pressure drop within the balloon 111 once the volume of the balloon 111 increases. The indicator 117 may therefore indicate to a user, that an IVL procedure successfully modified a calcified lesion. Additionally and/or optionally, an indicator 117 may sense a change in pressure and/or flow of conductive fluid within a balloon 111 due to a ruptured balloon 111.

A system 100 can further include an energy generator 150. An energy generator 150 can provide electrical energy (e.g., current) to electrode pairs 120 as mentioned above. Additionally, the energy generator 150 can generate one or more electrical patterns by changing the frequency, pulse width, amplitude, pulse polarity, pulse shape and/or phase of one or more pulses transmitted to electrode pairs 120 to further alter the intensity, duration, and/or directionality of one or more sonic waves to modify a calcified lesion. In some implementations, an energy generator 150 can transmit electrical energy to electrode pairs 120 at a minimum rate of approximately 5 Hz. In some implementations, an energy generator 150 can transmit electrical energy to electrode pairs 120 at a minimum rate less than and/or more than 5 Hz (e.g., 1, 2, 3.5, 10 Hz and/or the like). As further described with reference to FIGS. 2A-2B, an energy generator 150 can selectively emit energy to one or more electrode pairs 120 based on, for example the use of a multiplexer and/or can be used along with additional devices to improve patient safety by synchronizing a patient's cardiac rhythm with one or more IVL generated sonic waves.

Figure 2A:
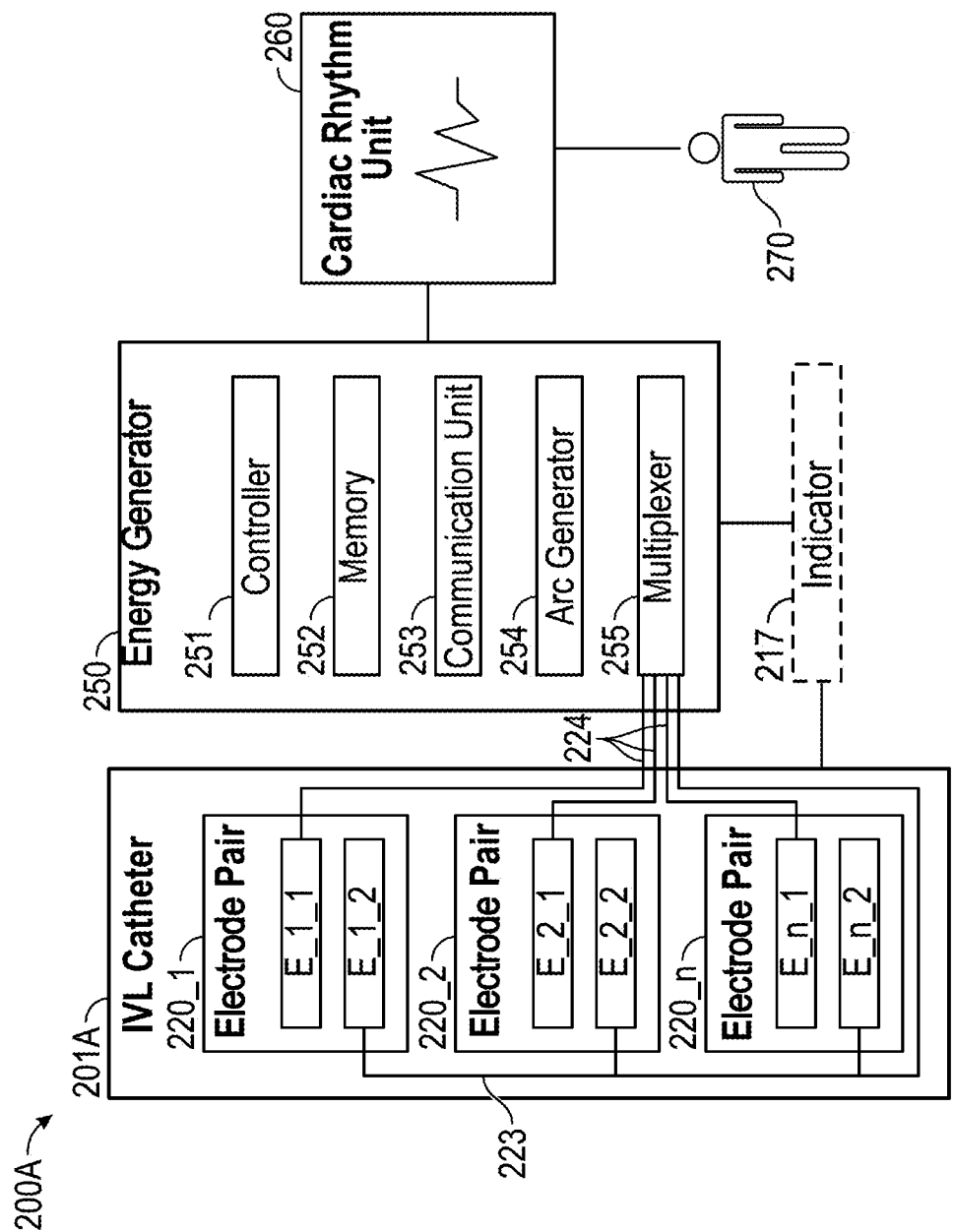
FIG. 2A is an example block diagrams of a cardiac synchronization system.
Figure 2B:
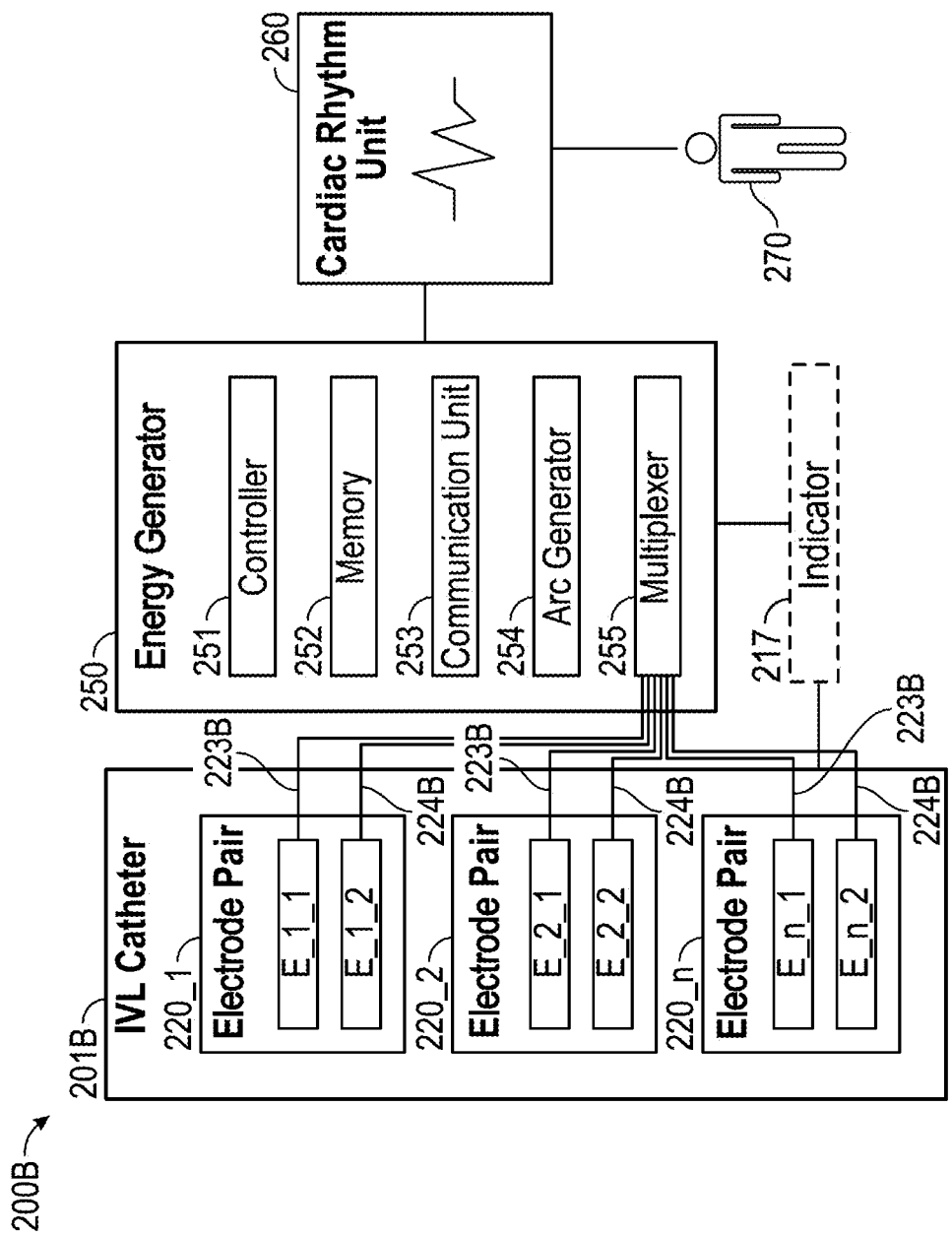
FIG. 2B is an example block diagram of a cardiac synchronization system with individually wired electrodes.

FIGS. 2A-2B are an example block diagrams of a cardiac synchronization system 200A and/or 200B. As illustrated in FIG. 2A, a cardiac synchronization system 200A can be used to improve the safety and efficacy of an IVL procedure. A cardiac synchronization system 200A can include an IVL catheter 201A, energy generator 250, cardiac rhythm unit 260, and a patient 270. An IVL catheter 201A can be electrically connected to an energy generator 250 via wires 223 and/or 224. An IVL catheter 201A can be configured to receive electrical energy from an energy generator 250 in response to a physician's request to generate sonic waves in the IVL catheter 201A. An energy generator 250 can be in further communication with a cardiac rhythm unit 260. For example, the cardiac rhythm unit 260 can transmit data (e.g., via wired and/or wirelessly) associated with a cardiac rhythm of a patient 270 to energy generator 250.

As mentioned above, during an IVL procedure, electrical arcs may be generated in an IVL catheter 201A. Sonic waves created from electrical arcs are used to modify calcified lesions. In some procedures, an IVL catheter 201A can be positioned in close proximity to the heart of a patient 270 and/or other electrically sensitive organs. Advantageously, timing electrical arcs in an IVL catheter 201A according to a cardiac rhythm of a patient 270 during an IVL procedure can mitigate certain health risks.

An IVL catheter 201A can be the same and/or similar to IVL catheter 101 as described with reference to FIG. 1 and/or any of the additional configurations as mentioned herein. In some examples, an IVL catheter 201A can have electrode pairs 220 (e.g., electrode pair 220_1, 220_2, 220_n), each electrode pair 120 can include at least two electrodes (e.g., E_1_1 and/or E_1_2 for electrode pair 220_1). Electrode pairs 220 can be configured in an N+1 configuration as mentioned in above and as illustrated in FIGS. 1-2A. In some implementations, electrode pairs 220 can be electrically connected via wires 223 and/or 224, in another configuration (e.g., in parallel, series, individually wired, and/or the like). In some examples, electrode pairs 220 are electrically connected to a multiplexer 255 via wires 223 and/or 224. In some examples, electrode pairs 220 are electrically connected to another component such as arc generator 254.

An IVL catheter 201A can include an indicator 217. Indicator 217 can be the same as and/or similar to an indicator 117 of FIG. 1. An indicator 217 can include, for example, a check valve, a pressure sensor, a flow indicator, temperature sensor, motion sensor, and/or another sensor to determine a change in state of an IVL catheter 201A. An indicator 217 may indicate to a user, that an IVL procedure successfully modified a calcified lesion, that a balloon 111 has ruptured, and/or the like.

A cardiac rhythm unit 260 can transmit (e.g., wirelessly and/or wired) information associated with a patient 270 cardiac rhythm to, for example, an energy generator 250. Further, a cardiac rhythm unit 260 can transmit a discrete signal based on one or more triggering events associated with a patient 270 cardiac rhythm to an energy generator 250. A cardiac rhythm unit 260 can be any device designed to monitor and/or determine one or more characteristics of a patient 270 cardiac rhythm including but not limited to: a heart rate, P waves (electrical activity associated with the upper chambers), QRS complex (lower chambers of the heart), PR interval (the time between the beginning of the P wave and the start of the QRS complex), QT interval (time between the start of the QRS complex to the end of the T wave), T wave (ventricular repolarization), and/or the like. In some examples, the cardiac rhythm unit 260 can be an AccuSync® 72 ECG trigger monitor. In some examples, a cardiac rhythm unit 260 can detect an R-wave signal and in response, transmit a discrete signal to an energy generator 250 based on one or more triggering events associated with the R-wave signal.

A cardiac synchronization system 200A can include an energy generator 250. An energy generator 250 can include a controller 251, memory 252, a communication unit 253, an arc generator 254, and/or a multiplexer 255. An energy generator 250 can transmit electrical energy to electrode pairs 220 of an IVL catheter 201A.

An energy generator 250 can include a controller 251, memory 252, and/or a communication unit 253. An energy generator 250 can store information obtained by a controller 251 in memory 252. Examples of information stored in memory 252 can include operational data such as electrical patterns, a counter to determine a lifespan of an IVL catheter 201A based on the emitted energy form energy generator 250, and/or information associated with cardiac synchronization (e.g., a threshold and/or the like). In some examples, a counter can generate an alert after the counter determines that an IVL catheter 201A exceeded a threshold number of pulses (e.g., 100, 200, 300, and/or more pulses). Additionally, an energy generator 250 includes a communication unit 253. A communication unit 253 can transmit and/or receive data from, for example, a cardiac rhythm unit 260. For example, a communication unit 253 may receive data representing a cardiac rhythm of a patient 270, and/or a discrete signal from a cardiac rhythm unit 260. A discrete input can be, for example, representative of a timeframe enabling an energy generator 250 to transmit electrical energy to an IVL catheter 201A. Additionally and/or optionally, a discrete signal can disable an energy generator 250 from emitting electrical energy to the IVL catheter 201A.

A controller 251 can determine one or more electrical characteristics of electrical energy transmitted to electrode pairs 120. For example, a controller 251 can determine the frequency, amplitude, pulse width (e.g., duty cycle), pulse shape, pulse polarity, and/or phase of one or more electrical pulses as created by the arc generator 254. A controller 251 can change one or more electrical characteristics based on, for example, an input form a user (e.g., a physician conducting an IVL procedure). A controller 251 can change electrical characteristics of energy transmitted to an IVL catheter 201A based on a user's input regarding one or more aspects of a calcified lesion such as the location, quantity, and/or concentration of a calcified lesion. In some examples, a controller 251 can determine an electrical pattern as created by an arc generator 254. An electrical pattern can include a pulse width, an amplitude, a frequency, pulse shape, pulse polarity, a duration, and/or the like. In some examples, an electrical pattern can be linear, a random burst, a square wave, a triangle wave. An electrical pattern can further include selectively emitting energy to one or more electrode pairs 220. For example, a controller 251 can instruct a multiplexer 255 to select one or more channels based on, for example a desired electrical pattern as described herein.

Additionally and/or alternatively, a controller 251 can determine whether to emit a monophasic pulse and/or a biphasic electrical pulse. In some examples, a controller 251 can instruct the arc generator 254 to emit a monophasic pulse, where the polarity of one electrode in electrode pairs 220 is positive and/or another electrode in electrode pairs 220 is negative. In a monophasic pulse, the current creating an arc traveling in one direction, from a first electrode (e.g., E_1_1) to a second electrode (e.g., E_1_2). Consequently, a monophasic pulse can create weld spots on the surface of one electrode. Over time, these weld spots may reduce the control and/or directionality of sonic waves, increase component degradation, and/or cause premature electrode failure.

Advantageously, a controller 251 can instruct an arc generator 254 to generate biphasic pulses. Biphasic pulses deliver electrical energy in two phases, a positive phase and/or a negative phase. Thus current (and/or electrical arcs) flowing through an electrode pair 220 can alternate between positive and/or negative. A biphasic pulse can increase reliability and/or lifespan of an IVL catheter 201A as weld spots are less likely to accumulate on one electrode. In some implementations, a controller 251 can instruct an arc generator 254 to combine one or more patters based on a user input. For example, a controller 251 can instruct an arc generator 254 to create an electrical pattern having a monophasic pulse, a biphasic pulse, a frequency, pulse width, amplitude, phase, pulse shape, and/or the like, to increase the reliability and/or lifespan of an IVL catheter 201A.

In some examples, a controller 251 can instruct an arc generator 254 to generate asymmetric pulses (e.g., biphasic pulses where a positive pulse and/or a negative pulse are asymmetric with respect to one another). Asymmetric pulses can include varying rise and/or fall times (e.g., a slope), varying energy levels, and/or the like, for a positive and/or negative pulse. Advantageously, asymmetric pulses may increase the longevity of electrode pairs 120, and thus increase the lifespan of an IVL catheter 101, as erosion and/or pitting resulting from arcing may be more evenly distributed, and/or heat may be efficiently dissipated in comparison to symmetric pulse patterns.

An asymmetric pulse may be characterized by different energy levels on a positive and/or on a negative portion of a biphasic pulse. As an illustrative example, a positive pulse may include a larger voltage difference (e.g., $\Delta V$) and/or a longer pulse width in comparison to a negative pulse. As another example, a negative pulse may have a shorter $\Delta V$ for a longer duration than a positive pulse. In some examples, an asymmetric pulse can have multiple $\Delta V$s and/or differing rise and/or fall times for positive and/or negative pulses. As an illustrative example, a positive pulse can be characterized by a first $\Delta V$ for a first duration at a first slope, and a second $\Delta V$ for a second duration at a second slope, while a negative pulse can be characterized by a third $\Delta V$ for a third duration at a third slope, and a fourth $\Delta V$ for a fourth duration at a fourth slope.

Additionally and/or alternatively, a controller 251 can determine and/or adjust an energy level for positive and/or negative pulses of an asymmetric pulse based on an estimated amount of heat generated by the arc generator 254. For example, a controller 251 may generate a first pulse and/or set of pulses having approximately a 10 μs pulse width and adjust the pulse width accordingly based on a calculated heat generation and/or dissipation associated with an electrode pair 220 (e.g., as an illustrative example and not meant to be limiting, based on a spark gap 125, 325, 425, 525 and/or the like). A controller 251 may calculate heat dissipation based on, among other factors, an area of the body receiving treatment, the number and/or frequency of pulses, the type of arc generator 254, the type, position, quantity, composition and/or another property associated with electrode pairs 220, and/or the like.

In some examples, a controller 251 can instruct an arc generator 254 to emit energy such that an electric field is generated at and or near an electrode pair 220. In some examples, the controller 251 may instruct a first electrode and a second electrode to emit energy to cause an electric filed according to one or more electrical characteristics associated with increasing the efficacy of a medication into an arterial wall via reversable electroporation. An electric field may be controlled such that sonic pressure waves do not result from a spark gap. In some examples, an electric field may be applied to endothelial cells during a procedure. An electric field may increase the efficacy of a medication from, for example, a drug-coated balloon 111 of FIG. 1 as described herein.

In some implementations, a controller 251 can instruct an arc generator 254 to emit electrical energy to electrode pairs 220 at and/or near the resonance frequency of plaque within an artery, to efficiently facilitate the modification of plaque. Plaque, like any item in the physical world, has a resonance frequency. When plaque is subjected to an external force at a resonance frequency (e.g., sonic waves form an IVL catheter such as 101, 201A, 201B, and/or the like), the plaque exhibits maximum vibrational amplitudes by absorbing and/or storing energy, resulting in significant oscillations inevitably modifying the plaque. In some examples, a resonance frequency is determined by inherent characteristics of plaque (e.g., mass, stiffness and/or the like). In some examples, a controller 251 can instruct an arc generator 254 to emit electrical energy at the resonance frequency of plaque (e.g., approximately 54 Hz). In some examples, a controller 251 can instruct an arc generator 254 to emit electrical energy having a resonance frequency range from approximately 10 Hz to 55 Hz. In some examples, a controller 251 can instruct an arc generator 254 to emit electrical energy at the resonance frequency of plaque, wherein the frequency is greater than 5 Hz. However, the controller 251 can instruct the arc generator 254 to emit electrical energy at a resonance frequency greater than and/or less than 5 Hz (e.g., 1, 2, 6.5, 10.1, and/or the like). In some examples, a controller 251 can instruct an arc generator to emit electrical energy having one or more electrical patters including a resonance frequency, a pulse width, an amplitude, a pulse polarity, a pulse shape and/or a phase as described herein.

Additionally and/or optionally, a controller 251 can instruct an arc generator 254 to emit electrical energy that may include one or more of and/or a combination of features and/or electrical characteristics as described herein. As an illustrative example, a controller 251 can instruct an arc generator 254 to emit a biphasic and/or asymmetric pulse shape wherein a positive pulse is associated with a first energy level and a negative pulse is associated with a second energy level.

In some examples, a controller 251 can receive an input from a cardiac rhythm unit 260. Based on a received input from a cardiac rhythm unit 260, a controller 251 can determine one or more periods to enable and/or disable electrical energy to an IVL catheter 201A. A controller 251 can analyze one or more characteristics of a cardiac rhythm including: a heart rate, P waves (electrical activity associated with the upper chambers), QRS complex (lower chambers of the heart), PR interval (the time between the beginning of the P wave and/or the start of the QRS complex), QT interval (time between the start of the QRS complex to the end of the T wave), T wave (ventricular repolarization), and/or the like. In some examples, when an IVL catheter 201A is located within close proximity to the heart (e.g., coronary arteries, coronary veins, and/or the like), a controller 251 can determine, based on the cardiac rhythm received from a cardiac rhythm unit 260, that an arc generator 254 should be disabled. In some examples, a controller 251 can ignore requests from a user (e.g., a physician) to generate one or more arcs in an IVL catheter 201A based on a patient 270 cardiac rhythm.

In some examples, a controller 251 can determine whether to transmit electrical energy to electrode pairs 220 located at a distal and/or proximal end of an IVL catheter 201A while preventing the transmission of electrical energy to other electrode pairs 220, based on the received cardiac rhythm. For example, a controller 251 can instruct multiplexer 255 to transmit electrical energy to electrode pair 220_1 while further instructing multiplexer to prevent transmission of electrical energy to electrode pair 220_2. In some examples, a controller 251 can instruct the multiplexer 255 to select one or more channels to increase the concentration of sonic waves at a specific location within a blood vessel.

In some examples, a controller 251 can indicate the state of an IVL catheter (e.g., whether a procedure was successful) based on an indicator 217. For example, a controller 251 may receive an input from an indicator 217, which may measure a state of an IVL catheter 201A, (e.g., a physical property) such as a change in pressure, flow, temperature, motion (e.g., a vibration), volume, and/or the like. In some examples, the controller 251 may determine that the pressure within an IVL catheter 201A has changed based on a change in a volume of a balloon (e.g., balloon 111 of FIG. 1). In some examples, the controller 251 may indicate that an IVL procedure successfully modified a calcified lesion based on a detected pressure fluctuation as described with reference to FIGS. 14A-14B.

An energy generator 250 can further include an arc generator 254. An arc generator 254 can create one or more electrical pulses based on, for example, an instruction from controller 251. Arc generator 254 can create an electrical arc pattern having one or more characteristics such as a monophasic pulse, a biphasic pulse, a frequency, pulse width, a symmetric and/or asymmetric pulse shape, amplitude, phase, and/or the like. An arc generator 254 can transmit one or more arc patterns to, for example, multiplexer 255. Additionally and/or alternatively, arc generator 254 can be wired directly to one or more electrode pairs 220 and/or transmit one or more arc patterns directly to electrode pairs 220. Further, arc generator 254 can generate one or more arc patterns simultaneously. For example, an arc generator 254 can transmit a first arc pattern and/or a second arc pattern to a multiplexer 255, such that a first set of electrode pairs 220_1 create sonic waves based on a first arc pattern, and/or a second set of electrode pairs 220_2 create sonic waves based on a second arc pattern.

An energy generator 250 can further include a multiplexer 255. A multiplexer 255 can include any number of channels corresponding to the number of electrode pairs 220 associated with an IVL catheter 201A (e.g., one, two, three, four, or more). A multiplexer 255 can receive instructions form a controller 251, and/or in response, select one or more electrode pairs 120 to generate arcs in accordance with a controller 251 determined arc pattern. A multiplexer 255 be configured to select one or more electrode pairs 220 based on, for example, a desired concentration of sonic waves at a target location in a blood vessel, and/or the like.

To induce a spark, energy generator 250, under control of the controller 251, can drive the wires 223B, 224B with voltage such as between 1000V and 5000V, between 1000V and 4000V, between 1000V and 3000V, between 1000V and 2000V, between 2000V and 4000V, between 1500V and 3000V, between 1500V and 2500V, or between 2000V and 3000V, or any value therebetween. The voltage provided by the energy generator 250 can be the difference in voltage between two wires or the absolute value of the voltage driven on a single wire. The wires 223B, 224B can have an impedance of thousands of Ohms depending on the implementation, which may increase with smaller electrode surface area. The energy generator 250 can drive the wires 223B, 224B at the voltage for a duration between 1 μs and 50 μs, between 1 μs and 40 μs, between 1 μs and 30 μs, between 1 μs and 20 μs, between 1 μs and 10 μs, between 1 μs and 5 μs, between 5 μs and 50 μs, between 10 μs and 50 μs, between 20 μs and 50 μs, between 30 μs and 50 μs, between 40 μs and 50 μs, between 1 μs and 25 μs, between 25 μs and 50 μs, or any value therebetween. The time during which the energy generator 250 drives the voltage may depend inversely on the voltage such that a higher voltage requires a shorter time duration and vice versa. For example, the energy generator 250 can drive the wires 223B, 224B at 1500V for 50 μs to induce a spark or can drive the wires 223B, 224B at 3000V for somewhere between 1 μs and 10 μs to induce a spark. Driving the wires 223B, 224B under such conditions can results in hundreds of milliamps of current drawn from the energy generator 250 to the wires 223B, 224B.

The impedance between electrodes in an emitter (e.g., between 1 and 10 Ohms) may be less than the impedance of the wires themselves such that when a spark forms between electrode pairs it can result in an increased current draw (e.g., 30 A-40 A) from the energy generator 250 for a few additional microseconds (e.g., 4 μs-10 μs) at the same voltage output.

In some examples, one or more components and/or functions of the cardiac synchronization system 200A can be combined. For example, arc generator 254 and/or multiplexer 255 can include one or more components designed to generate arc patterns and/or select electrode pairs 220 in response to one or more instructions received from controller 251. Additionally and/or alternatively, an energy generator 250 and/or a cardiac rhythm unit 260 can be combined into one and/or more units that may determine one or more aspects of a patient 270 cardiac rhythm and/or determine whether to enable/disable the transmission of electrical energy to one or more electrode pairs 220, and/or transmit electrical energy to the electrode pairs 220.

FIG. 2B is an example implementation of a cardiac synchronization system 200B having an IVL catheter 201B with individually wired electrode pairs 220. One or more components of a cardiac synchronization system 200B can be the same and/or similar to that of cardiac synchronization system 200A. As depicted in FIG. 2B, a cardiac synchronization system 200B can be in electrical communication with electrode pairs 220_1, 220_2, and/or 220_n of an IVL catheter 201B. In some implementations, each electrode within an electrode pair (e.g., electrodes E_1_1 and/or E_1_2 of electrode pair 220_1 can be individually wired via wires 223B and/or 224B to, for example, multiplexer 255. Advantageously, a cardiac synchronization system 200B can have each electrode wired (e.g., via wires 223B and/or 224B) individually to a multiplexer 255, to generate a spark gap between any two electrodes. For example, in some implementations, a spark gap can exist between electrodes E_1_1 and/or E_1_2, while in some implementations a spark gap can exist between E_1_1 and/or E_2_1. Additionally and/or alternatively, a spark gap can exist between electrode pairs E_1_1 and/or E_2_1 while a second spark gap exists between E_1_2 and/or E_2_2. In some implementations, multiplexer 255 can selectively transmit a mono-phasic and/or bi-phasic pulse between any combination of electrodes such that an electrical arc travels in one or more direction across a spark gap.

FIGS. 2C-2F illustrate example graphs 200C-200F of pulse patterns that may be generated by an energy generator 250. The example graphs 200C-200F are illustrative examples of pulse patterns and are not meant to limit the scope of this disclosure. In some examples, a controller 251 may instruct an energy generator 250 to emit one or more pulses having a rise time and/or fall time similar to pulse examples illustrated in graphs 200C-200F. Additionally and/or optionally, a controller 251 may instruct an energy generator 250 to emit pulses having a different energy level, frequency, intensity, duration and/or the like than what is depicted in graphs 200C-200F.

Graph 200C illustrates an example of a symmetric pulse pattern. A symmetric pulse pattern as depicted in graph 200C may generate substantially equal amounts of energy for a positive pulse and a negative pulse via the same and/or similar waveforms (e.g., pulses, step functions, energy levels, and/or the like).

Example graphs 200D-200F illustrate asymmetric pulse patterns. As described above, asymmetric pulse patterns can include varying rise and/or fall times (e.g., a slope), a biphasic pulse including varying energy levels based on polarity, and/or the like. Advantageously, asymmetric pulses may increase the longevity of electrode pairs 220, and thus increase the lifespan of an IVL catheter 201A, as erosion and/or pitting resulting from arcing may be more evenly distributed, and/or heat may be efficiently dissipated in comparison to symmetric pulse patterns.

Graph 200D illustrates an example of an asymmetric pulse that generates an equal amount of energy for both a positive and negative pulse. For example, although a positive pulse may have a higher intensity (e.g., voltage) for a shorter duration in comparison to a negative pulse, the total energy emitted by a positive pulse and a negative pulse may be equal and/or substantially equal as the total area above and below 0 volts is approximately equal. Graphs 200E, 200F illustrate examples of asymmetric pulses having different intensities, durations, and/or energy levels.

Although graphs 200D-200F depict positive pulses followed by negative pulses, this is not meant to be limiting. For example, a negative pulse may be emitted from electrode pairs 220, followed by a positive pulse. Additionally and/or optionally, pulses do not necessarily have to alternate. For example, one, two, three and/or more negative and/or positive pulses may succeed a first pulse. As an illustrative example, a first negative pulse may be succeeded by an additional negative pulse, and then a positive pulse. Advantageously, generating a bi-phasic pulse pattern (e.g., with positive pulses and a negative pulses) and/or an asymmetric pulse pattern can reduce the likelihood of inducing muscular contractions. Accordingly, the systems and devices described herein can implement intravascular lithotripsy near the heart without risking inducing a heart attack.

One or more example emitter implementations as part of an IVL catheter are described herein with reference to FIGS. 3A-3E and/or 4A-4E. Example implementations of emitters can be used as part of, for example, IVL catheter 101, 201A, 201B, and/or in any other example implementation of an IVL catheter as described herein.

One or more components of an IVL catheter (e.g., emitters, wires, balloon, carrier, and/or the like) can be configured to optimize sonic waves to modify a calcified lesion. Optimizing the intensity and/or directionality of sonic waves can provide physicians and/or patients alike with several benefits. For example, an efficiently operating IVL catheter generates less heat, thereby reducing a blood vessel's exposure to higher temperatures. An efficient IVL catheter can decrease the pulse counts required to modify calcified lesions, thus reducing overall procedure times. Further, an efficient IVL catheter can modify calcified lesions located at multiple locations within a blood vessel without requiring replacement, thus increasing the efficacy of a procedure. An IVL catheter can optimize the directionality and/or intensity of sonic waves by, for example, positioning electrodes at a distal end, a proximal end, within a carrier, and/or outside a carrier. Further, a shape and/or size of electrodes, a spark gap, and/or the configuration of one or more locations of an electrode pair and/or associated wiring can result in a smaller, lighter, more flexible, and/or hence more efficient IVL catheter as described herein.

Figure 3A:
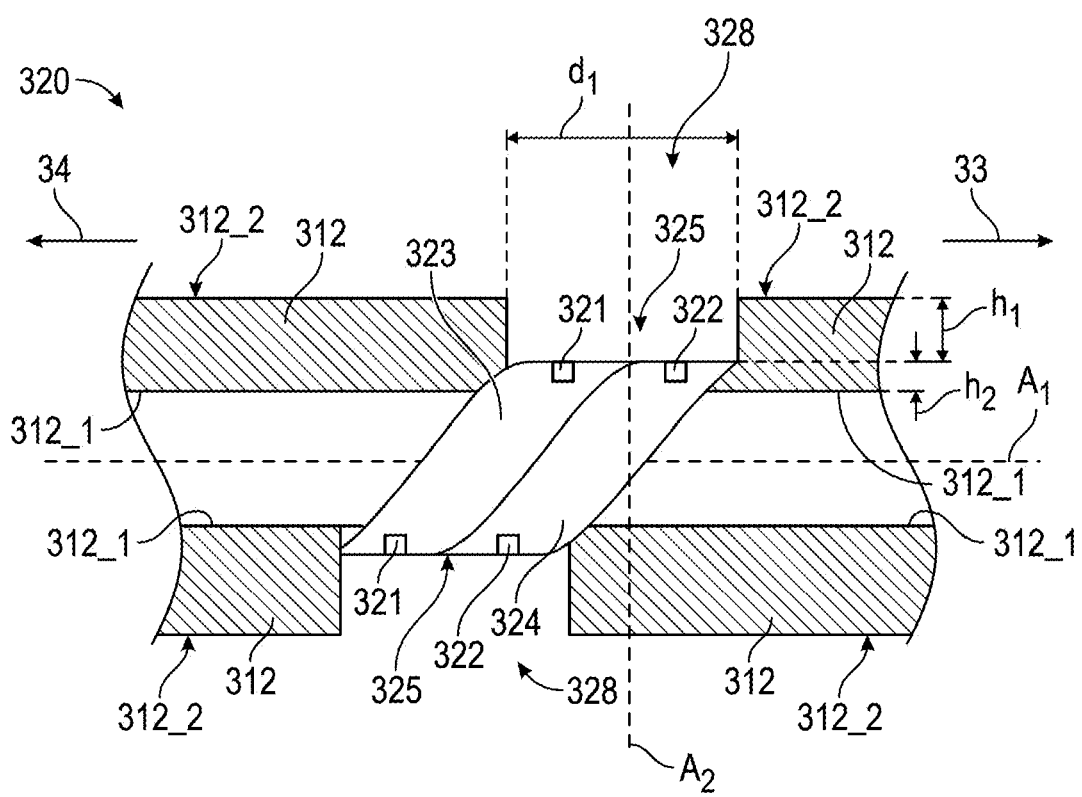
FIG. 3A illustrates an example side-view of a helically wound electrode pair as part of an IVL catheter.

FIG. 3A is an example side view of a helically wound electrode pair 320. Electrode pair 320 can be electrically similar and/or the same as electrode pair 120 of FIG. 1. In some examples, an IVL catheter, such as IVL catheter 101 and/or 201A, 201B, and/or the like, can have one or more electrode pairs 320 electrically connected to an energy generator 250 to create an arc within an IVL catheter.

In some examples, carrier 312 can be the same and/or similar to carrier 112 of FIG. 1. For example, carrier 312 can have a solid core and/or a hollow channel along a first axis A1. A carrier 312 can be configured with a hollow channel to support, for example a guidewire (e.g., guidewire 118 of FIG. 1) therethrough. A carrier 312 can have an inner surface 312_1 and an outer surface 312_2. The carrier 312 can have a volume between the inner surface 312_1 and an outer surface 312_2 that can house electrodes 321 and/or 322. The inner surface 312_1 of a carrier 312 can form, for example, a lumen along a first axis A1. The outer surface 312_2 can have one or more recessed channels 328. In some examples, carrier 312 can have a recessed channel 328 as shown in cross section of electrode pair 320 (e.g., a cross-section along a plane intersecting a first axis A1. For example, carrier 312 can have a recessed channel 328 beginning at a proximal end 34 and/or ending at a distal end 33. In some examples, a recessed channel 328 can create a helix around a carrier 312.

A recessed channel 328 can have a first height $h_1$ of approximately 0.02 to 0.1 mm. A first height $h_1$ of a recessed channel 328 can be measured from one or more wires 323 and/or 324 to an outer surface 312_2 of the carrier. In some examples, a first height $h_1$ more and/or less than 0.03 mm (e.g., 0.001, 0.01, 0.1, 0.2, 0.4, 1 and/or the like). A recessed channel can have a second height $h_2$ measured from one or more wires 323 and/or 324 to the inner surface 312_1. The second height $h_2$ can be approximately 0.02 to 0.06 mm. In some examples, the second height $h_2$ can be more and or less than approximately 0.02 to 0.06 mm (e.g., 0.001, 0.01, 0.1, 0.2, 0.3, 1, 2, and/or more). In some examples, a recessed channel 328 can have a distance $d_1$ of approximately 0.25 to 0.07 mm. In some examples, a distance $d_1$ of a recessed channel 328 can be more and/or less than 0.25 to 0.07 mm (e.g., 0.01, 0.1, 0.2, 0.3, 1, 2, and/or more). A first height $h_1$ and a second height $h_2$ can determine, for example, the depth of a recessed channel 328 and/or a proximity of wires 323 and/or 324 to an inner surface and/or the outer surface 312_2 of a carrier 312. In some examples, a recessed channel 328 has a varying first height $h_1$ and/or distance $d_1$ depending on the number of conductive wires 323 and/or 324 included in the recessed channel 328. In some examples, a recessed channel 328 has a reduced first height h and/or distance $d_1$ at a distal end of the carrier 312 in comparison to a proximal end. In some implementations, a recessed channel 328 can have one or more geometric shapes as depicted in FIGS. 3A-3E.

Advantageously, insulated conductive wires 323 and/or 324 can be beneath (e.g., embedded, below, and/or the like) a recessed channel 328 of carrier 312 and/or an outer surface 312_2 of a carrier 312, to optimize the directionality and/or control of sonic waves generated by an electrode pair 320. Positioning wires 323 and/or 324 beneath a recessed channel and/or an outer surface 312_2 can, in some cases, reduce an overall diameter of an IVL catheter as measured along a first axis A1. Moreover, an arc between electrode 321 and/or 322 of electrode pair 320 can generate sonic waves within the recessed channel 328, (e.g., beneath the outer wall and/or spaced inward from an outer surface) of the carrier 312, thus directing sonic waves outward towards a targeted lesion in a blood vessel. Further, a carrier 312 can have a spark gap 325. A spark gap 325 can be, for example, a notch exposing electrode 321 and/or 322. In some examples, carrier 312 can include a spark gap 325 for each electrode pair 320. In some examples, a first spark gap 325 can be positioned on a distal end 34 of a second axis A2, while a second spark gap 325 can be positioned on a proximal end of a second axis A2. Further, a carrier 312 can include a plurality of spark gaps 325 positioned longitudinally, helically, and/or radially along a first axis A1 and/or a second axis A2 of the carrier 312.

Electrode pair 320 can include insulated conductive wires 323 and/or 324 (hereinafter "wire" 323 and/or 324). Wire 323 and/or 324 can be in electrical communication with, for example an energy generator 250 as illustrated in FIG. 2A-2B. Wire 323 and/or 324 can be a 36 AWG wire (e.g., copper wire insulated with one or more insulating materials). In some examples the wire gauge of wire 323 and/or 324 can be more and/or or less than 36 AWG (e.g., 34, 35, 37, 38, 39, and/or the like). In some examples, wire 323 can be a first wire gauge while wire 324 can be a second wire gauge. Although FIG. 3A depicts one of wire 323 and/or 324, additional implementations can include multiple wires 323 and/or 324. For example, wire 323 and/or 324 can be configured in an N+1 configuration as described herein, to selectively transmit electrical energy to one or more electrode pairs 320. In some configurations, electrode pair 320 can be wired in another configuration such as in parallel, series, individually wired (e.g., such as system 200B of FIG. 2B), and/or the like.

In some examples, electrode pair 320 can include a first electrode 321 and/or a second electrode 322. Electrodes 321 and/or 322 can be for example, a part of wire 323 and/or 324 including a portion where the insulation has been removed to expose a conductor. In some examples, the conductor can be copper wire. In some examples, electrodes 321 and/or 322 can be electrodes welded to the conductor of wire 323 and/or 324. Electrodes 321 and/or 322 can have a spark gap 325 therebetween. A spark gap 325 can be, for example, 1 mm. However, spark gap 325 can be wider and/or narrower depending on the configuration. For example, FIG. 3A depicts electrodes 321 and/or 322 in similar locations along wire 323 and/or 324 respectively. Electrode 321 and/or 322 can be positioned proximally 33 and/or distally 34 along wire 323 and/or 324 to increase and/or decrease spark gap 325 as necessary. In some examples, an electrode pair 320 can include multiple sets of electrodes 321, 322, and/or spark gaps 325 along a recessed channel 328 of carrier 312. In some examples, a recessed channel can have one or more geometries as depicted in FIGS. 3A-3E below.

Although FIG. 3A depicts electrodes 321 and/or 322 proximate to one another, in some implementations, electrodes 321 and/or 322 can be separated, and/or beneath the outer surface 312_2 of the carrier 312, (e.g., in a volume between the inner surface 312_1 and an outer surface 312_2). For example, electrode 322 may be located proximate to an inner surface 312_1 of a carrier 312, while electrode 321 may be located proximate to an outer surface 312_2 of the carrier 312. In some examples, electrodes 321, and/or 322 can be individually wired as described with reference to FIG. 2B to facilitate individual control of one or more electrodes, to selectively generate an arc between any two electrodes.

As mentioned above, an IVL catheter having a large outer diameter as measured along a second axis A2 may not be able to navigate one or more occluded segments in a blood vessel, thus limiting the IVL catheter's use. To expand the applicability of an IVL catheter, one design choice may reduce the overall diameter of the IVL catheter. However, as the diameter of an IVL catheter is decreased, so too may the structural integrity of the IVL catheter decrease. In some examples, an IVL catheter's outer diameter can be reduced to a point where the IVL catheter becomes too flexible, to the point where physicians are unable to navigate the IVL catheter into a desired blood vessel. Advantageously, to overcome this problem, wire 323 and/or 324 may be wrapped in a helical shape around the carrier 312, to increase the overall rigidity of an IVL catheter while reducing the overall diameter of the IVL catheter. Wire 323 and/or 324 can be wrapped around a carrier 312 along a first axis $A_1$, beginning at a proximal end 33 and/or ending at a distal end 34. In some examples, insulated conductive wire 323 and/or 324 can be wrapped in a helical shape around a carrier 312 as described above and/or wrapped along the outer surface 312_2 the carrier.

FIGS. 3A-3E illustrate examples of additional geometric shapes for a recessed channel 328 of electrode pair 320. In some examples, a recessed channel 328 can have the same shape throughout a carrier 312. In some implementations a recessed channel 328 can have a varying shape. In some implementations, a carrier 312 can include one or more recessed channels 328 and/or the like, by removing a volume between an outer surface 312_2 and an inner surface 312_1. For example, a recessed channel 328 can be created when a proximal sidewall of a carrier 312 has a first geometric shape, while a distal sidewall of the carrier 312 has a second geometric shape. FIGS. 3A-3E are a few examples of additional geometric shapes for a recessed channel and are not meant to be limiting. Other shapes and/or a combination of one or more shapes not illustrated in FIGS. 3A-3E may be implemented. Advantageously, a recessed channel 328, 328a, 328b, 328c, 328d, and/or the like can be implemented by a system (e.g., 100, 200A, 200B, and/or the like) to efficiently control the directionality and/or concentration of emitted energy as the result of one or more electrical arcs between two electrodes (e.g., electrodes 321 and/or 322).

Figure 3B:
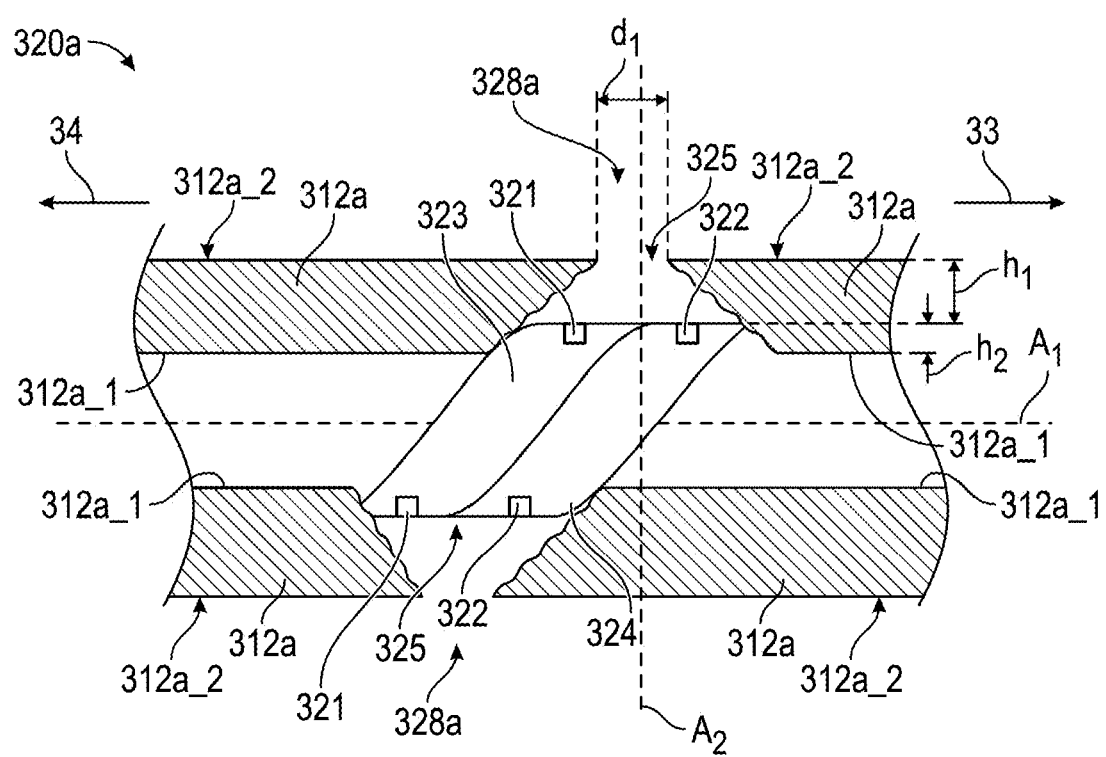
FIG. 3B-3E illustrate example geometric shapes for a recessed channel as part of an IVL catheter.

FIG. 3B illustrates an example electrode pair 320a having a recessed channel 328a as part of a carrier 312a. In some examples, a recessed channel 328a can have a distance $d_1$ along an outer surface 312a_2 that is less than a distance of spark gap 325 and/or less than a distance of the recessed channel 328a proximate to an inner surface 312a_1. In some examples, the distance $d_1$ can be less than and/or the same as a distance of spark gap 325 along an outer surface 312a_2. In some examples, a carrier 312a can form a recessed channel 328a by removing a portion of the outer surface 312a_2. As depicted in FIG. 3B, a carrier 312a can form a recessed channel 328a having a substantially angled sidewall on a proximal 33 and/or distal 34 end of a second axis A2.

Figure 3C:
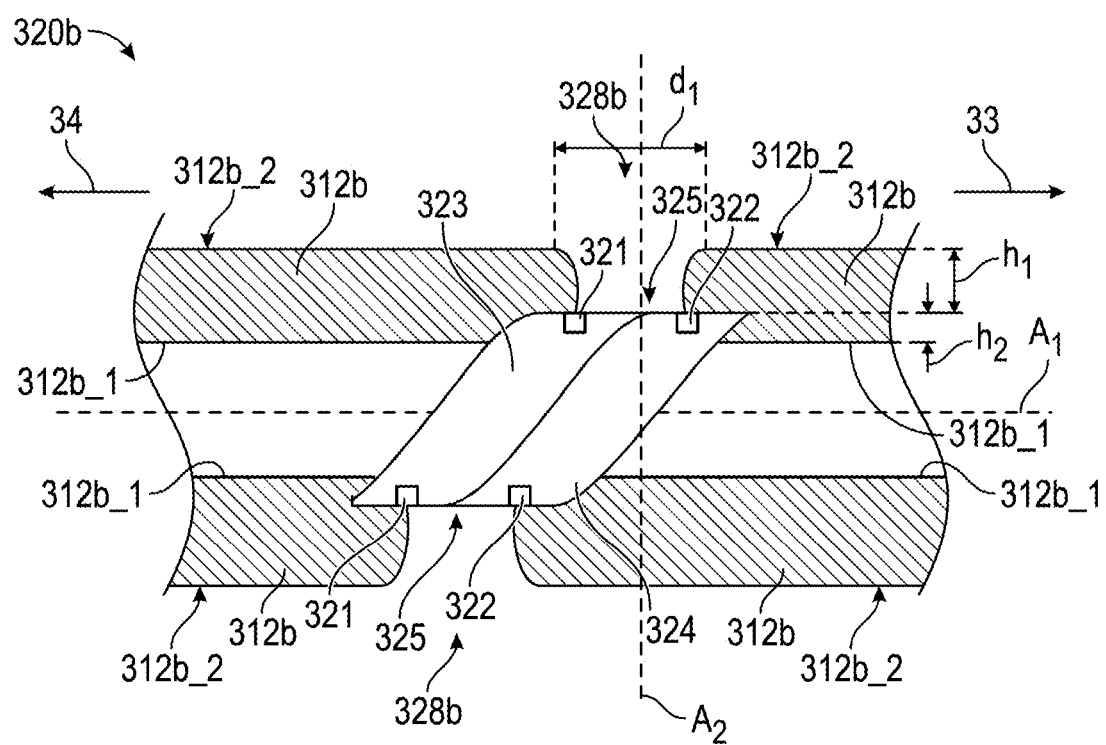

FIG. 3C illustrates an example electrode pair 320b having a recessed channel 328b as part of a carrier 312b. The recessed channel 328b can have a substantially convex sidewall on a proximal 33 and/or distal 34 end along a second axis A2. In some examples, a recessed channel 328b can have a distance $d_1$ along an outer surface 312b_2 of the carrier 312b, that is less than a distance of spark gap 325 and/or less than a distance of the recessed channel 328b proximate to the inner surface 312b_2. In some examples, the distance $d_1$ can be greater and/or the same as a distance of spark gap 325. In some examples, a carrier 312b can form a recessed channel 328b by removing a portion of the outer surface 312b_2 as depicted in FIG. 3C.

Figure 3D:
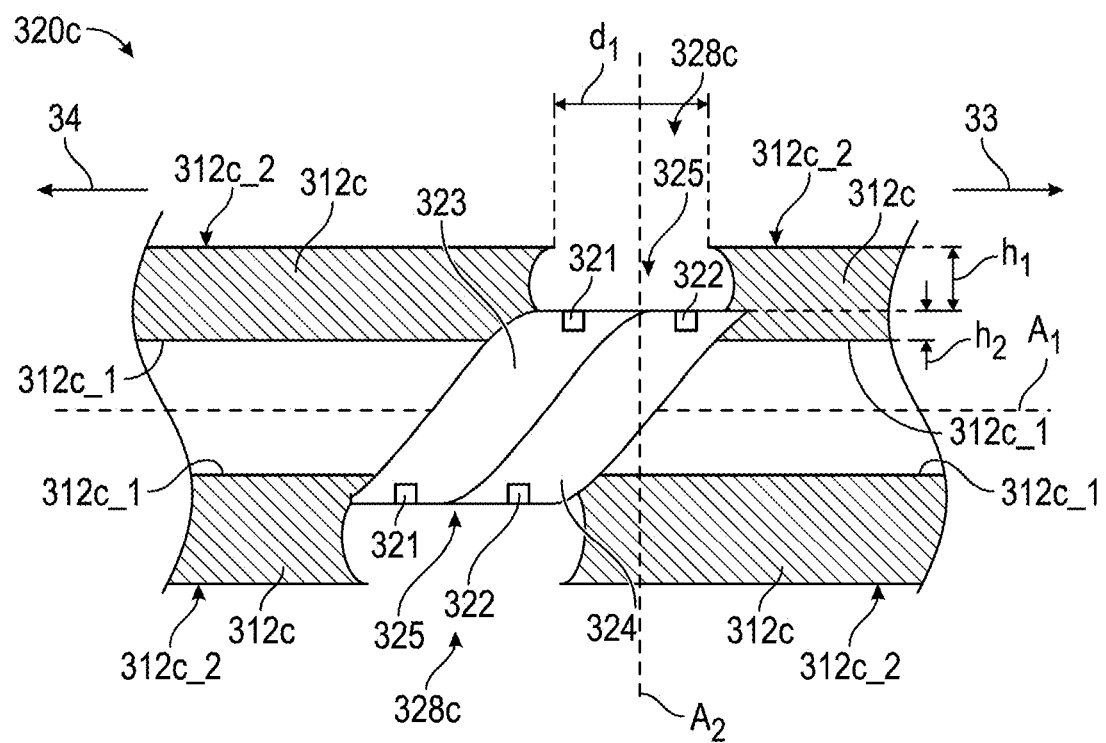

FIG. 3D illustrates an example electrode pair 320c having a recessed channel 328c as part of a carrier 312c. The recessed channel 328c can have a substantially concave sidewall on a proximal 33 and/or distal 34 end along a second axis A2. In some examples, a recessed channel 328c can have a distance $d_1$ that is less than a distance of spark gap 325. In some examples, the distance $d_1$ can be greater than and/or the same as a distance of spark gap 325. In some examples, a carrier 312c can form a recessed channel 328c by removing a portion of the outer surface 312c_2 as depicted in FIG. 3D.

Figure 3E:
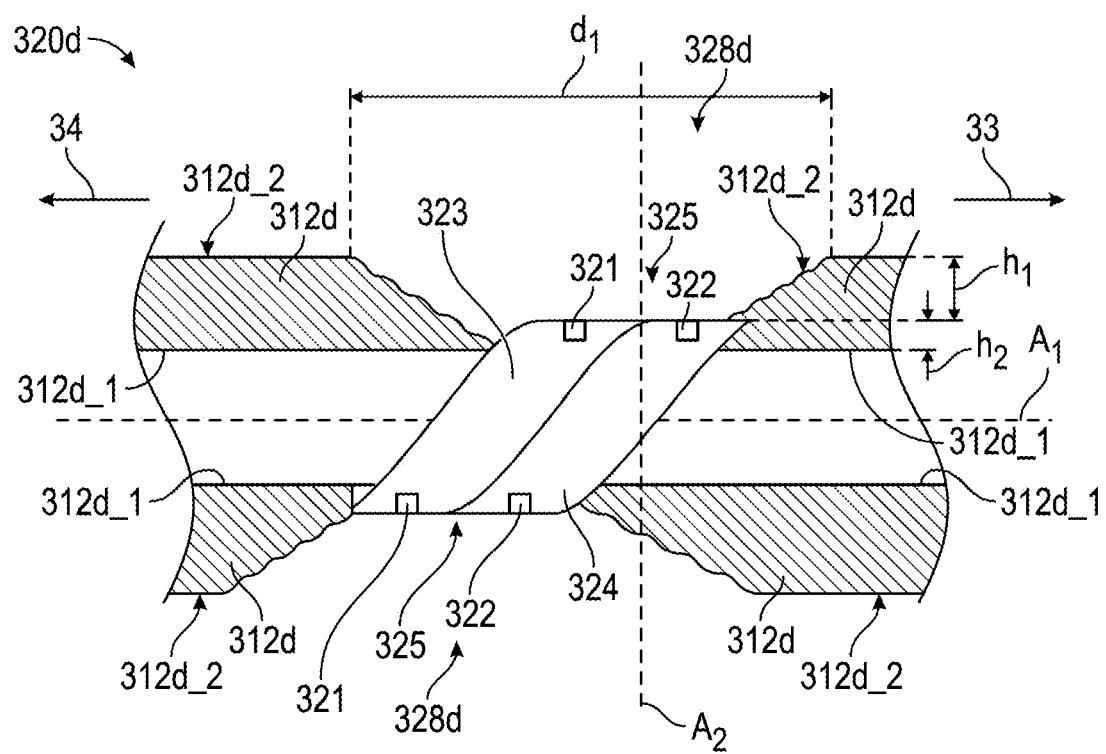

FIG. 3E illustrates an example electrode pair 320d having a recessed channel 328d as part of a carrier 312d. In some examples, a recessed channel 328d can have a distance $d_1$ along an outer surface 312d_2 that is greater than a distance of spark gap 325 and/or greater than a distance of the recessed channel 328d proximate to an inner channel 312d_1. In some examples, the distance $d_1$ can be substantially greater than and/or approximately the same as a distance of spark gap 325 along an outer surface 312d_2. In some examples, a carrier 312d can form a recessed channel 328d by removing a portion of the surface of the outer surface 312d_2. As depicted in FIG. 3E, a carrier 312d can form a recessed channel 328d having a substantially angled sidewall on a proximal 33 and/or distal 34 end of a second axis A2.

As described herein, a system can include any combination of electrode pairs (e.g., 120, 220, 320, 320a-d, 420, 420a-d and/or the like) with one or more combinations of recessed channels in a carrier to efficiently direct energy towards plaque of an artery. In some examples, a system can include one or more recessed channels. Recessed channels can include one or more electrode pairs. In some examples, a recessed channel can have one or more of the example geometries as described herein and/or the like.

Figure 4A:
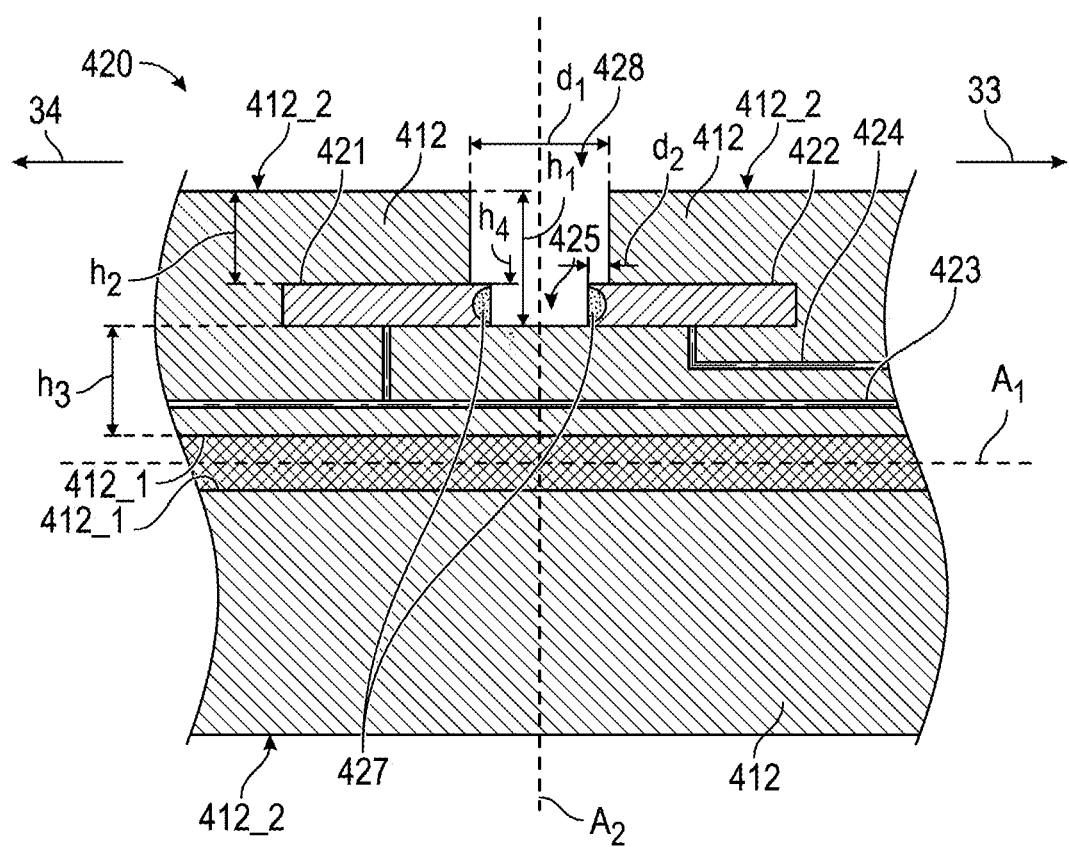
FIG. 4A illustrates an example cross-sectional view of an embedded electrode pair as part of an IVL catheter.

FIG. 4A is an example cross-sectional view along a plane intersecting a first axis A1. FIG. 4A depicts an embedded electrode pair 420. Electrode pair 420 can be electrically similar and/or the same as electrode pair 120 of FIG. 1. In some examples, an IVL catheter, such as IVL catheter 101, 201A, 201B, and/or the like, can have one or more electrode pairs 420 electrically connected to an energy generator 250 to create an arc within an IVL catheter.

In some examples, carrier 412 can be the same and/or similar to carrier 112 of FIG. 1. Carrier 412 can have a solid core and/or a hollow channel along a first axis A1. A carrier 412 can be configured with a hollow channel to support, for example a guidewire (e.g., guidewire 118 of FIG. 1) therethrough. A carrier 412 can have an inner surface 412_1 and an outer surface 412_2. The carrier 412 can have a volume between the inner surface 412_1 and the outer surface 412_2. The volume can house electrodes 421 and/or 422. The inner surface 412_1 of a carrier 412 can form, for example, a lumen along a first axis A1. The outer surface 412_2 can have a notch 428 as depicted in cross section of electrode pair 420. Advantageously, electrodes 421 and/or 422 can be beneath (e.g., below, embedded within, and/or the like) the outer surface 412_2 of a carrier 412. Electrodes 421 and/or 422 can be exposed via a notch 428 along a proximal 33 and/or distal 34 side of a second axis A2. Electrodes 421 and/or 422 can be exposed to, for example, conductive fluid of an IVL catheter. Further, carrier 412 can include a cavity 427. A cavity 427 can be, for example an additional area defining a spark gap 425 included as part of electrodes 421 and/or 422. In some examples, a cavity 427 can be located on one, both, or none of the electrodes 421 and/or 422. In some implementations a cavity 427 can be included as part of a carrier 412 (e.g., an inner surface 412_1 and/or an outer surface 412_2 and/or the like). In some examples, electrode 421 and/or electrode 422 can include at least one cavity 427. In some examples, a first electrode of an electrode pair 420 (e.g., electrode 421 and/or 422) can include at least one cavity 427 while a second electrode of an electrode pair 420 (e.g., electrode 421 and/or 422) does not include at least one cavity 427. Advantageously, a cavity 427 along with the notch 428 of carrier 412 can be configured to optimize the directionality and/or control of sonic waves generated by an electrode pair 420. For example, an arc between electrode 421 and/or 422 of electrode pair 420 can generate sonic waves within a notch 428 (e.g., beneath the outer surface 412_2 and/or spaced inward from an outer surface 412_2) of the carrier 412, thus directing the sonic waves outward towards a targeted area of a blood vessel. Further, a carrier 412 can have a solid core and/or the carrier 412 can include a hollow channel defined by an inner surface 412_1 (e.g., along a first axis A2), creating a lumen therethrough (e.g., to support guidewire 118 of FIG. 1).

Electrode pair 420 further includes electrodes 421 and/or 422. Electrodes 421 and/or 422 can be embedded within a carrier 412. Additionally and/or alternatively, electrodes 421 and/or 422 can be positioned below (e.g., inward form an outer surface) an outer wall of the carrier 412. During the manufacturing process of carrier 412, an outer wall of carrier 412 can be removed to generate a notch 428 as illustrated in FIG. 4A, thus exposing electrodes 421 and/or 422 and/or creating spark gap 425.

A notch 428 can have a first height $h_1$ from approximately 0.04 to 0.3 mm on a proximal 33 and/or distal 34 end along a second axis A2. A first height h1 can be, for example, measured form the outer surface 412_2 to a bottom portion of a notch 428. In some examples, a first height $h_1$ of a notch 428 can be more and/or less than approximately 0.04 to 0.3 mm (e.g., 0.001, 0.01, 0.1, 0.2, 0.4, 1 and/or the like). A notch 428 can have a second height $h_2$ measured from, for example, a top portion of an electrode pair 420 to an outer surface 412_2 along a second axis A2. A second height $h_2$ can be approximately 0.01 to 0.06 mm along a second axis A2. In some examples, the height $h_2$ of a notch 428 can be more and/or less than 0.01 to 0.06 mm (e.g., 0.001, 0.01, 0.1, 0.2, 0.4, 1 and/or the like). A notch 428 can have a third height $h_3$ measured from, for example, a top portion of an electrode pair 420 to an inner surface 412_1 along a second axis A2. A third height $h_3$ can be approximately 0.01 mm along a second axis A2. In some examples, a third height $h_3$ of a notch 428 can be more and/or less than approximately 0.01 to 0.03 mm (e.g., 0.001, 0.01, 0.1, 0.2, 0.4, 1 and/or the like). A notch 428 can have a fourth height $h_4$ measured from, for example, a top portion of an electrode pair 420 to an outer surface 412_2. A fourth height $h_4$ can be more and/or less than approximately 0.01 to 0.05 mm along a second axis A2. In some examples, a fourth height $h_4$ of a notch 428 can be more and/or less than approximately 0.01 to 0.05 mm (e.g., 0.001, 0.01, 0.1, 0.2, 0.4, 1 and/or the like). In some examples, a notch 428 can have a first distance $d_1$ of a notch 428 as measured along an outer surface 412_2 of a carrier 412. In some examples a first distance $d_1$ can be measured from a proximal 33 and/or distal 34 end along a second axis $A_2$. A first distance $d_1$ can be, for example, approximately 0.05 to 0.1 mm. In some examples, a first distance $d_1$ of a notch 428 can be more and/or less than approximately 0.05 to 0.1 mm (e.g., 0.01, 0.1, 0.2, 0.3, 1, 2, and/or more). In some examples, a notch 428 can have a second distance $d_2$ of a notch 428 as measured from a proximal 33 and/or distal 34 side of a notch 428 to a proximal 33 and/or distal 34 end of an electrode 421 and/or 422. A second distance $d_2$ can measure, for example, the amount of an electrode (e.g., electrode 421 and/or 422) extending into a notch 428 along a first axis A1. In some examples a second distance $d_2$ can be measured from a proximal 33 and/or distal 34 end along a second axis A2. A second distance $d_2$ can be, for example, approximately 0.01 to 0.03 mm. In some examples, a second distance $d_2$ can be more and/or less than approximately 0.01 to 0.03 mm (e.g., 0.01, 0.1, 0.2, 0.3, 1, 2, and/or more). In some examples, a notch 428 and/or one or more aspects of an electrode pair 420 can have a varying height $h_1$, $h_2$, $h_3$, $h_4$, and/or distance $d_1$, $d_2$, depending on the number of conductive wires 423 and/or 424, and/or type of electrodes 421 and/or 422 included and/or exposed to notch 428. In some examples, a notch 428 has a reduced height $h_1$, $h_2$ and/or distance $d_1$ at a distal end of a carrier 412 in comparison to a proximal end.

In some implementations, a first electrode 421 can be positioned at a distal end 34 and/or a second electrode 422 can be positioned at a proximal end 33 along a second axis A2. In some implementations, electrodes 421 and/or 422 can be positioned longitudinally, radially, axially, and/or at any other location along a first axis A1 and/or a second axis A2.

In some implementations, a spark gap 425 can be created by positioning electrodes 421 and/or 422 longitudinally, radially, axially, and/or at any other location along a carrier 412, and/or exposing one or more portions of the carrier 412 (e.g., removing at least a portion of an outer surface 412_2 and/or the like).

Further, a composition of electrodes 421 and/or 422 can be one or more of a combination of gold, platinum-iridium alloy, stainless steel, a nickel-titanium alloy, and/or the like. Electrodes 421 and/or 422 can be electrically connected to conductive wires 423 and/or 424 as illustrated. In some examples, conductive wires 423 and/or 424 can be welded to electrodes 421 and/or 422. Conductive wires 423 and/or 424 can be configured in an N+1 configuration as described herein, to selectively transmit electrical energy to one or more electrode pairs 420. In some configurations, electrode pair 420 can be wired in another configuration such as in parallel, series, individually wired (e.g., such as system 200B of FIG. 2B), and/or the like.

In some implementations, an IVL catheter can include one or more of electrode pairs 120, 320, 420, and/or the like. Additionally, and/or alternatively, an IVL catheter can include one or more sections having varying carrier configurations such as carrier 112, 312, and/or 412 and/or the like.

FIGS. 4A-4D illustrate examples of additional geometric shapes for a notch 428 of electrode pair 420. In some examples, a notch 428 can have the same shape along a first axis A1 and/or a second axis A2. In some implementations a notch 428 can have a varying shape along a first axis A1 and/or a second axis A2. In some implementations, a carrier 412 can include more than one notch 428 and/or the like. For example, a notch 428 can be created having a first geometric shape on a proximal 33 end and a second geometric shape on a distal 34 end along a second axis A2. FIGS. 4A-4E are a few examples of additional geometric shapes for a notch 428, inner surface 412_1 and/or outer surface 412_2 of a carrier 412 and are not meant to be limiting. Other shapes and/or a combination of one or more shapes not illustrated in FIGS. 4A-4E may be implemented. Advantageously, a notch 428, 428a, 428b, 428c, 428d, and/or the like can be implemented by a system (e.g., 100, 200A, 200B, and/or the like) to efficiently control the directionality and/or concentration of emitted energy as the result of one or more electrical arcs between two electrodes.

Figure 4B:
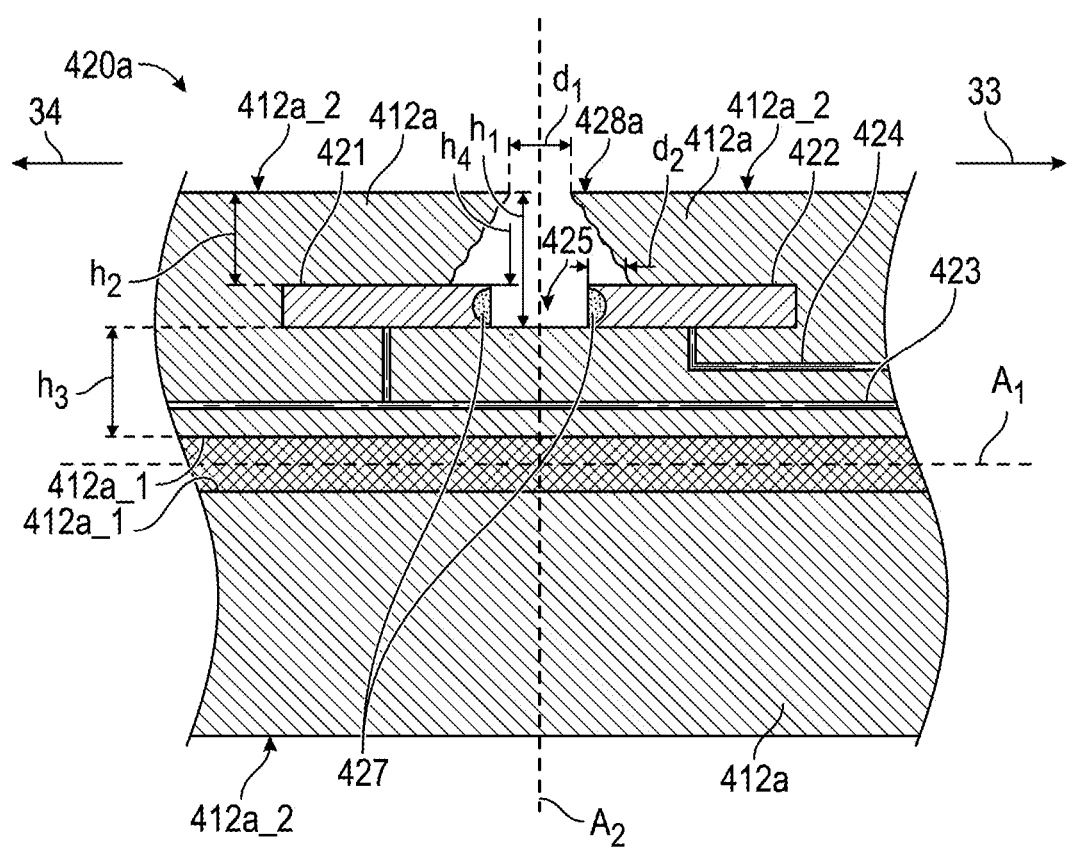
FIGS. 4B-4E illustrate example geometric shapes for a notch as part of an IVL catheter.

FIG. 4B illustrates an example electrode pair 420a having a notch 428a as part of a carrier 412a. In some examples, a notch 428a can have a distance $d_1$ along an outer surface 412a_2 that is less than a distance of spark gap 425 and/or less than a distance of the notch 428a proximate to an inner surface 412a_1. In some examples, the distance $d_1$ can be less than and/or the same as a distance of spark gap 425 along an outer surface 412a_2. In some examples, a carrier 412a can form a notch 428a by removing a portion of the outer surface 412a_2. As depicted in FIG. 4B, a carrier 412a can form a notch 428a having a substantially angled sidewall on a proximal 33 and/or distal 34 end of a second axis A2.

Figure 4C:
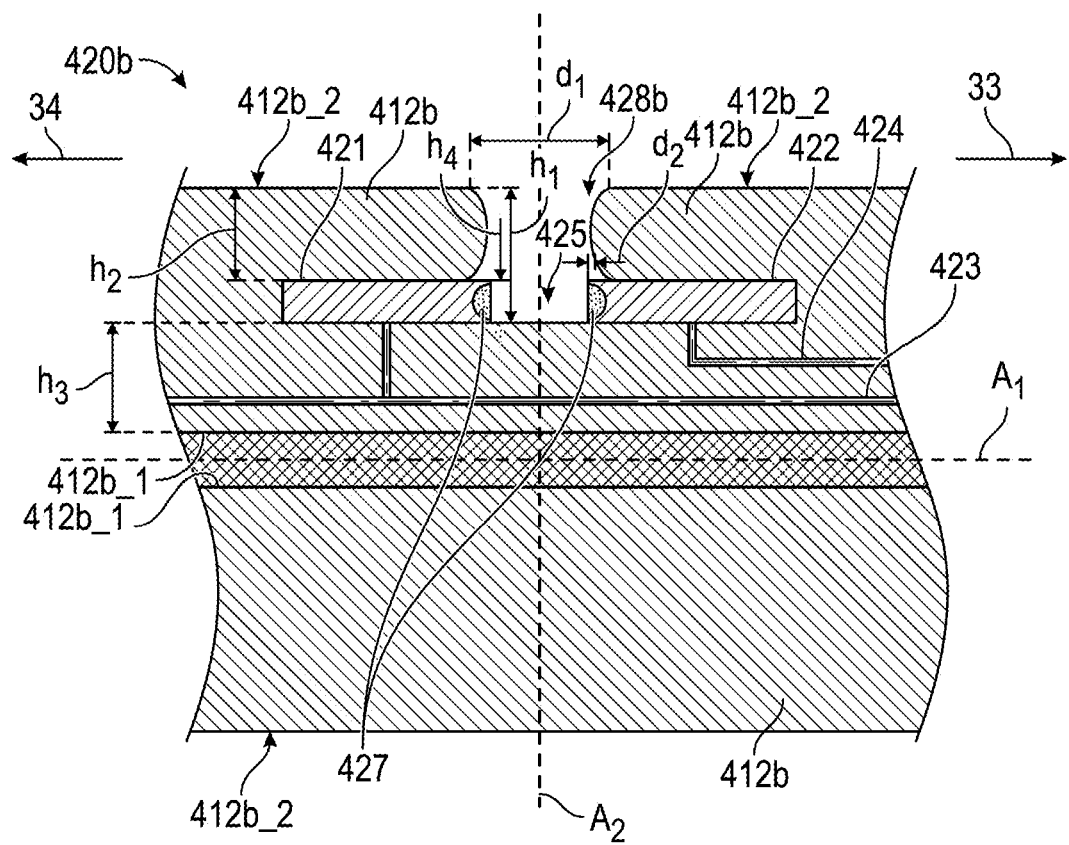

FIG. 4C illustrates an example electrode pair 420b having a notch 428b as part of a carrier 412b. The notch 428b can have a substantially convex sidewall on a proximal 33 and/or distal 34 end along a second axis A2. In some examples, a notch 428b can have a distance $d_1$ along an outer surface 412b_2 of the carrier 412b, that is less than a distance of spark gap 425 and/or less than a distance of the notch 428b proximate to the inner surface 412b_2. In some examples, the distance $d_1$ can be greater and/or the same as a distance of spark gap 425. In some examples, a carrier 412*b* can form a notch 428*b* by removing a portion of the outer surface 412*b*_2 as depicted in FIG. 4C.

Figure 4D:
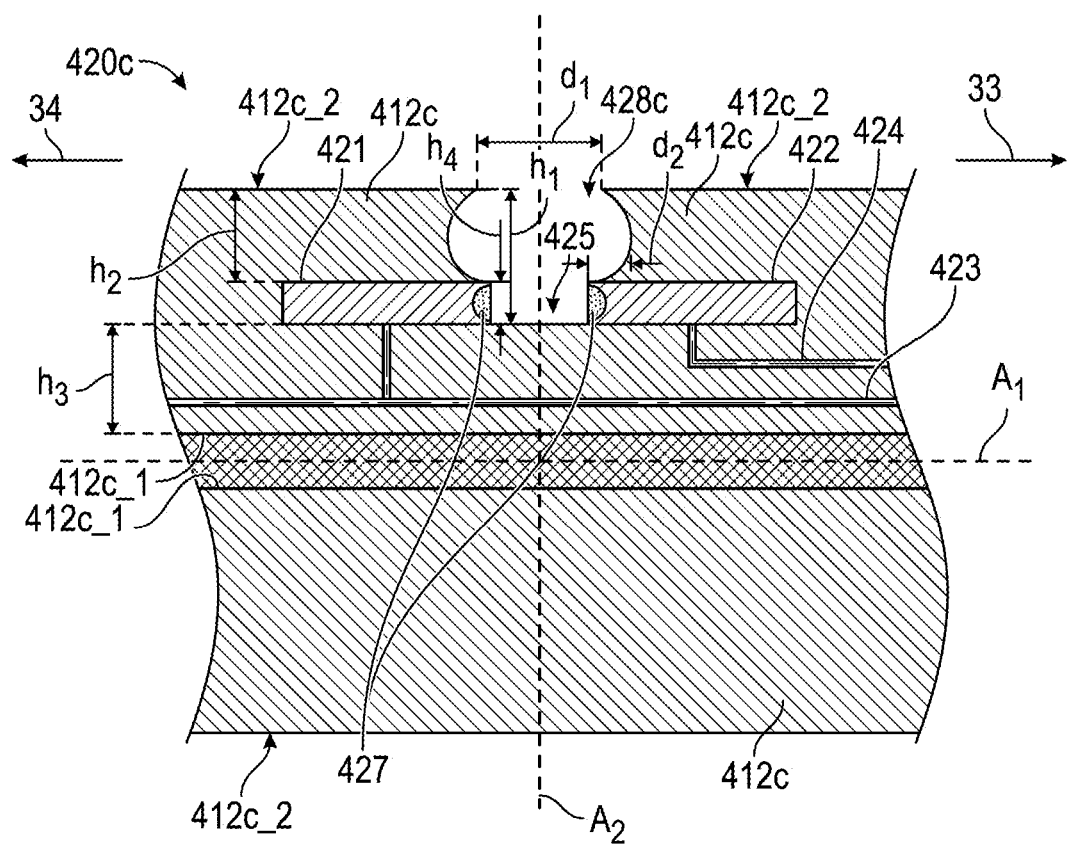

FIG. 4D illustrates an example electrode pair 420*c* having a notch 428*c* as part of a carrier 412*c*. The notch 428*c* can have a substantially concave sidewall on a proximal 33 and/or distal 34 end along a second axis A2. In some examples, a notch 428*c* can have a distance $d_1$ that is less than a distance of spark gap 425. In some examples, the distance $d_1$ can be greater than and/or the same as a distance of spark gap 425. In some examples, a carrier 412*c* can form a notch 428*c* by removing a portion of the outer surface 412*c*_2 as depicted in FIG. 4D.

Figure 4E:
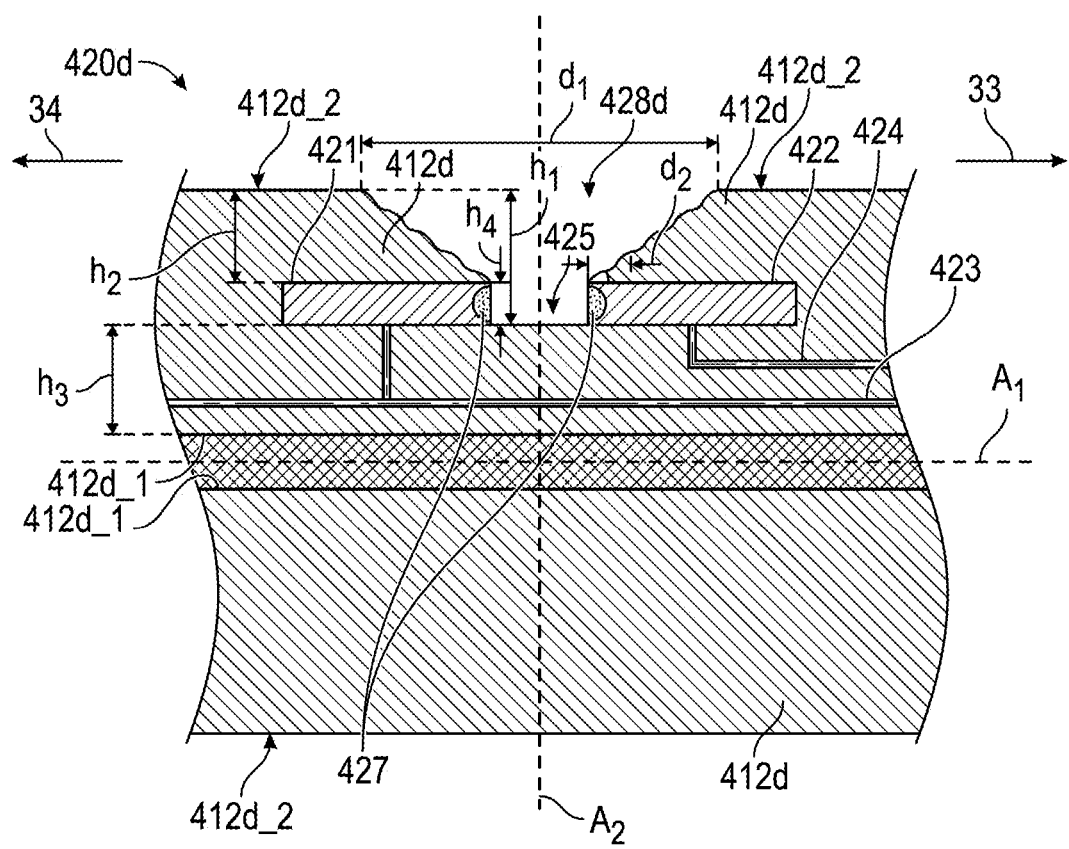

FIG. 4E illustrates an example electrode pair 420*d* having a notch 428*d* as part of a carrier 412*d*. In some examples, a notch 428*d* can have a distance $d_1$ along an outer surface 412*d*_2 that is greater than a distance of spark gap 425 and/or greater than a distance of the notch 428*d* proximate to an inner channel 412*d*_1. In some examples, the distance $d_1$ can be substantially greater than and/or approximately the same as a distance of spark gap 425 along an outer surface 412*d*_2. In some examples, a carrier 412*d* can form a notch 428*d* by removing a portion of the surface of the outer surface 412*d*_2. As depicted in FIG. 4E, a carrier 412*d* can form a notch 428*d* having a substantially angled sidewall on a proximal 33 and/or distal 34 end of a second axis A2.

As described above, a system (e.g., 100, 200A, 200B and/or the like) can include any combination of electrode pairs (e.g., 120, 220, 320, 320*a-d*, 420, 420*a-d* and/or the like) with one or more combinations of recessed channels and/or notches in a carrier to efficiently direct energy towards plaque of an artery. As an illustrative example, a system can include one recessed channel and/or one or more notches, each having one or more of the geometries as described herein.

FIGS. 5A-13B illustrate one or more example implementations of IVL catheters that may be used to modify calcified lesions in blood vessels. Each of the example implementations of an IVL catheter can include one or more features as described herein, to provide physicians with the ability to efficiently navigate one or more blood vessels to target and/or modify various accumulations of calcified lesions such as symmetrical and/or non-symmetrical calcified plaque.

FIGS. 5A-5F, 6, and/or 7 illustrate example implementations of an IVL catheter with conductive wires helically wound around a sheath and/or carrier. As a result of their helically wound conductive wires, IVL catheters of FIGS. 5A-5F, 6, and/or 7 have a reduced overall cross-sectional area and/or increased rigidity compared to other IVL catheter types, advantageously allowing a physician to navigate the IVL catheter through one or more arteries to access a greater number of locations including plaque.

Figure 5A:
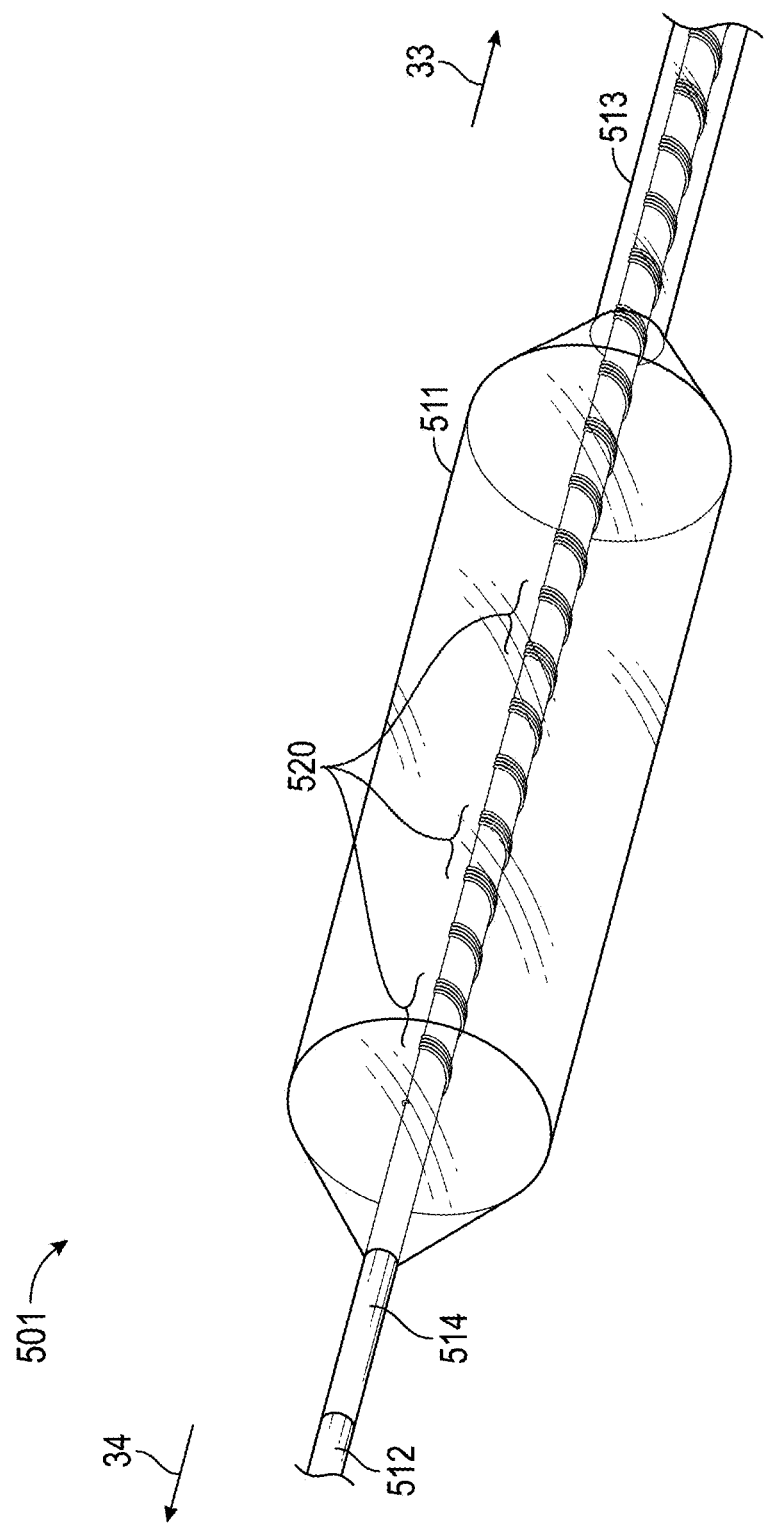
FIG. 5A illustrates an example perspective view of an IVL catheter with conductive wires helically wound around a carrier.
Figure 5B:
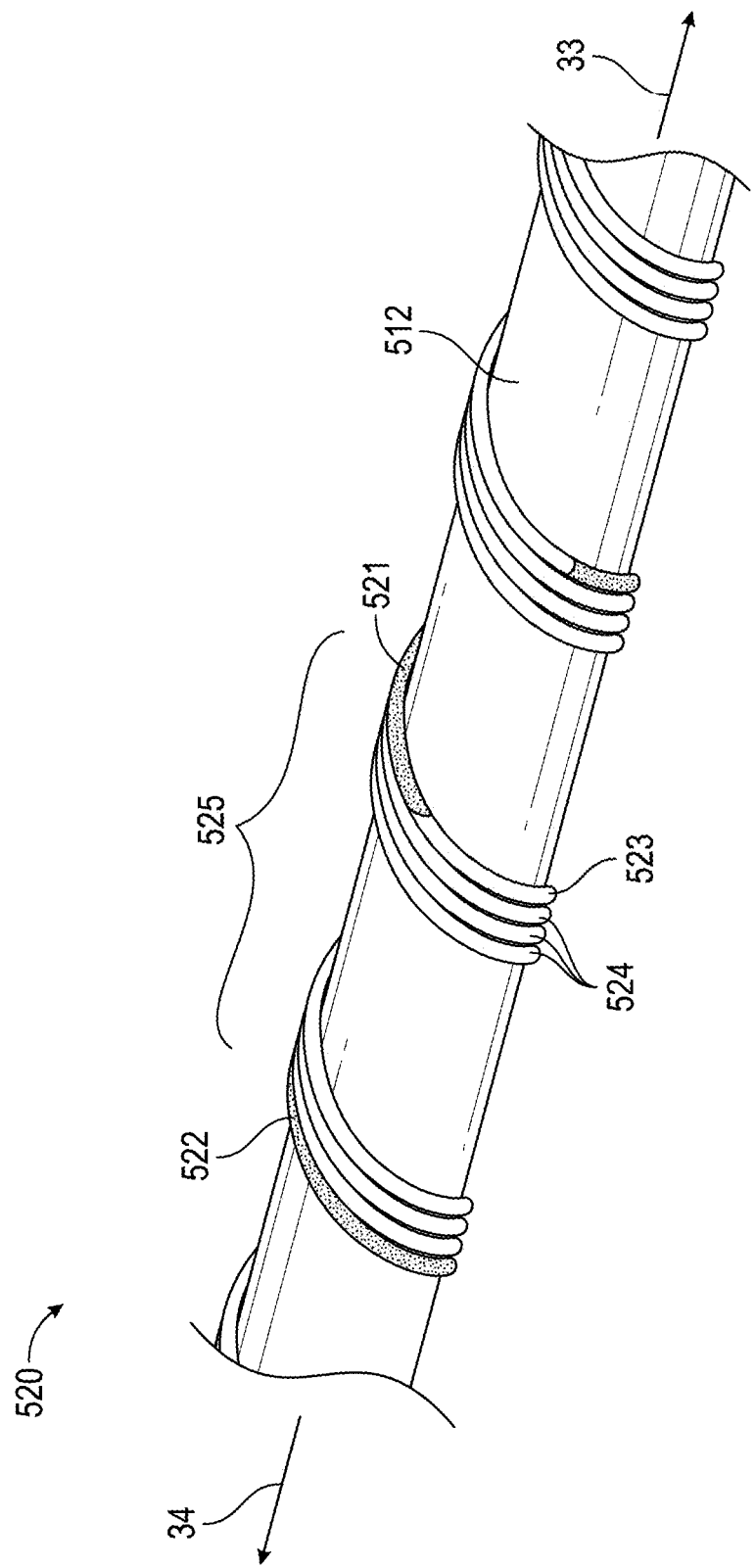
FIG. 5B illustrates an example perspective view of a conductive wire helically wound around a carrier.
Figure 5C:
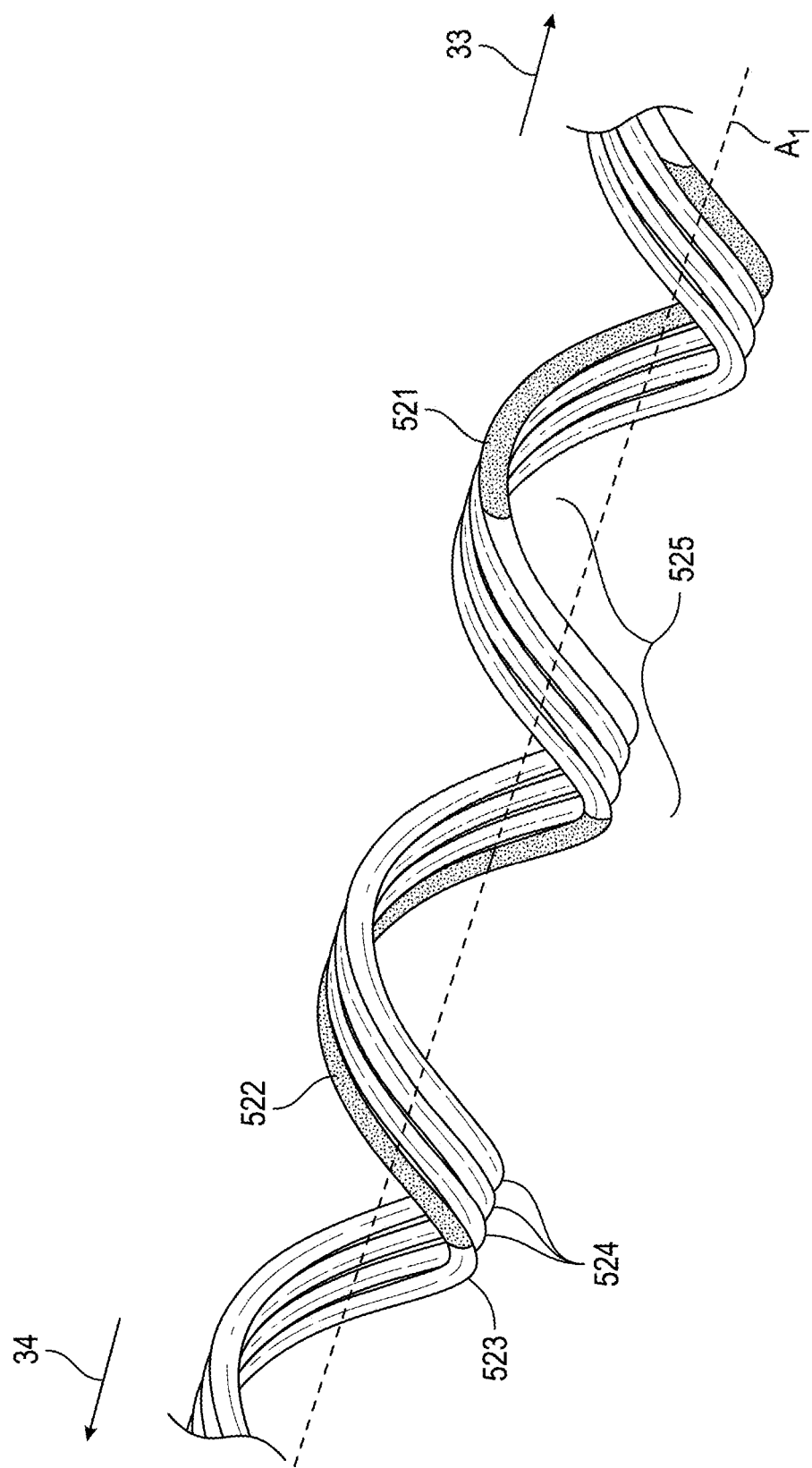
FIG. 5C illustrates an example perspective view of a helically wound conductive wire.

FIGS. 5A-5C illustrate example implementations of an IVL catheter 501 with conductive wires helically wound around a carrier. As depicted in FIG. 5A, IVL catheter 501 can include a balloon 511. A balloon 511 can be the same and/or similar to balloon 111 of FIG. 1. A balloon 511 can be scaled 514 at a distal end 34 and/or scaled 513 at a proximal end 33. An IVL catheter 501 can include a carrier 512. A carrier 512 can be similar and/or the same as carrier 112 and/or 312 of FIGS. 1, and/or 3 respectively. Further, IVL catheter 501 can include electrode pairs 520. Electrode pairs 520 can be the same and/or similar to electrode pair 320 of FIG. 3A. Balloon 511 can span a length of the IVL catheter 501 between 20 mm and 200 mm, between 20 mm and 150 mm, between 20 mm and 120 mm, between 20 mm and 100 mm, between 20 mm and 60 mm, between 40 mm and 150 mm, between 40 mm and 120 mm, between 60 mm and 120 mm, between 80 mm and 120 mm, between 100 mm and 150 mm, or any length therebetween. The length of the balloon 511 can be defined by the proximal and distal ends of the portion with the largest diameter. The diameter of the balloon 511 when inflated (e.g., the portion with the largest diameter), can be any length between 2 mm and 10 mm, such as 2 mm, 3 mm, 4 mm, 5 mm, 6 mm, 7 mm, 8 mm, 9 mm, or 10 mm.

As illustrated in FIGS. 5B-5C an electrode pair 520 can have four insulated conductive wires including wire 524 and/or wire 523. In some examples IVL catheter 501 can have more and/or less wires 523 and/or 524 depending on the desired number of electrode pairs 520 in IVL catheter 501. Wire 523 and/or 524 can be wrapped in a helical shape around a carrier 512 and/or along a first axis $A_1$. Advantageously, wrapping wire 523 and/or 524 a helical shape around carrier 512 and/or along a first axis $A_1$ can improve structural integrity while reducing the overall diameter of an IVL catheter 501. Further, an IVL catheter 501 can have increased flexibility at a distal end 34 in comparison to a proximal end 33 as the number of wires 523 and/or 524 can be reduced with each electrode pair 520. Thus, a flexible IVL catheter 501 can be allow physicians to navigate one or more blood vessels and/or cross occluded segments to reach a desired calcified lesion.

Wire 523 and/or 524 can be in electrical communication with, for example an energy generator 250 as illustrated in FIG. 2A-2B. Further, wire 523 and/or 524 can be, for example, a 36 AWG wire (e.g., copper wire insulated with one or more insulating materials). In some examples the gauge of wire 523 and/or 524 can be more and/or less than 36 AWG as described herein. In some examples, wire 523 can be a first wire gauge while wire 524 can be a second wire gauge.

Figure 6:
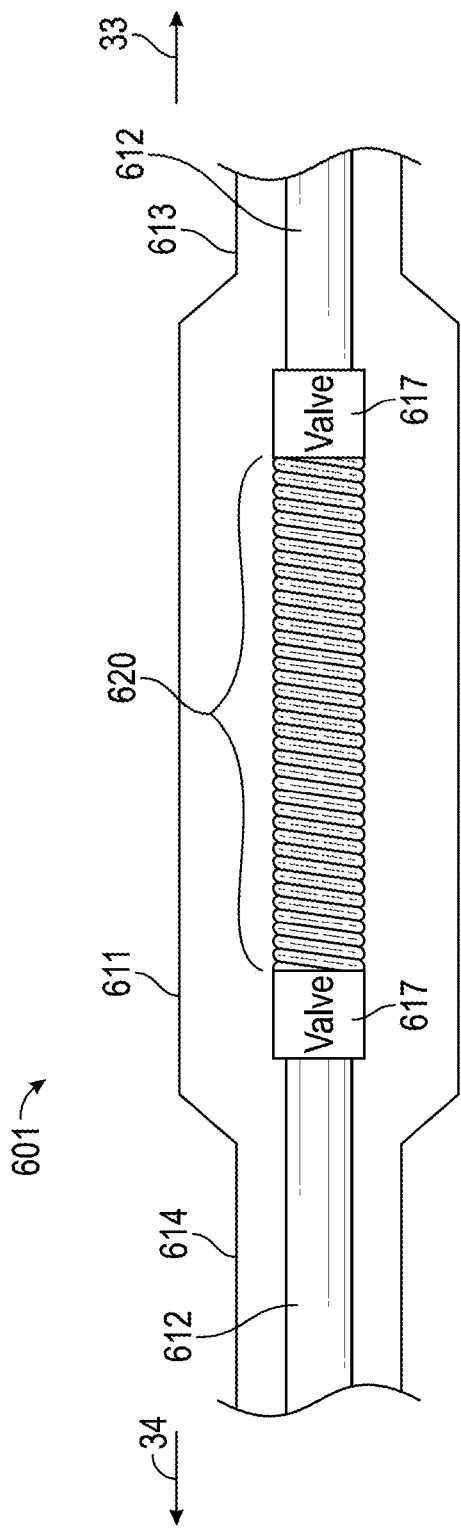
FIG. 6 illustrates an example implementation of an IVL catheter having one or more valves.

As further illustrated in FIG. 5C, electrode pair 520 can include a first electrode 521 and/or a second electrode 522. Electrodes 521 and/or 522 can be for example, a part of wire 523 and/or 524 including a portion where the insulation has been removed to expose a conductor. In some examples, the conductor can be copper wire. In some examples, electrodes 521 and/or 522 can be electrodes welded to the conductor of wire 523 and/or 524. Electrodes 521 and/or 522 can have a spark gap 525 therebetween. Spark gap 525 can be, for example, 1 mm. However, spark gap 525 can be wider and/or narrower depending on the configuration. For example, FIG. 6 depicts electrodes 521 and/or 522 wrapped around a carrier 512 such that a spark gap 525 exists axially and/or circumferentially along the carrier 512. In some examples, electrode 521 and/or 522 can be positioned proximally 33 and/or distally 34 along wire 523 and/or 524 to increase and/or decrease spark gap 525 as necessary.

In some implementations, the number of wires 523 and/or 524 can be reduced as one travels longitudinally from a proximal end 33 of a carrier 512 to a distal end 34 of the carrier 512 based on the number of electrode pairs 520 associated with IVL catheter 501 (e.g., an N+1 configuration as mentioned above). In one implementation, an IVL catheter 501 can include a common wire 524 and/or three source wires 523 at a proximal end of the IVL catheter 501. While traveling longitudinally toward a distal end 34 of the carrier 512, the number of wires 523 and/or 524 can be reduced to three (e.g., one common wire 524 and/or two source wires 523) as a first source wire 523 may be terminated at an electrode pair 520. Consequently, a most distal 34 electrode pair 520 requires two wires to form an electrode pair 520; a common wire 524 and/or a source wire 523.

Figure 5D:
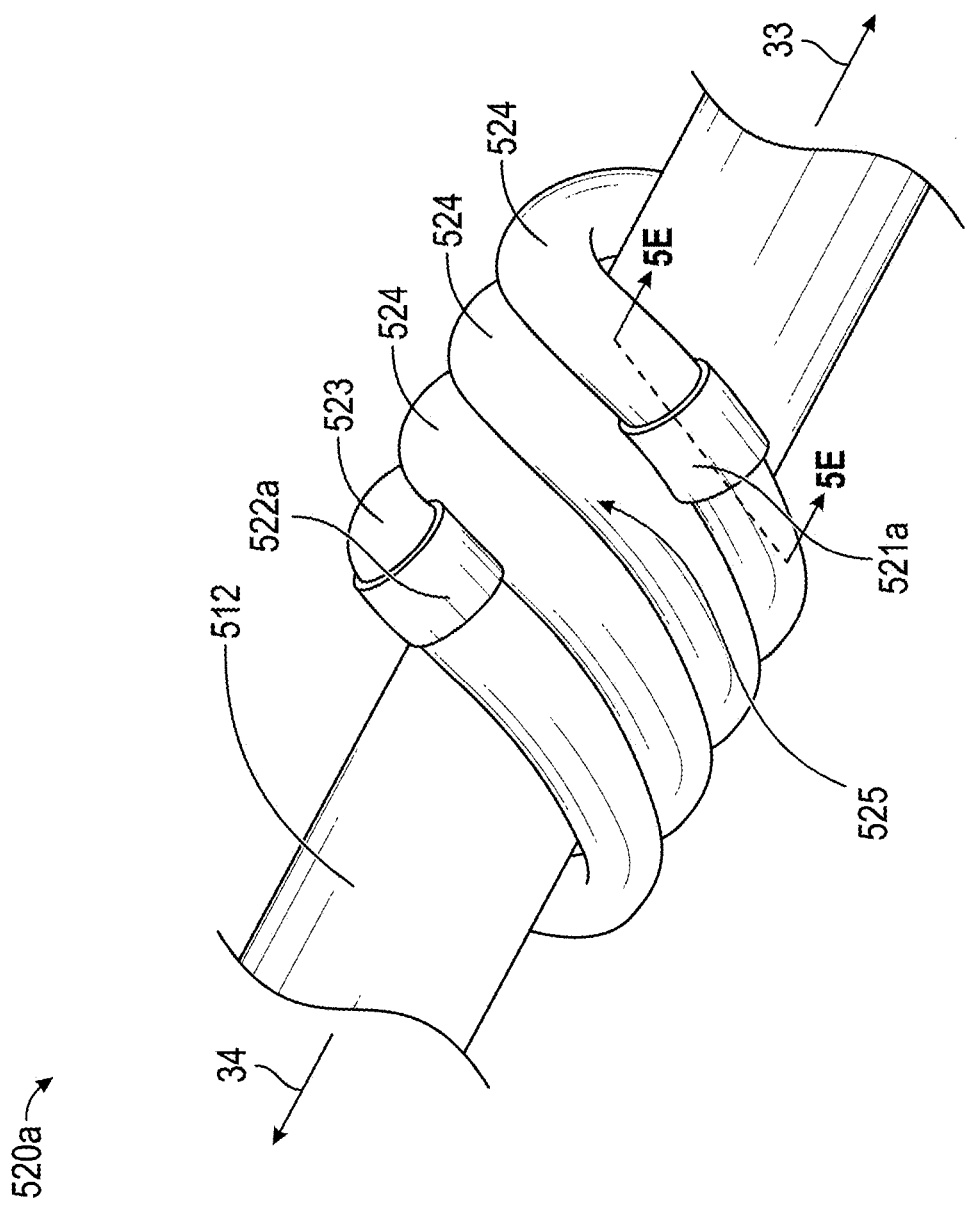
FIG. 5D illustrates an example implementation of ring electrodes as part of a helically wound electrode pair.
Figure 5E:
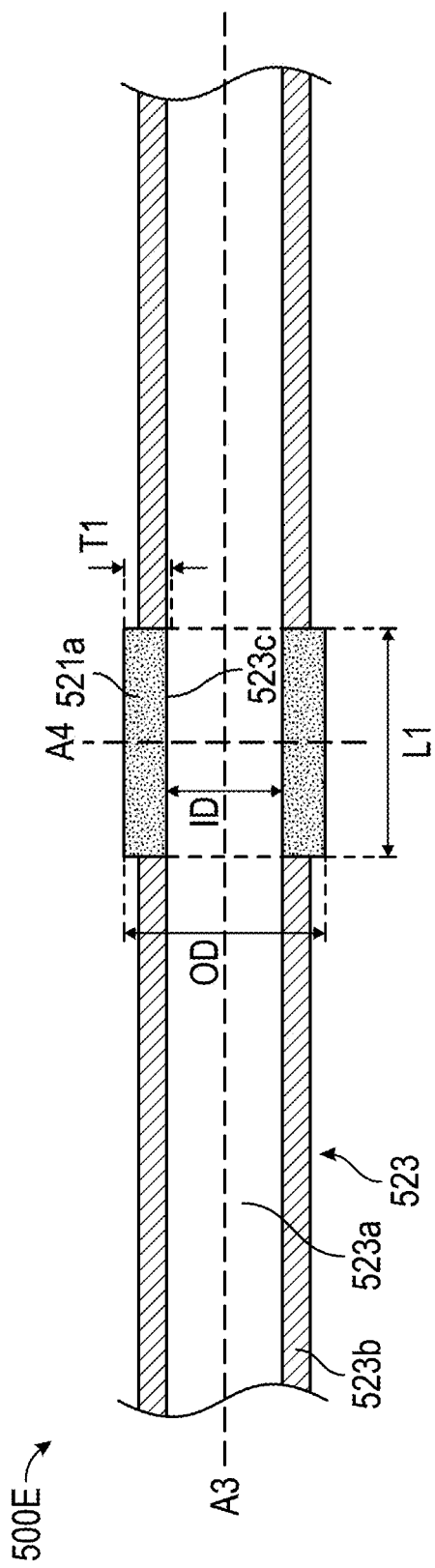
FIG. 5E illustrates a cross-sectional view of a conductive wire and a ring electrode.

FIGS. 5D-5E illustrate example implementations of ring electrodes 521a, 522a as part of an electrode pair 520a. An electrode pair 520a may include a combination of ring electrodes 521a, 522a and/or another type of electrode (e.g., electrodes 321, 322, 421, 422, 521, 522, and/or the like). Advantageously, ring electrodes 521a, 522a used as part of an IVL catheter 101, 201A, 201B, 501 (and/or another IVL catheter as described herein) can increase the lifespan and usefulness of an IVL catheter during a procedure in comparison to conventional IVL catheters. For example, a conventional IVL catheter as described above may limit the number of pulses a physician may emit (e.g., a cycle count), as electrical arcing occurring during each pulse may slowly degrade and/or erode the surface of an electrode within an electrode pair. In some cases, a physician may be limited to 300 pulses during a procedure with conventional IVL catheters. Pulse limitations may result in "pulse rationing," where a physician elects to limit a number of pulses for a first calcified lesion, regardless of the effectiveness of the pulses on the first calcified lesion, in order to conserve pulses for subsequent calcified lesions. Physicians may pulse ration to reduce the number of procedures a patient may endure, reduce costs associated with replacing an IVL catheter during a procedure, and/or as covered by a patient's medical insurance.

Ring electrodes 521a, 522a, alone or in combination with one or more features described herein may achieve cycle counts far beyond 300 pulses, thereby increasing the longevity and reliability of an IVL catheter and improving outcomes for patients and physicians alike. For example, ring electrode 521a, 522a may have a larger surface area than other electrode types which may disperse erosion and/or pitting events along a larger surface. Additionally, ring electrodes 521a, 522a may uniformly distribute an electric field in comparison to other electrode types, thereby improving electroporation when for example, a balloon 111 of FIG. 1, is coated with a type of medication designed to permeate into the cell membrane at a treatment site.

Ring electrodes 521a, 522a can be electrically coupled to an exposed conductor of wires 523, 524, to create an electrode pair 520a. One or more ring electrodes 521a, 522a may operate along with another type of electrode and/or type of electrode pair described herein (e.g., 120, 220, 320, 420 and/or the like) to generate a spark along a spark gap 525.

Ring electrodes 521a, 522a may include any of, and/or a combination of gold, platinum, platinum-iridium alloy, stainless steel, a nickel-titanium alloy, a copper alloy, tungsten, and/or the like. In some examples, ring electrodes 521a, 522a may be approximately 45% nickel and/or approximately 50% copper.

FIG. 5E illustrates a cross-section 500E of wire 523 that includes a ring electrode 521a encircling wire 523. FIG. 5E is described with reference to wire 523 and/or ring electrode 521a of an electrode pair 520a, however the description herein may interchangeably and/or equally apply to wires 524 and/or ring electrodes 522a of an electrode pair 520a. As illustrated in FIG. 5E, wire 523 can include a conductor 523a and an insulator 523b. The conductor 523a can be any suitable conductive material, such as copper, silver, gold, platinum, an alloy and/or the like. An insulator 523b can include any suitable insulator for IVL catheters and/or the like.

Ring electrode 521a may include an inner surface electrically coupled to an exposed portion 523c of wire 523. For example, ring electrode 521a may fully and/or partially surround, enclose, encircle, and/or the like, wire 523, to form a ring and/or a partial ring around wire 523 and/or around an exposed portion 523c of wire 523. Ring electrode 521a may be soldered, crimped, welded, or adhesively bonded to an exposed portion 523c of wire 523. Ring electrode 521a may have a minimum thickness $T_1$ as measured radially from a center axis $A_3$ and/or as measured along a radial axis $A_4$ of a wire 523, 524. A minimum thickness of a ring electrode 521a may be approximately 0.001" to 0.002", however ring electrode 521a may have any thickness (e.g., 0.0001", 0.001", 0.01", 0.1" and/or the like). Ring electrode 521a may have a minimum length $L_1$ as measured longitudinally along a center axis $A_3$. In some examples, a minimum length $L_1$ is 1 mm, however the minimum length may be more and/or less than 1 mm (e.g., 0.01 mm, 0.1 mm, 0.98 mm, 1.2 mm, 2.0 mm and/or the like). Additionally, an inner diameter ID and/or outer diameter OD of a ring electrode 521a may be measured radially from a center axis $A_3$. In some examples, the inner diameter ID and/or outer diameter OD of a ring electrode 521a may be larger than, smaller than, and/or between the inner diameter and/or outer diameter of a wire 523 (e.g., conductor 523a and insulator 523b), and/or a portion of a conductor 523a and/or insulator 523b.

Figure 5F:
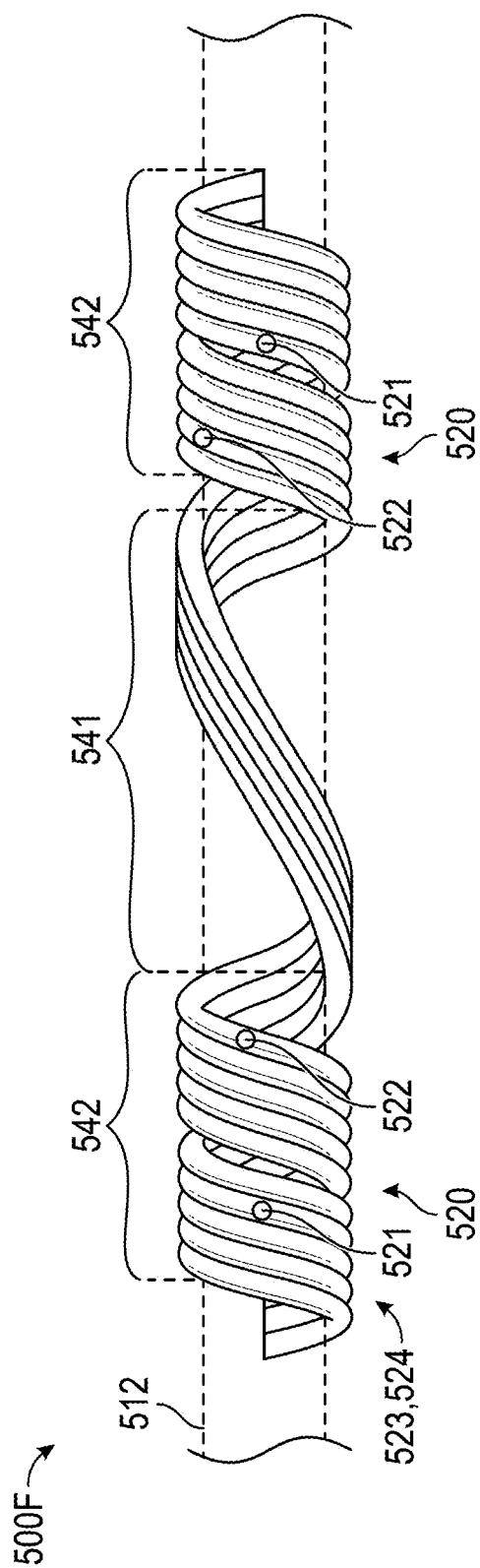
FIG. 5F illustrates an example implementation of an IVL catheter with variable-pitch helically wound insulated wires.

FIG. 5F illustrates an example implementation of a variable-pitch helically wound coil 500F of insulated wires. A coil 500F may be wound around a carrier 112, 512 and/or the like, as part of an IVL catheter 501. Optionally and/or alternatively, conductive wires 523, 524 may have a varying pitch as the conductive wires 523, 524 are wound along a carrier 512. For example, a pitch of helically wound wires 523, 524 can be tightly wound 542 near an electrode pair 520 and/or loosely wound 541 at another location along the carrier 512, such that a physician may determine the position of an electrode pair 520 by utilizing fluoroscopy, x-ray, and/or the like. In some examples, a coil 500F at and/or near an electrode pair 520 may be tightly wound 542, such that the wires 523, 524 are touching and/or close to touching one another as depicted in FIG. 5F. In some examples, a helically wound coil 500F may be loosely would 541 (e.g., spaced apart longitudinally) at another location along a carrier 512. Consequently, tightly wound 542 wires may be identified (e.g., via fluoroscopy and/or the like) by a physician during a procedure, to indicate an approximate location of an electrode pair 520, a spark gap 525, and/or electrodes 521, 522, within a blood vessel. Additionally and/or alternatively, tightly wound 542 wires 523, 524 may provide structural support at and/or near electrode pairs 520. In some cases, tightly wound 542 wires may increase the rigidity and ultimately the effectiveness of sonic waves electrode from an IVL catheter 501. Additionally and/or optionally, a marker (such as marker 116 of FIG. 1) may be positioned at and/or near an electrode pair 520, to indicate the position of electrode pairs 520 to a physician during a procedure.

FIGS. 6 and/or 7 illustrate example implementations of IVL catheters 601 and/or 701 with conductive wires helically wound around a carrier and/or one or more valves. Advantageously, an IVL catheter 601 and/or 701 with valves can be used by physicians to continuously flush conductive fluid through the IVL catheter 601 and/or 701, to maintain a specified pressure within the IVL catheter and/or to remove heat generated by one or more electrical arcs generated inside the IVL catheter. Thus, IVL catheters 601 and/or 701 can allow a physician to execute a procedure without interruption due to deflating and/or inflating a catheter 601 and/or 701 due to excessive heat accumulation in an artery.

FIG. 6 illustrates an IVL catheter 601 including a balloon 611. A balloon 611 can be the same and/or similar to balloon 111 of FIG. 1. A balloon 611 can be sealed 614 at a distal end 34 and/or sealed 613 at a proximal end 33. An IVL catheter 601 can include a carrier 612. A carrier 612 can be similar and/or the same as carrier 112 and/or 312 of FIGS. 1, and/or 3 respectively. Further, IVL catheter 601 can include electrode pairs 620. Electrode pairs 620 can be the same and/or similar to electrode pair 320 of FIG. 3A. Electrode pairs 620 can be positioned, for example, along and/or beneath the surface of a carrier 612 and/or between valves 617 as depicted in FIG. 6.

Additionally and/or alternatively, IVL catheter 601 can include valves 617. Valves 617 can act as an inlet and/or an outlet for conductive fluid. In some implementations, valves 617 can be positioned longitudinally along a carrier 612 as depicted in FIG. 6. An IVL catheter 601 can flush a balloon 611 with conductive fluid via valves 617, to maintain a specified pressure within the balloon 611. In some implementations, IVL catheter 601 can be configured to flush a balloon 611 with conductive fluid via valves 617, to dissipate heat within an IVL catheter 601 caused by, for example, one or more electrical arcs generated across a spark gap. Additionally, an IVL catheter 601 configured with valves 617 may remove particulates generated during an electrical by flushing conductive fluid through the IVL catheter 601.

Figure 7:
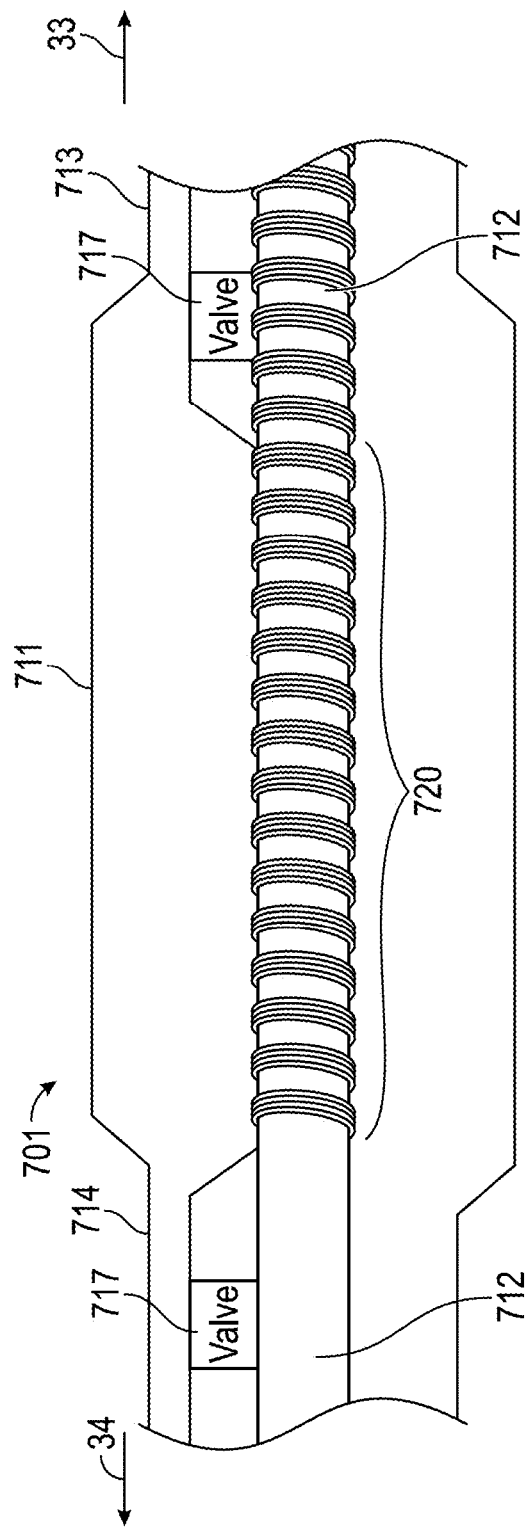
FIG. 7 illustrates an example implementation of a an IVL catheter having one or more valves.

FIG. 7 illustrates an IVL catheter 701 including a balloon 711. A balloon 711 can be the same and/or similar to balloon 111 of FIG. 1. A balloon 711 can be scaled 714 at a distal end 34 and/or scaled 713 at a proximal end 33. An IVL catheter 701 can include a carrier 712. A carrier 712 can be similar and/or the same as carrier 112 and/or 312 of FIGS. 1 and/or 3 respectively. Further, IVL catheter 701 can include electrode pairs 720. Electrode pairs 720 can be the same and/or similar to electrode pair 320 of FIG. 3A. Electrode pairs 720 can be positioned, for example, along and/or beneath the surface of a carrier 712. Additionally, electrode pair 720 can be helically wound towards a proximal end 33 as depicted in FIG. 7.

Additionally and/or alternatively, IVL catheter 701 can include valves 717. Valves 717 can act as an inlet and/or an outlet for conductive fluid. In some implementations, valves 717 can be outside a carrier 712 as depicted in FIG. 7. An IVL catheter 701 can flush a balloon 711 with conductive fluid via valves 717, to maintain a specified pressure within the balloon 711. In some implementations, IVL catheter 701 can be configured to flush a balloon 711 with conductive fluid via valves 717, to dissipate heat within an IVL catheter 701 caused by, for example, one or more electrical arcs generated across a spark gap. Additionally, an IVL catheter 701 configured with valves 717 may remove particulates generated during an electrical by flushing conductive fluid through the IVL catheter 701.

Figure 8A:
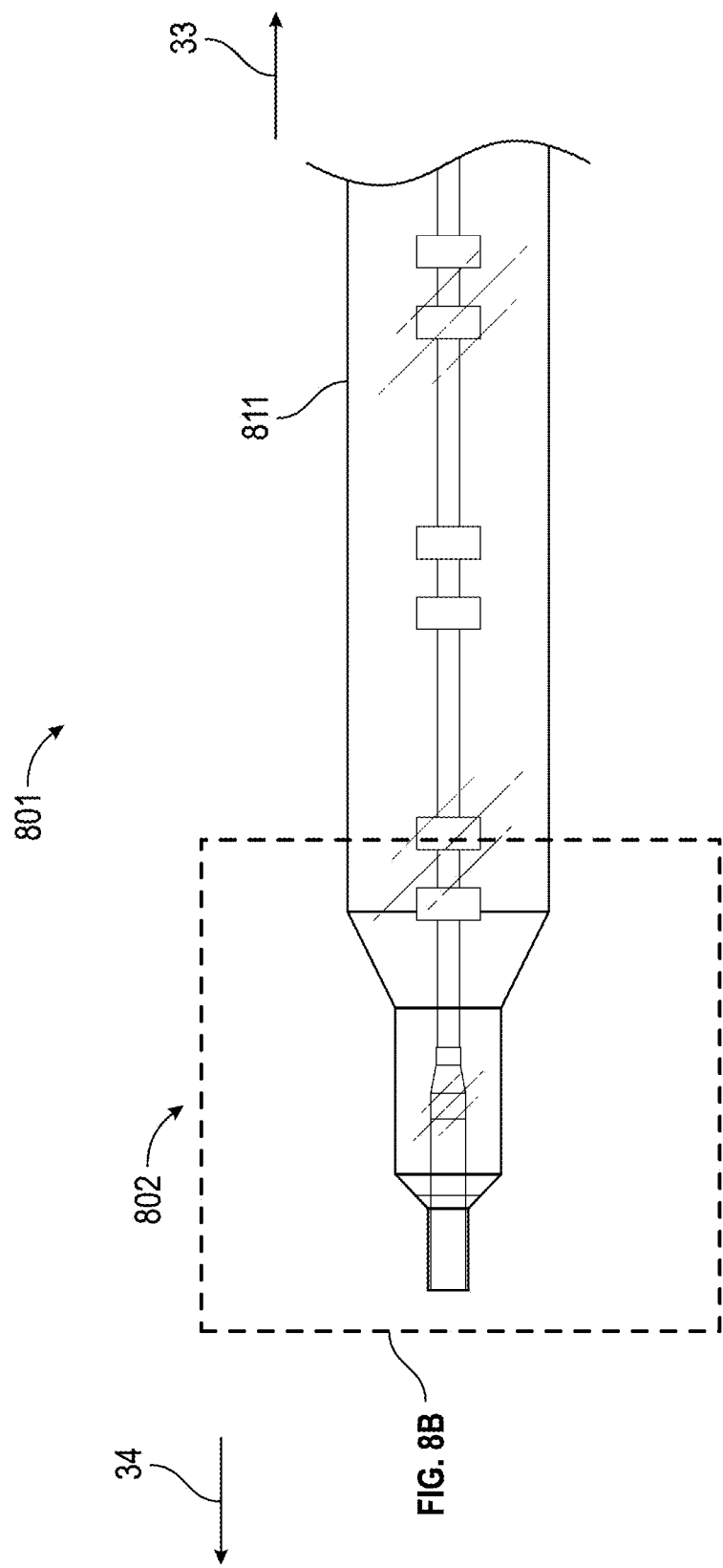
FIG. 8A illustrates an example implementation of a CTO IVL catheter.
Figure 8B:
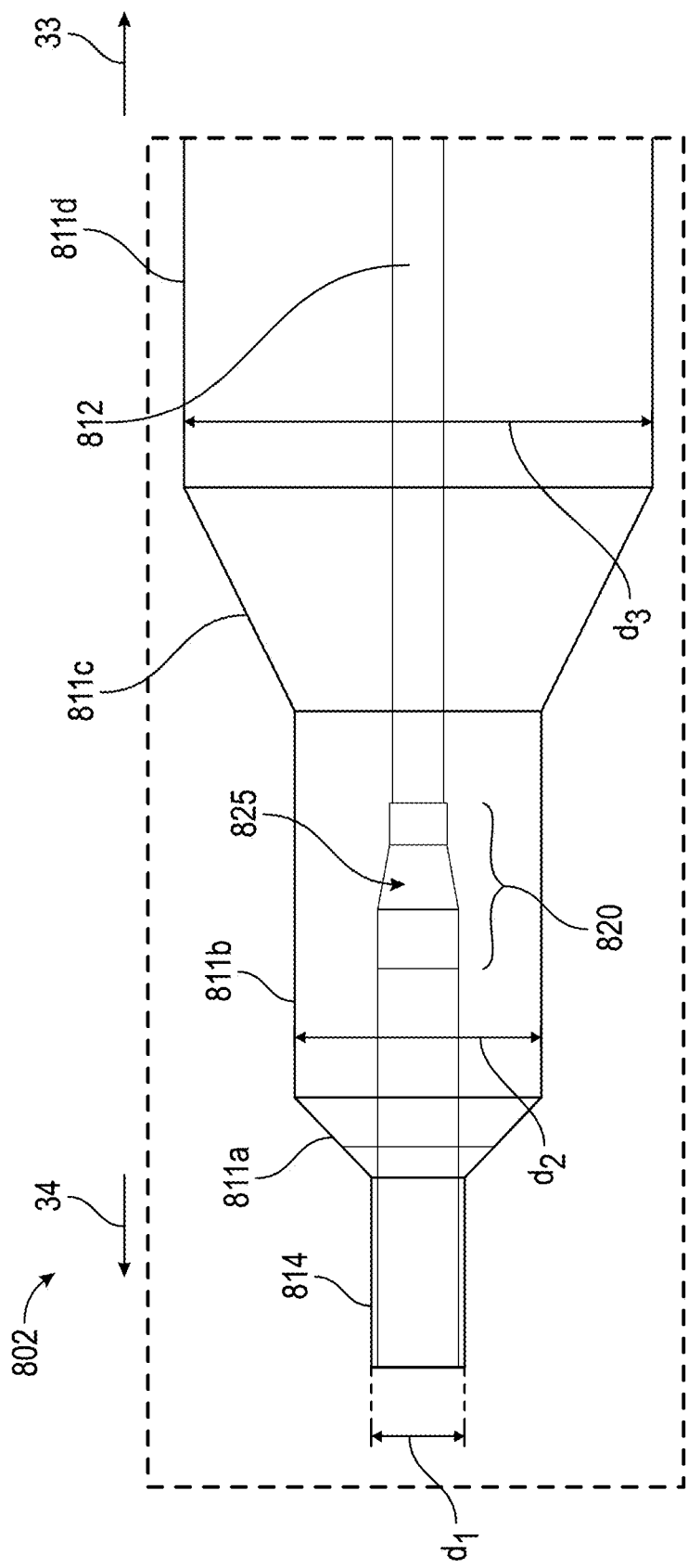
FIG. 8B illustrates an example implementation of a distal end of a CTO IVL catheter.

FIGS. 8A-8B illustrate an example implementation of a Chronic Total Occlusion (CTO IVL) catheter 801 that may be used to treat a partially and/or fully occluded segment of a blood vessel by selectively transmitting sonic waves to one or more areas including calcified lesions. For example and as illustrated in FIG. 8A, catheter 801 can treat the occluded segment using an extension 802 at a distal 34 end of the catheter 801. An extension 802 can efficiently treat an occluded segment by selectively emitting sonic waves at a distal end of catheter 801. Sonic waves can break calcium lesions into smaller pieces, causing a blood vessel to open. Eventually, blood vessels may open enough to allow a catheter 801 to cross an occluded segment. Thus catheter 801 can significantly reduce procedure times and/or increase range of locations accessible by catheter 801 as one catheter can be used to modify and/or cross a partially and/or fully occluded segment.

As illustrated in FIG. 8B, extension 802 portion of catheter 801 can include a carrier 812. A carrier 812 can be similar to and/or the same as carrier 112. A carrier 812 may have a hollow and/or solid core. In some examples, a carrier 812 can terminate at a distal end 34 via a seal 814. A seal 814 can be configured to keep saline within balloon 811. A balloon 811 can vary in shape from a proximal end to a distal end 34. For example, a balloon 811a can be tapered from a seal 814 at a distal end, having a first diameter $d_1$ to a proximal end having a second diameter $d_2$. In some examples, a first diameter $d_1$ can be approximately 0.5 mm. In some examples a first diameter $d_1$ can be more and/or less than 0.5 mm (e.g., 0.01, 0.1, 1, 2, 3, etc.). In some examples, a second diameter $d_2$ can be approximately 1 mm. In some examples a second diameter $d_2$ can be more and/or less than 1 mm (e.g., 0.01, 0.1, 1, 2, 3, etc.). A balloon 811b can have a continuous diameter from a distal end to a proximal end. In some examples, the diameter of balloon 811b can be the same and/or similar to diameter $d_2$ as described above. A balloon 811c can be tapered from a distal end, having a second diameter $d_2$ to a proximal end having a third diameter $d_3$. In some examples, a second diameter $d_2$ can be approximately 1 mm. In some examples a second diameter $d_2$ can be more and/or less than 1 mm (e.g., 0.01, 0.1, 1, 2, 3, etc.).

In some examples, a third diameter $d_3$ can be approximately 2 mm. In some examples a third diameter $d_3$ can be more and/or less than 2 mm (e.g., 0.01, 0.1, 1, 2, 3, 4, 5, etc.). A balloon 811d can have a continuous diameter from a distal end to a proximal end. In some examples, the diameter of balloon 811d can be the same and/or similar to diameter $d_3$ as described above. In some examples, balloon 811a, 811b, 811c, and/or 811d can be in fluid communication (e.g., one balloon 811) and/or separate balloons 811a, 811b, 811c, and/or 811d.

Advantageously, during treatment, a seal 814 can contact a partially and/or fully occluded segment in order to modify calcified lesions. A carrier 812 can further support one or more electrode pairs 820 located near a distal end 34 of an extension 802. Electrode pair 820 can be the same and/or similar to any of the electrode pairs described herein, such as electrode pairs 120, 220, 320, 420, 520, 520a, and/or the like. Electrode pair 820 can be configured to emit sonic waves axially towards a distal end 34 of a catheter 801, radially, and/or in another direction to cause a seal 814 and/or balloon 811 to fracture plaque based on spark gap 825. Additionally and/or optionally, there may be one or more electrode pairs 820 distributed proximally 33 along a carrier 812 as illustrated in FIG. 8A and/or as illustrated in FIGS. 1, 2, and/or 5.

In some examples, electrode pair 820 can be connected to energy generator 150 and/or 250 as described in FIGS. 1-2 respectively. Advantageously, a catheter 801 in electrical communication with an energy generator 150 and/or 250 can allow a physician to selectively generate an arc in electrode pair 820 at a distal end 34, creating sonic waves that can target plaque at a specific location while avoiding emitting sonic waves at one or more additional location within a blood vessel.

Figure 9A:
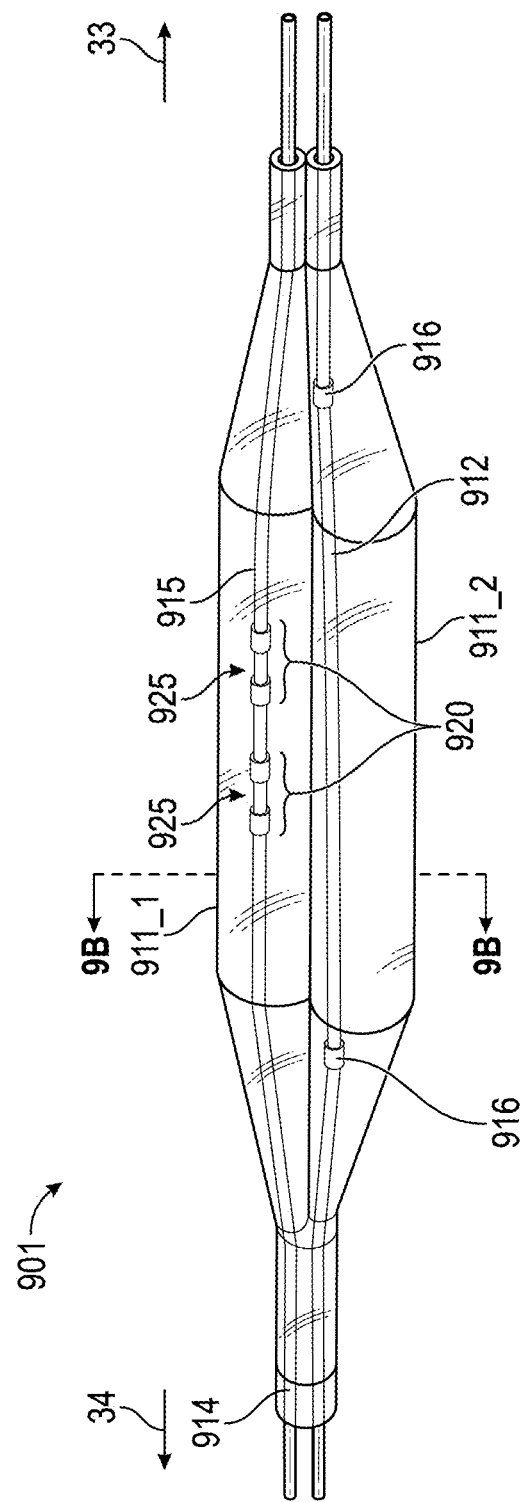
FIG. 9A illustrates an example perspective view of a dual-balloon IVL catheter.
Figure 9B:
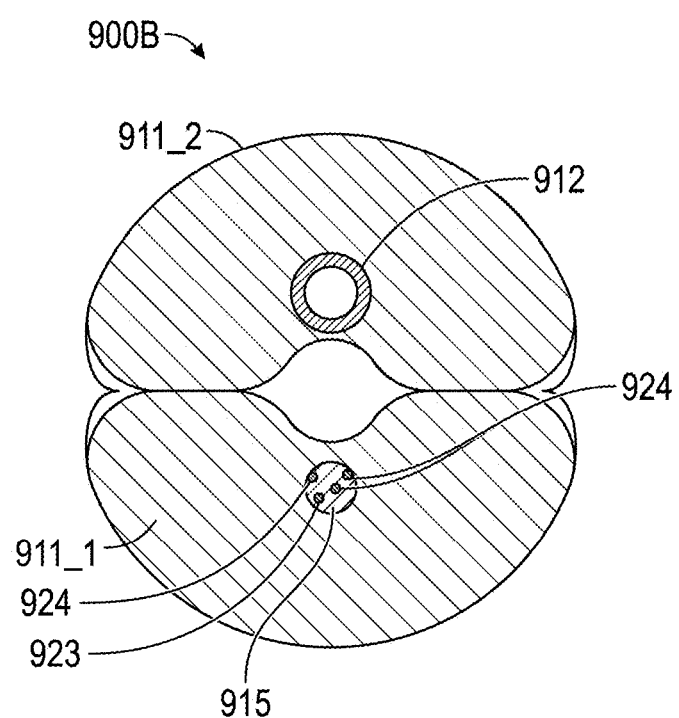
FIG. 9B illustrates an example cross-sectional view of a dual balloon IVL catheter.
Figure 9C:
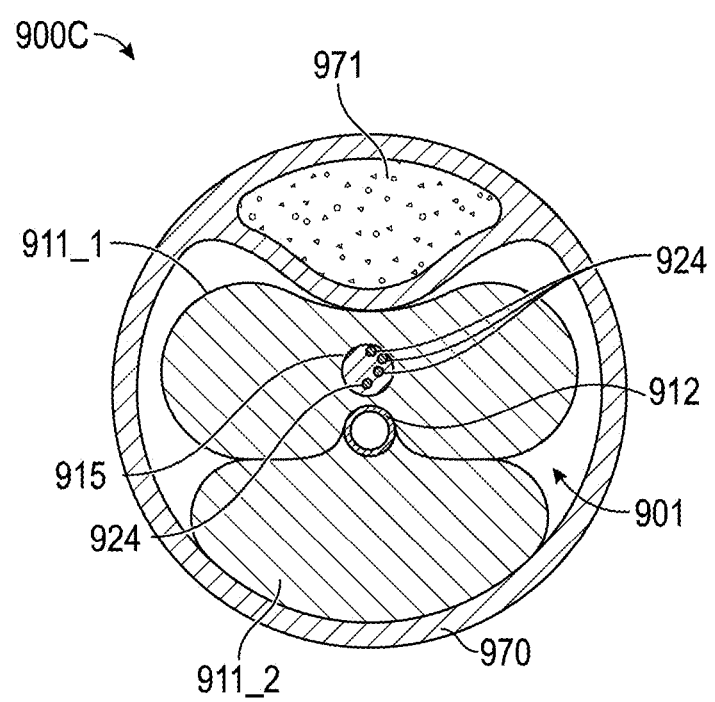
FIG. 9C illustrates an example cross-sectional view of a dual balloon IVL catheter in a blood vessel.

FIGS. 9A-9C illustrate an example implementation of a dual balloon IVL catheter 901. As illustrated in FIG. 9A, catheter 901 can include a first balloon 911_1. A first balloon 911_1 can be scaled to a first carrier 915 via seal 914. A first carrier 915 can be, for example a solid core carrier as described with reference to carrier 112 and/or 312 of FIGS.

1, and/or 3 respectively. In some implementations, a first carrier 915 can be a conduit for one or more conductive wires (e.g., a hollow core), solid, and/or a lumen to support conductive fluid exchange. Conductive wires (e.g., wires) can be, for example inside a first carrier 915 and/or on the surface of a first carrier 915 as depicted in FIGS. 9B-9C. A first carrier 915 can be used to support one or more electrode pairs 920. Electrode pairs 920 can each have a spark gap 925. Electrode pairs 920 can be the same and/or similar to one or more configurations of electrode pairs 120, 220, 320, 420, and/or the like as described herein. Catheter 901 can further include a second balloon 911_2. A second balloon 911_2 can be adjacent to a first balloon 911_1. A second balloon 911_2 can include a second carrier 912 therethrough. A second carrier 912 can be the same as and/or similar to carrier 112 and/or 312 of FIGS. 1, and/or 3 respectively as described herein. In some implementations, balloon 911_1 and/or 911_2 are two separate balloons. In some implementations, balloon 911_1 and/or 911_2 share a common wall between the two balloons (e.g., one balloon having two separate chambers). In some examples, a first balloon 911_1 and/or a second balloon 911_2 can be in fluid communication with one another. In some examples, a first balloon 911_1 and/or a second balloon 911_2 may not be in fluid communication with one another. Balloons 911_1 and/or 911_2 may be filled with saline and/or another liquid. In some examples, catheter 901 can include markers 916. In some examples, a physician can use markers 916 under fluoroscopic guidance to ensure that a first balloon 911_1 is positioned to face plaque. Advantageously, a dual balloon IVL catheter 901 implementation can be utilized, along with one or more features as described herein, to directionally control and/or amplify one or more sonic waves as generated by electrode pairs 920.

FIG. 9B depicts a cross section 900B of catheter 901 while FIG. 9C depicts a cross section of a blood vessel 900C with catheter 901 inserted therethrough. As illustrated in FIGS. 9B and/or 9C, a first carrier 915 can include wires 923 and/or 924. Wires 923 and/or 924 can be the same and/or similar to wires 123, 124, 223 and/or 224 of FIGS. 1, 2A, and/or 2B. Wires 923 and/or 924 are depicted as inside a first carrier 915 and/or on the surface of the first carrier 915, however, wires 923 and/or 924 can be located at another position. In some implementations, wires 923 and/or 924 are all located within a first carrier 915 while in some implementations one or more wires 923 and/or 924 are located on the surface of the first carrier 915. Catheter 901 may be used by physicians to efficiently modify non-symmetrical plaque 971 in a blood vessel wall 970. For example, a first balloon 911_1 can include one or more electrode pairs 920 configured to generate sonic waves while a second balloon 911_2 is configured to reflect sonic waves generated by electrode pair 920 back towards plaque 971. A physician can position catheter 901 such that balloon 911_1 is closest to non-symmetrical plaque 971. Once a catheter 901 is in position, sonic waves generated by electrode pair 920 can directionally target non-symmetrical plaque 971. Because a second balloon 911_2 reflects the sonic waves generated by electrode pair 920, plaque 971 receives an initial energy from the sonic wave and/or a reflected energy from balloon 911_2. Thus, a dual balloon IVL catheter 901 design may efficiently treat calcified lesions by directionally controlling sonic waves emitted from electrode pair 920. Further a dual balloon IVL catheter 901 can reduce the risk of harming areas of a blood vessel wall 970 because a second balloon 911_2 may act as a barrier, blocking emitted energy from an opposite side of the blood vessel wall 970.

Figure 10:
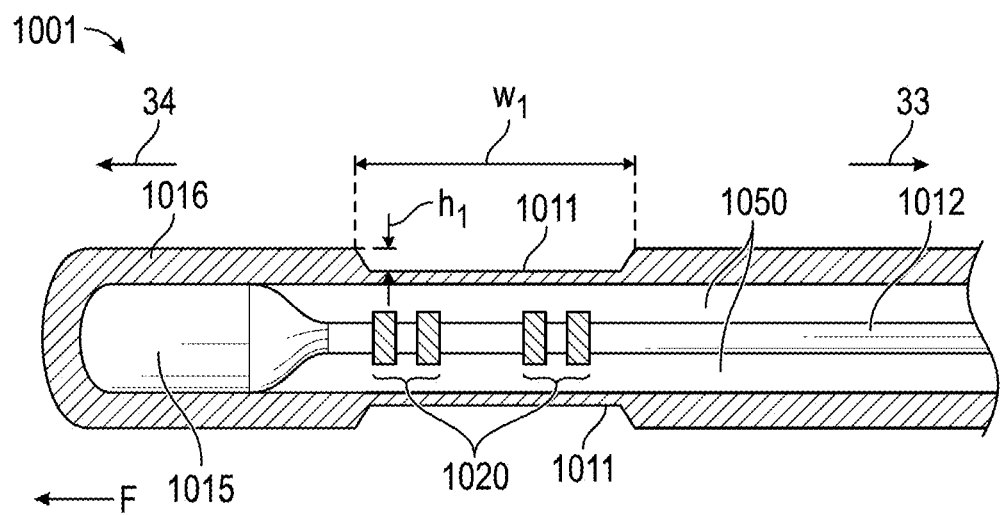
FIG. 10 illustrates an example implementation of a balloon-less IVL catheter.
Figure 11:
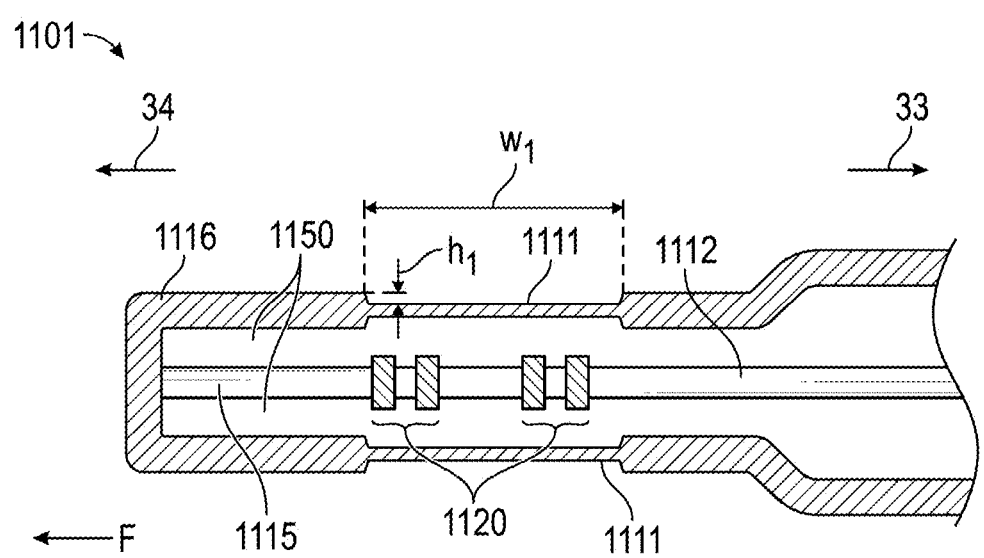
FIG. 11 illustrates an example implementation of a balloon-less IVL catheter.

FIGS. 10-11 illustrate example implementations of balloon-less IVL catheter 1001 and/or 1101 respectively. Catheter 1001 and/or 1101 can effectively and/or efficiently open a partially and/or fully occluded blood vessel, to restore flow while reducing complications, by concentrating energy at a distal end of the catheter 1001 and/or 1101.

As depicted in FIG. 10, catheter 1001 can include a thin membrane 1011, a shaft 1015, and/or a distal membrane 1016. Catheter 1001 can further include a carrier 1012, having electrode pairs 1020 and/or a cavity 1050. Electrode pairs 1020 can be the same and/or similar to electrode pairs 120, 220, 320, 420, and/or the like as described herein. One or more electrode pairs 1020 can be located at a distal end 34 of catheter 1001, such that sonic waves are concentrated at the distal end 34. Cavity 1050 between a thin membrane 1011 and/or a carrier 1012 can be filled with, for example saline and/or another solution such as contrast. In some examples thin membrane 1011 can be flexible enough to navigate through one or more blood vessels, including crossing partially occluded lesions.

In some examples, a thin membrane 1011 can have a recessed portion. In some examples a recessed portion of thin membrane 1011 can have a width $w_1$ of approximately 1 mm. In some examples a width $w_1$ can be more and/or less than 1 mm (e.g., 0.01, 0.1, 2, 5, 10 and/or the like). In some examples a recessed portion of thin membrane 1011 can have a height $h_1$ of approximately 0.5 mm. In some examples a height $h_1$ of thin membrane 1011 can be more and/or less than 0.5 mm (e.g., 0.001, 0.01, 0.1, 1, 1.5, 3 and/or the like).

In some implementations, a shaft 1015 and/or a distal membrane 1016 can be used to modify calcified lesions that may be difficult for another type of catheter to cross. For example, electrode pair 1020 can concentrate sonic waves at a distal end 34 of a catheter 1001, where the sonic waves travel through a saline solution in cavity 1050 to a shaft 1015, and/or then to a distal membrane 1016. Consequently, a shaft 1015 and/or a distal membrane 1016 can transfer energy from the sonic waves as a mechanical force "F" as depicted in FIG. 10, to modify a calcified lesion, such that a larger profile balloon may cross the calcified lesion. In some examples, thin membrane 1011 and/or distal membrane 1016 can be made of a less rigid material then shaft 1015 and/or carrier 1012. In some examples, thin membrane 1011 and/or distal membrane 1016 can be made of a material that is as rigid and/or more rigid than shaft 1015 and/or carrier 1012. In some examples shaft 1015 and/or carrier 1012 can be the same component, while in other examples, shaft 1015 is separate from carrier 1012.

As depicted in FIG. 11, catheter 1101 can include a thin membrane 1111, a shaft 1115, and/or a distal membrane 1116. Catheter 1101 can further include a carrier 1112 having electrode pairs 1120 and/or a cavity 1150. Electrode pairs 1120 can be the same and/or similar to electrode pairs 120, 220, 320, 420, and/or the like, as described herein. One or more electrode pairs 1120 can be located at a distal end 34 of a catheter 1101, such that sonic waves are concentrated at the distal end 34. Cavity 1150, located between a thin membrane 1111 and/or a carrier 1112, can be filled with, for example saline and/or another solution such as contrast. A thin membrane 1111, and/or carrier 1112 can be similar and/or the same as thin membrane 1011 and/or carrier 1012 of FIG. 10.

A shaft 1115 can extend towards a distal end 34 of a catheter 1101. In contrast to shaft 1015 of FIG. 10, shaft 1115 can have a constant diameter and/or a varying diameter providing a cavity 1150 that extends to a distal membrane 1116. Advantageously, extending a cavity 1150 to a distal end 34 of catheter 1101 can provide, in some cases, optimized directional control of a mechanical force "F" as depicted in FIG. 11 for modifying a calcified lesion, such that a larger profile balloon may cross the calcified lesion. In some implementations, extending a cavity 1150 to a distal end 34 of catheter 1101 can provide improved flexibility in comparison to, for example catheter 1001. For example, catheter 1001 may provide energy at a distal end 34, primarily in an axial direction, while catheter 1101 may provide concentrated energy at a distal end 34 in an axial and/or a radial direction. In some examples, thin membrane 1111 and/or distal membrane 1116 can be made of a less rigid material then shaft 1115 and/or carrier 1112. In some examples, thin membrane 1111 and/or distal membrane 1116 can be made of a material that is as rigid and/or more rigid than shaft 1115 and/or carrier 1112. In some examples shaft 1115 and/or carrier 1112 can be the same component, while in other examples, shaft 1115 is separate from carrier 1112.

In some examples, a thin membrane 1111 can have a recessed portion. In some examples a recessed portion of thin membrane 1111 can have a width $w_1$ of approximately 1 mm. In some examples a width $w_1$ can be more and/or less than 1 mm (e.g., 0.01, 0.1, 2, 5, 10 and/or the like). In some examples a recessed portion of thin membrane 1111 can have a height $h_1$ of approximately 0.5 mm. In some examples a height $h_1$ of thin membrane 1111 can be more and/or less than 0.5 mm (e.g., 0.001, 0.01, 0.1, 1, 1.5, 3 and/or the like).

Figure 12A:
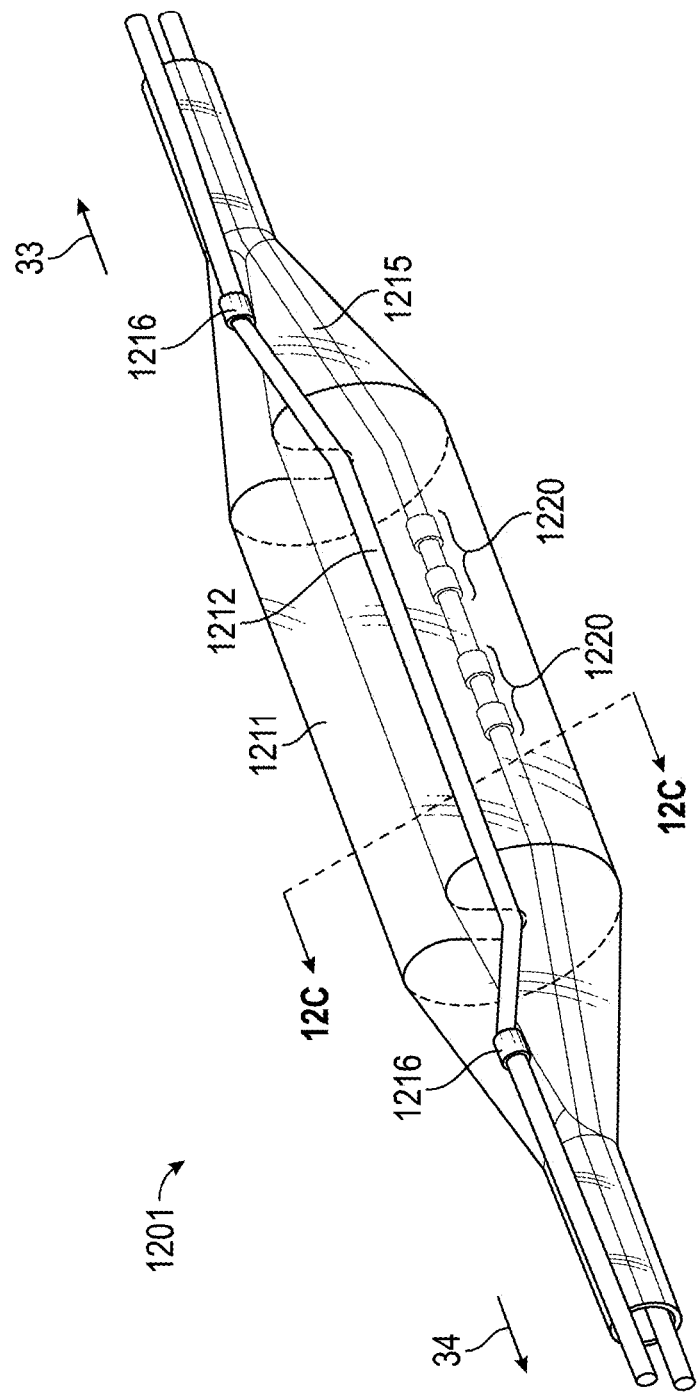
FIG. 12A illustrates an example perspective view of an eccentric IVL catheter.
Figure 12B:
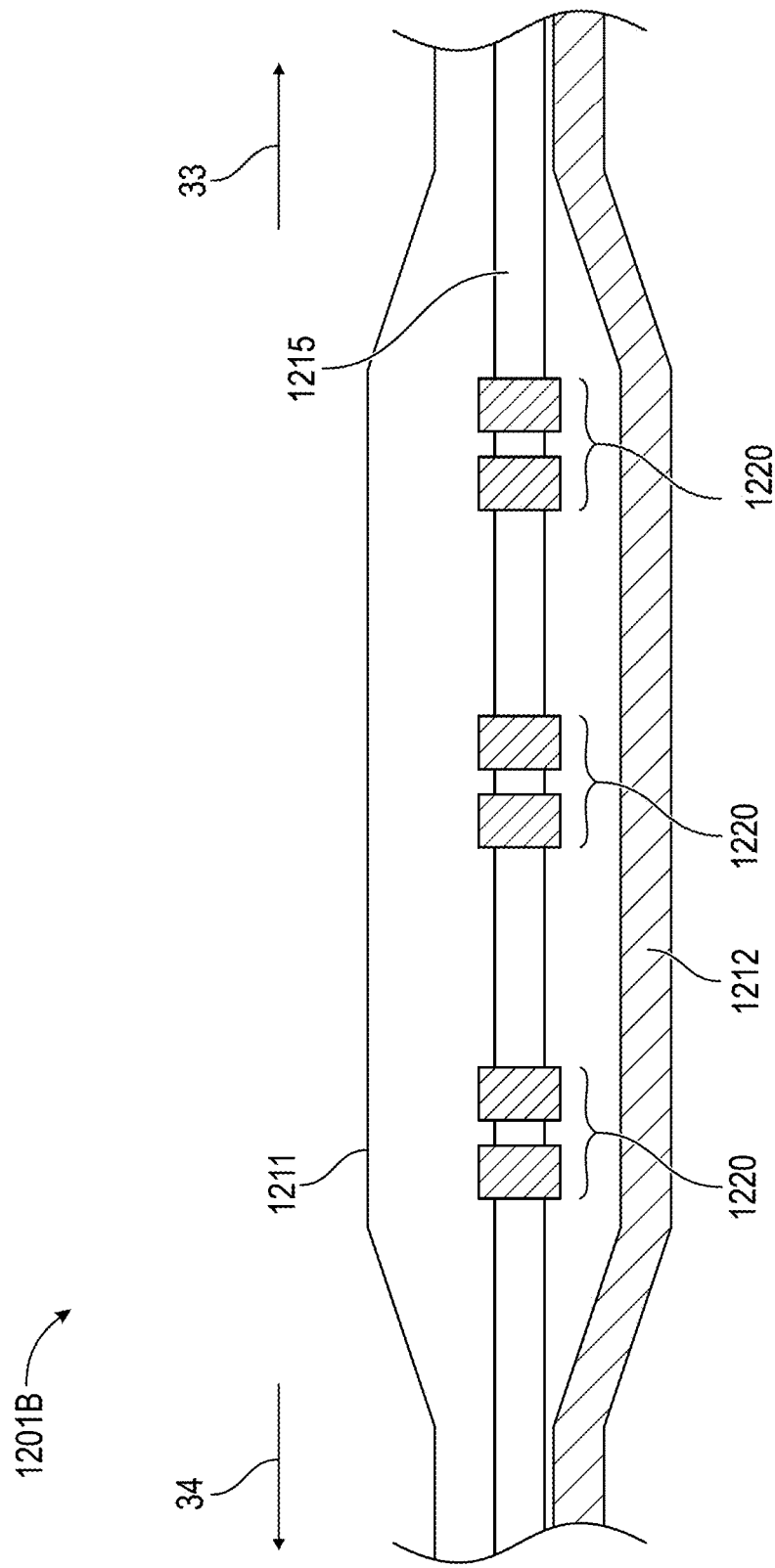
FIG. 12B illustrates an example implementation of an eccentric IVL catheter.
Figure 12C:
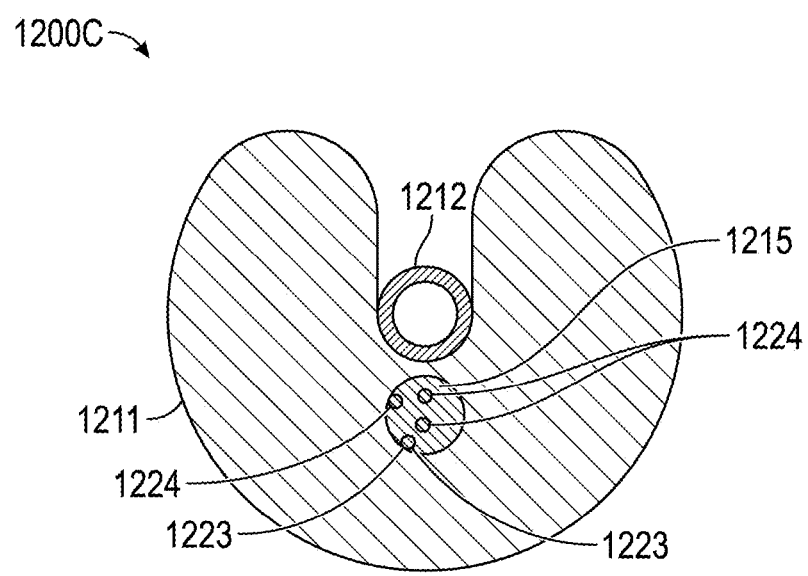
FIG. 12C illustrates an example cross-sectional view of an eccentric IVL catheter balloon.

FIGS. 12A-12C illustrate an example implementation of an eccentric IVL catheter 1201. Advantageously, an eccentric IVL catheter 1201 can be easily navigated into position within an artery, to effectively target symmetrical and/or non-symmetrical plaque without disrupting blood flow through the artery. FIG. 12A is an example perspective view of eccentric IVL catheter 1201, while FIG. 12B is an example side view 1201B of an eccentric IVL catheter 1201. As illustrated in FIGS. 12A-12B, catheter 1201 can include a balloon 1211 having a second carrier 1215 extending within the balloon 1211. A second carrier 1215 can have a solid core and/or a hollow core. A second carrier 1215 can include one or more electrode pairs 1220. Electrode pairs 1220 can be the same and/or similar to electrode pairs 120, 220, 320, 420, and/or the like, as described herein. A second first carrier 1215 can include wires 1223 and/or 1224. Wires 1223 and/or 1224 can be the same and/or similar to wires 123, 124, 223 and/or 224 of FIGS. 1, 2A, and/or 2B and/or the like. Wires 1223 and/or 1224 are depicted as inside a second carrier 1215 and/or on the surface of the second carrier 1215, however, wires 1223 and/or 1224 can be located at another position. In some implementations, wires 1223 and/or 1224 are all located within a second carrier 1215 while in some implementations one or more wires 1223 and/or 1224 are located on the surface of the second carrier 1215. Catheter 1201 can further include a carrier 1212. Carrier 1212 can have a hollow core and/or a solid core. In some examples, carrier 1212 and/or second carrier 1215 can have a lumen therethrough as described with reference to carrier 112 of FIG. 1 (e.g., to support guidewire 118 of FIG. 1 and/or the like). In some examples, carrier 1212 and/or second carrier 1215 can include markers 1216 as described with reference to markers 116 of FIG. 1.

As depicted in cross-sectional view 1200C of FIG. 12C, an IVL catheter 1201 can have a carrier 1212 positioned outside and/or adjacent to a balloon 1211. In some examples, a carrier 1212 can be secured to an outer surface of a balloon 1211 via an adhesive. In some examples, a carrier 1212 can be attached at a proximal end 33 and/or a distal end 34 of a balloon 1211. Further, a balloon 1211 can be molded into a shape as depicted in FIGS. 12C and/or another shape as necessary to modify one or more lesions. In some examples, a balloon 1211 can be shaped via a heat setting technique.

In some examples, catheter 1201 can be positioned such that balloon 1211 is adjacent to plaque (e.g., non-symmetrical plaque) while carrier 1212 is positioned on the opposite side of the plaque. Similar to one or more functions as described with reference to a dual balloon IVL catheter 901 of FIG. 9A, catheter 1201 can be positioned such that sonic waves emitted form electrode pair 1220 are transferred into non-symmetrical plaque, while energy emitted toward a carrier 1212 is reflected back to the non-symmetrical plaque.

Figure 13A:
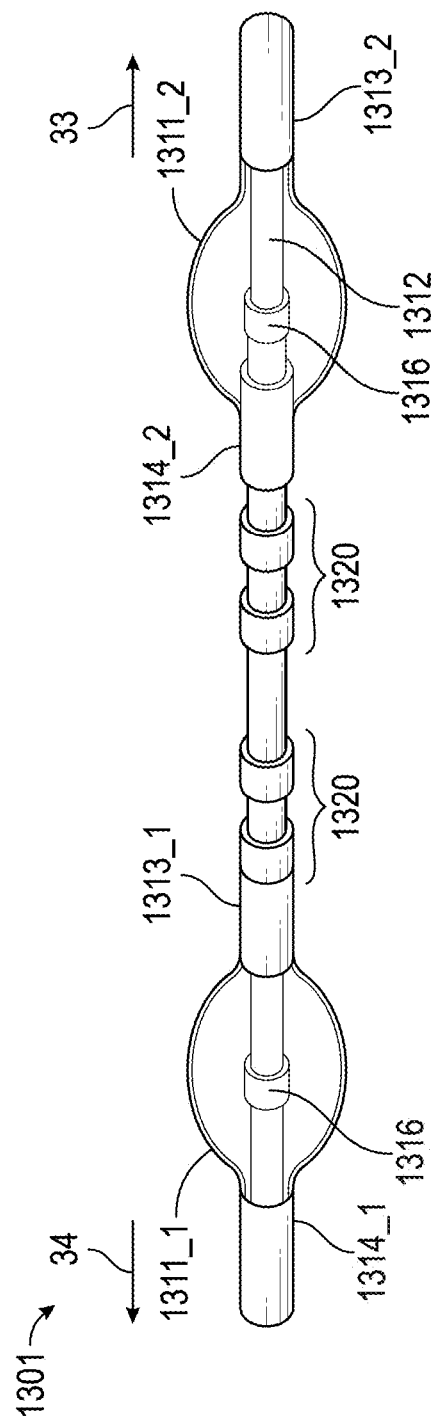
FIG. 13A illustrates an example implementation of a double occluding balloon IVL catheter.
Figure 13B:
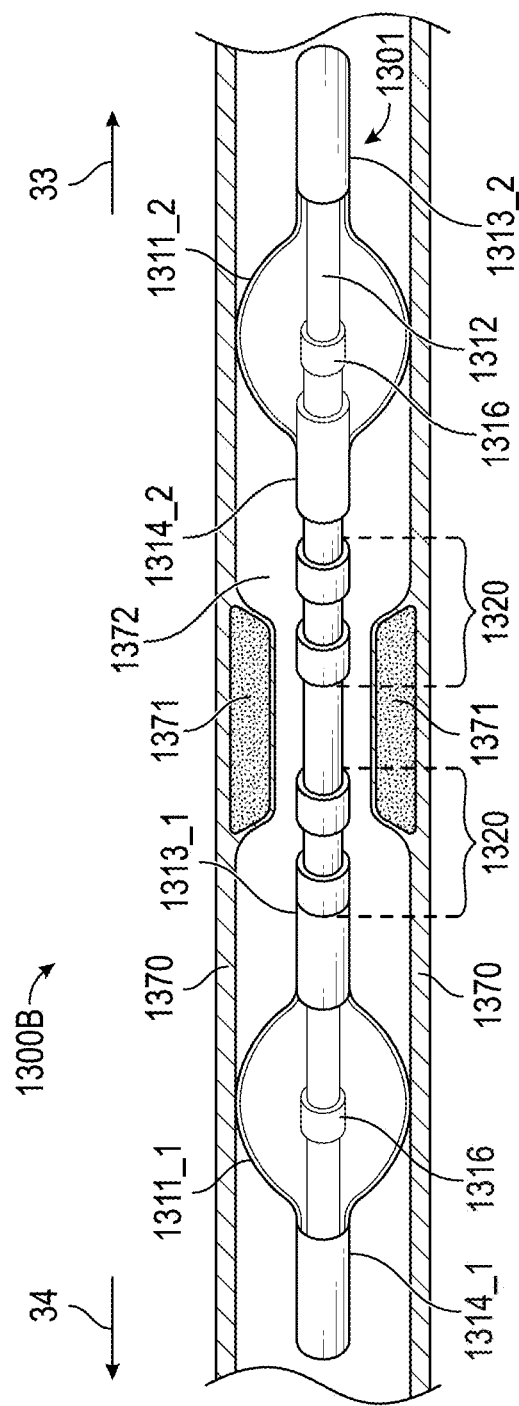
FIG. 13B illustrates an example implementation of a double occluding balloon IVL catheter in a blood vessel.

FIGS. 13A-13B illustrate example implementations of a double occluding balloon IVL catheter 1301. Catheter 1301 can have a relatively small profile, thus enabling a physician to navigate catheter 1301 into smaller blood vessels, to reach calcified lesions unavailable to one or more other catheter designs. As depicted in FIG. 13A, catheter 1301 can include a carrier 1312, a distal balloon 1311_1, a proximal balloon 1311_2, electrode pairs 1320, and/or markers 1316. Further, balloon 1311_1 can include a distal seal 1314_1 and/or a proximal seal 1313_1, and/or balloon 1311_2 can include a distal seal 1314_2 and/or a proximal seal 1313_2. Markers 1316 can be the same and/or similar to markers 116 as described in FIG. 1. Electrode pairs 1320 can be the same and/or similar to electrode pairs 120, 220, 320, 420, and/or the like, as described herein. Further, catheter 1301 can include multiple sets of electrode pairs 1320 as described herein.

Balloon 1311_1 and/or 1311_2 can be the same and/or similar to, for example, balloon 111 as described with reference to FIG. 1, however, electrode pairs 1320 may not be located inside balloon 1311_1 and/or 1311_2. Rather, electrode pairs 1320 can be positioned on the carrier 1312 between balloons 1311_1 and/or 1311_2. In some examples, electrode pairs 1320 can be longitudinally spaced between balloons 1311_1 and/or 1311_2. Advantageously, positioning electrode pairs 1320 outside balloons 1311_1 and/or 1311_2 can reduce the overall profile of catheter 1301. Further, during treatment, balloons 1311_1 and/or 1311_2 can be filled with saline, resulting in a temporary occlusion of a blood vessel. Blood within the blood vessel can be trapped between balloon 1311_1 and/or 1311_2. When electrode pairs 1320 generate sonic waves within the blood vessel, sonic energy is transferred from an area proximate to electrode pairs 1320 to the trapped blood, and/or to a calcified lesion. Thus the trapped blood acts as a conduit delivering energy to a calcified lesion similar to and/or the same as saline inside, for example, balloon 111 of FIG. 1, as described herein.

FIG. 13B depicts a catheter 1301 in an example blood vessel 1300B. An example blood vessel 1300B can have walls 1370. Example blood vessel 1300B can include plaque 1371 within walls 1370 and/or blood 1372 between walls 1370. Catheter 1301 can be positioned such that plaque 1371 is located between a distal balloon 1311_1 and/or a proximal balloon 1311_2. As described with reference to FIG. 13A, balloons 1311_1 and/or 1311_2 can occlude the walls 1370 of blood vessel 1300B near plaque 1371, such that when electrode pairs 1320 generate sonic waves, blood 1372 can transfer energy, via sonic waves, to the plaque 1371. Advantageously, catheter 1301 can have a relatively small profile, thus enabling a physician to navigate catheter 1301 into smaller blood vessels to reach calcified lesions unavailable to one or more other catheter designs.

FIGS. 14A-14B depict an indicator 117 for determining a change in state of the IVL catheter 1401 during a procedure. FIG. 14A depicts the walls 1470 and plaque 1471 before sonic pressure waves are emitted form an IVL catheter 1401, while FIG. 14B depicts the walls 1470 and modified plaque 1472 after sonic pressure waves are emitted from an IVL catheter 1401. As described above, an indicator 117 can be a check valve, a pressure sensor, a flow indicator, temperature sensor, and/or another sensor. An indicator 117 can be coupled to, as part of, along, and/or integrated into one or more locations of an IVL catheter 1401. An indicator 117 may be coupled to an inflation lumen 1419 as depicted in FIGS. 14A-14B. An inflation lumen 1419 may fill a balloon of catheter 1401 with solution as described with reference to FIG. 1. The indicator signal 117a can be connected (e.g., electrically, optically, pneumatically, hydraulically, and/or the like) between the indicator 117 and a controller (e.g., controller 251 and/or the like). A controller 251 may receive a signal 117a from indicator 117, and determine a change in state of an IVL catheter 1401.

As depicted in FIG. 14A, a first volume $V_1$ of the IVL catheter 1401 may be small, as calcified plaque 1471 within the walls 1470 of a blood vessel may be rigid and thus confine, reduce, and/or define the maximum volume of catheter 1401 (e.g., the shape of a balloon of catheter 1401). FIG. 14A further includes an example implementation of a check valve used as an indicator 117 although this is not meant to be limiting. Additional implementations of an indicator 117 may be substituted and/or utilized by an IVL catheter 1401 such as for example, a flow meter, a temperature sensor, a motion sensor and/or the like. As illustrated in the example of FIGS. 14A-14B, the indicator 117 includes a ball and a solenoid electrically coupled to the signal 117a. During an IVL procedure, catheter 1401 is positioned near calcified plaque 1471 and pressurized with conductive fluid (e.g., to approximately 4 atmospheres) via an inflation lumen 1419. When catheter 1401 and inflation lumen 1419 reach a stable pressure, one or more components of an indicator 117 may settle to a first state. As depicted in the example implementation of FIG. 14A, a stopper may be located at a first position $P_1$ within a check valve based on a pressure within the catheter 1401.

FIG. 14B illustrates an example of a successful IVL procedure. During an effective procedure, sonic pressure waves are emitted from catheter 1401, causing breaks, cracks, and/or modifications to calcified plaque 1472 within the walls 1470 of a blood vessel. When plaque 1472 is successfully modified, walls 1470 of a blood vessel and consequently catheter 1401 expand (e.g., a balloon of catheter 1401) expands in volume. As a result, catheter 1401 increases from a first volume $V_1$ to a second volume $V_2$, causing pressure within the catheter 1401 to decrease. Indicator 117 may be used to sense a pressure decrease within the catheter 1401, and transmit a signal 117a to a controller (e.g., controller 251) for determining that a procedure has successfully modified calcified plaque 1471 at a location along a blood vessel. Specific to the example implementation of FIG. 14B, a stopper moves from a first position $P_1$ to a second position $P_2$ based on a change in pressure of the catheter 1401.

Although a check valve is illustrated in FIGS. 14A-14B, an indicator 117 may include any type of sensor used to indicate a change in state of an IVL catheter 1401. For example, an indicator 117 can include a pressure sensor, flow sensor, temperature sensor, motion sensor, and/or the like. Additionally and/or optionally, a controller (e.g., controller 251) may determine whether a balloon 111 has ruptured based on an input from an indicator 117.

Figure 15:
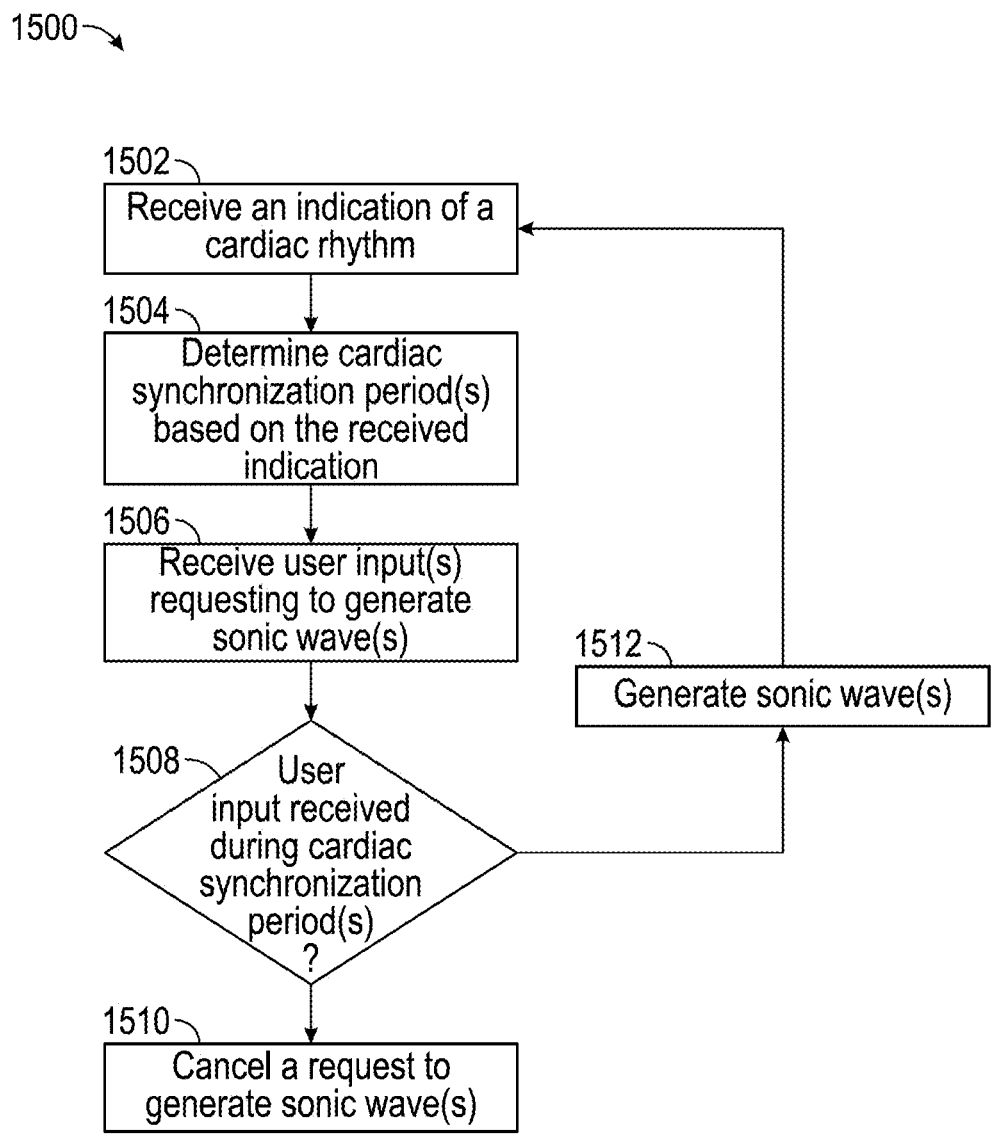
FIG. 15 depicts an example method for synchronizing emitted energy from an IVL catheter according to an example implementation.

FIG. 15 illustrates an example workflow 1500 for synchronizing emitted energy from an IVL catheter in accordance with a determined cardiac rhythm, according to an example implementation such as cardiac synchronization system 200A and/or 200B as illustrated in FIGS. 2A-2B. As an example, a controller 251 of a cardiac synchronization system 200A and/or 200B can be configured to execute example workflow 1500 of a cardiac synchronization routine. In an example implementation, example workflow 1500 may be executed after IVL catheter 201A is inserted into a patient. Although example workflow 1500 is described with reference to cardiac synchronization system 200A of FIG. 2A, the example workflow 1500 can be implemented with a cardiac synchronization system 200B of FIG. 2B and/or the like. Additionally, example workflow 1500 may be implemented with any type of IVL catheter as described herein, such as for example, catheter 101, 201A/B, 501, 601, 701, 801, 901, 1001, 1101, 1201, 1301 and/or the like. Further an IVL catheter as disclosed herein and/or used to perform workflow 1500 can be configured with one or more electrode configurations such as for example, electrode pair 120, 220, 320, 420, 520, 520a, 620, 720, 820, 920, 1020, 1120, 1220, 1320, and/or the like.

In some procedures, an IVL catheter 201A can be positioned in close proximity to the heart of a patient 270 and/or other electrically sensitive organs. Advantageously, timing electrical arcs in an IVL catheter 201A according to a cardiac rhythm of a patient 270 can mitigate certain health risks. Example workflow 1500 begins at block 1502.

At block 1502, a controller 251 can receive an indication of a cardiac rhythm of a patient 270. The cardiac rhythm can be determined by, for example, cardiac rhythm unit 260 of FIG. 2A-2B. A cardiac rhythm unit 260 can transmit (e.g., wirelessly and/or wired) information associated with a patient 270 cardiac rhythm to, for example, the energy generator 250. Further, a cardiac rhythm unit 260 can transmit a discrete signal based on one or more triggering events associated with a patient 270 cardiac rhythm to the energy generator 250. As mentioned above, a cardiac rhythm unit 260 can be any device designed to monitor and/or determine one or more characteristics of a patient 270 cardiac rhythm, including but not limited to: a heart rate, P waves (electrical activity associated with the upper chambers), QRS complex (lower chambers of the heart), PR interval (the time between the beginning of the P wave and/or the start of the QRS complex), QT interval (time between the start of the QRS complex to the end of the T wave), T wave (ventricular repolarization), and/or the like. In some examples, the cardiac rhythm unit 260 can be an AccuSync® 72 ECG trigger monitor. In some examples, the cardiac rhythm unit 260 can detect an R-wave signal and/or in response, transmit a discrete based on one or more triggering events associated with the R-wave signal.

At block 1504, a controller 251 can determine cardiac synchronization period(s) based on the received indication. A controller 251 can determine one or more periods to enable and/or disable electrical energy to an IVL catheter 201A. A controller 251 can analyze one or more characteristics of a cardiac rhythm as received from the cardiac rhythm unit 260 (e.g., a heart rate, P waves, QRS complex, PR interval, QT interval, T wave, and/or the like. Further, a controller 251 can determine whether to transmit electrical energy to electrode pairs 220 located at a distal and/or proximal end of an IVL catheter 201A while preventing the transmission of electrical energy to other electrode pairs 220, based on the received cardiac rhythm. For example, a controller 251 can instruct multiplexer 255 to transmit electrical energy to electrode pair 220_1 while further instructing multiplexer to prevent transmission of electrical energy to electrode pair 220_2. In some examples, a controller 251 can instruct the multiplexer 255 to select one or more channels to increase the concentration of sonic waves at a specific location within a blood vessel.

At block 1506, a controller 251 can receive user input(s) requesting to generate sonic waves. User input(s) can be received from, for example a physician requesting to generate sonic waves in an IVL catheter during an IVL procedure. Additionally and/or alternatively the controller 251 can receive user input(s) from another system.

At block 1508, a controller 251 determines whether the user input(s) are received during one or more cardiac synchronization period(s). If the controller 251 determines that the user input(s) are received during a cardiac synchronization period, then the workflow 1500 can continue to block 1510, where the controller 251 can cancel the request (e.g., not generate sonic waves). If the controller 251 determines that user input(s) are received outside one of a cardiac synchronization period(s), then the workflow 1500 can continue to block 1512.

At block 1510, a controller 251 can cancel a request to generate sonic waves. In some examples, if a controller 251 determines that energy generator 250, arc generator 254, and/or multiplexer 255 should be disabled based on the cardiac rhythm received from the cardiac rhythm unit 260, the controller 251 can ignore requests from a user (e.g., a physician) to generate sonic waves in an IVL catheter 201A. Additionally and/or alternatively, a controller 251 can determine, based on the cardiac rhythm of a patient, whether to selectively transmit electrical energy to one or more electrode pairs 220 during cardiac synchronization period(s) (e.g., transmitting electrical energy to electrode pair 220_1 located at, for example, a distal and/or proximal end of an IVL catheter 201A while preventing the transmission of electrical energy to electrode pair 220_2). In some examples, a controller 251 can instruct multiplexer 255 to transmit electrical energy to electrode pair 220_1 while further instructing multiplexer to prevent transmission of electrical energy to electrode pair 220_2. In some examples, a controller 251 can instruct a multiplexer 255 to select one or more channels to increase the concentration of sonic waves at a specific location within a blood vessel. After a controller 251 cancels a request to generate sonic wave(s), the example workflow 1500 may end. In some examples, the example workflow 1500 can continue to block 1502 where a controller 251 can receive another indication of a cardiac rhythm.

At block 1512, a controller 251 can emit sonic waves via electrode pairs 220. As described herein, the sonic waves can be selectively emitted from one or more electrode pairs 220 via energy generator 250, arc generator 254, and/or multiplexer 255. Further, a controller 251 can instruct arc generator 254 to generate sonic waves based on an electrical arc pattern having one or more characteristics as described herein (e.g., a monophasic pulse, a biphasic pulse, a frequency, pulse width, amplitude, phase, pulse shape, and/or the like). Once the controller 251 creates sonic waves per the user input, the workflow 1500 can continue to block 1502 where the controller 251 can receive another indication of a cardiac rhythm.

Figure 16A:
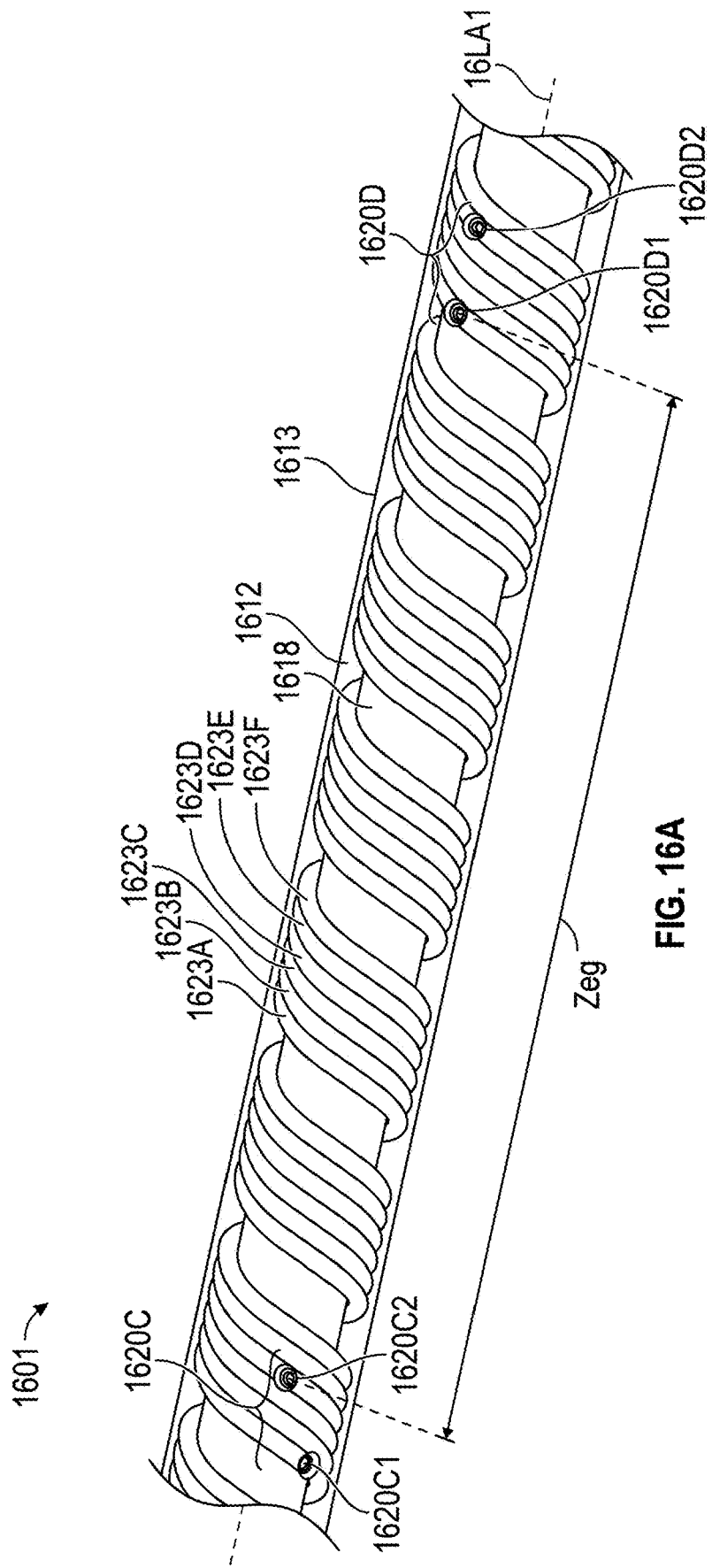
FIGS. 16A-16C are side views of various portions of an example IVL catheter.

FIG. 16A illustrates a portion of an example IVL catheter 1601 including a sheath 1618, a carrier 1612, and one or more insulated wires 1623. IVL catheter 1601 can include a balloon with similar structural and/or operational features as any of the other example balloons shown and/or described herein. Sheath 1618 includes a lumen configured to receive a guidewire. A longitudinal axis 16LA1 of the IVL catheter 1602 passes through the center of the lumen of the sheath 1618. IVL catheter 1601 can pass over the guidewire to navigate through blood vessel vasculature of a patient to be delivered to, and retracted, from a treatment site where IVL catheter 1601 can deliver sonic waves to treat calcified deposits. Carrier 1612 has an outer surface 1613 exposed to a solution in which the carrier 1612 is placed such as a saline solution within a balloon. Sheath 1618 and/or carrier 1612 can be formed of a flexible material, such as plastic or polymer. Accordingly, IVL catheter 1601 can bend as it travels through blood vessels of a patient without cracking, breaking, creasing, or otherwise permanently deforming sheath 1618 and/or carrier 1612. Carrier 1612 may be formed of a different material than sheath 1618 and/or may be constructed at a different time than sheath 1618. In some implementations, carrier 1612 may be placed over sheath 1618 (and insulated wires 1623) as a liquid and may harden in place on the sheath 1618 and thus adhere to the sheath 1618 and/or insulated wires 1623. In some implementations, sheath 1618 and carrier 1612 may be formed of a single, unitary material. In some implementations, IVL catheter 1601 may not include a carrier such that insulated wires 1623 are exposed to a solution surrounding the wires insulated 1623 and/or sheath 1618. In some implementations, insulated wires 1623 can be wrapped around the outer surface 1613 of the carrier 1612. The carrier 1612 may be formed of an electrically insulative material.

In this example, IVL catheter 1601 has six insulated wires 1623 (e.g., wires 1623A-1623F). Insulated wires 1623 are wrapped around sheath 1618 and also extend along the length of the sheath 1618 such that insulated wires are wound around sheath 1618 with a pitch. Insulated wires 1623 can be helically wound around sheath 1618. The shape of the cross-sectional profile of the helix formed by the wrapped wires 1623 may depend on the cross-sectional shape of the sheath 1618. For example, as shown here, insulated wires 1623 are helically wound in a circular helix because the cross-sectional shape of the sheath 1618 is circular. In some implementations, insulated wires 1623 can be helically wound around sheath 1618 in a polygonal helix such as an octagonal helix, nonagonal helix, decagonal helix, or the like, depending on the cross-sectional shape of the sheath 1618. In this example, insulated wires 1623 form a sextuple helix around sheath 1618. Advantageously, insulated wires 1623 can provide more structural support to IVL catheter 1601, specifically to sheath 1618, when wrapped around sheath 1618 than if the insulated wires 1623 were not wrapped but rather extended longitudinally along the sheath 1618 parallel with the sheath 1618. The structural support provided by wrapped wires 1623 can inhibit IVL catheter 1601 (e.g., sheath 1618) from cracking, creasing, etc. when bending in the blood vessels of a patient.

In this example, insulated wires 1623 are wound around sheath 1618 with a uniform pitch along at least the portion of the sheath 1618 that is shown. In some implementations, insulated wires 1623 are wound around sheath 1618 with a pitch that varies along the length of the sheath 1618 such as shown and/or described in FIG. 5F which can facilitate visualizing IVL catheter with imaging techniques such as fluoroscopy.

In this example, each of the insulated wires 1623 are wound around sheath 1618 with a same pitch as each of the other wires 1623 at least along the portion of the sheath 1618 that is shown. Thus, each of the insulated wires 1623 have the same pitch (whether varied or uniform) along the length of the sheath 1618. In some implementations, at least one of the insulated wires 1623 can have a different pitch than at least one of the other insulated wires 1623. In some implementations, each of the insulated wires 1623 can be wound with a unique pitch.

In this example, insulated wires 1623 are positioned adjacent one another. For example, insulated wire 1623B is between insulated wires 1623A and 1623C, while insulated wire 1623D is between insulated wires 1623C and 1623E, etc. Insulated wires 1623 each contact the wires to which they are adjacent. Adjacent wires can contact each other along their entire lengths or at least along a length of the sheath 1618 over which the wires extend. For example, insulated wire 1623A extends alongside insulated wire 1623B such that insulated wires 1623A and 1623B contact each other along an entire length of the sheath 1618 over which insulated wires 1623A and 1623B extend. In some implementations, one or more of the insulated wires 1623 may not contact one or more of the other insulated wires 1623. For example, insulated wire 1623B can be separated from insulated wire 1623A and/or insulated wire 1623C by a distance. Advantageously, positioning the insulated wires 1623 adjacent to, and in contact with, each other as shown here can facilitate controlling spark gap distances between electrode pairs of an emitter. For example, electrode 1620C2 may not be able to move closer to electrode 1620C1 because insulated wires 1623B-1623C are between electrodes 1620C1 and 1620C2 and there are no gaps between insulated wires 1623A-1623D. Similarly, insulated wires 1623E-1623F can inhibit electrode 1620C2 from moving away from electrode 1620C1. Thus, the insulated wires 1623 may preserve a constant distance between electrodes 1620C1 and 1620C2 by inhibiting electrodes 1620C1 and 1620C2 from moving closer to each other or away from each other. Maintaining proper distance between electrodes can facilitate creating sparks when sparks are desired or inhibiting sparks when sparks are not desired.

Insulated wires 1623 are parallel to each other in this portion of the IVL catheter 1601 that is shown such that none of the insulated wires 1623 cross each other at least in the portion shown. In some implementations, one or more of the insulated wires 1623 may be non-parallel with one or more of the other insulated wires 1623. For example, one or more of the insulated wires 1623 may cross (e.g., overlap) each other.

IVL catheter 1601 includes electrodes 1620C1, 1620C2, 1620D1, and 1620D2. Electrodes 1620C1 and 1620C2 form emitter 1620C and may be referred to as an electrode pair. Electrodes 1620D1 and 1620D2 form emitter 1620D and may be referred to as an electrode pair. As shown and/or described in greater detail at FIG. 16B, an electrode can include a portion of an electrically conductive member of an insulated wire that is exposed (e.g., an exposed portion of an electrically conducive element). Thus, reference to an electrode may refer, in whole or in part, to at least an exposed portion of an electrically conductive member. In some cases, "electrode" and "exposed portion" may be used interchangeably. Electrodes 1620C1 and 1620D1 are positioned on insulated wire 1623A. Electrode 1620C2 is positioned on insulated wire 1623D. Electrode 1620D2 is positioned on insulated wire 1623E.

Emitter 1620C is separated from emitter 1620D by distance Zeg. Specifically, electrode 1620C2 is separated from electrode 1620D1 by distance Zeg. Zeg is a straight line parallel with a longitudinal axis 16LA1 of the IVL catheter 1601.

A spark can form at emitter 1620C between electrode 1620C1 and electrode 1620C2 responsive to a voltage differential between electrodes 1620C1 and 1620C2 exceeding a threshold. The threshold can correspond with the distance between electrodes 1620C1 and 1620C. A spark can form at emitter 1620D between electrode 1620D1 and electrode 1620D2 responsive to a voltage differential between electrodes 1620D1 and 1620D2 exceeding a threshold. The threshold can be same threshold as at emitter 1620C at least because the distance between electrodes 1620D1 and 1620D2 is the same as the distance between electrodes 1620C1 and 1620C2. A spark may not form between emitter 1620C and emitter 1620D (e.g., between electrodes 1620C2 and 1620D1) at least because the distance between electrodes 1620C2 and 1620D1 (the Zeg distance) may be too great for a voltage differential between said electrodes to overcome a threshold. The voltage differential can have a pre-defined maximum because an energy generator connected to IVL catheter 1601 can have pre-defined energy outputs.

IVL catheter 1601 may be longer and include more emitters than what is shown in FIG. 16A. For example, insulated wires 1623 may span a length of the IVL catheter 1601 between 20 mm and 250 mm, between 40 mm, and 250 mm, between 60 mm, and 250 mm, between 80 mm, and 250 mm, between 100 mm, and 250 mm, between 150 mm, and 250 mm, between 200 mm, and 250 mm, between 20 mm, and 100 mm, between 40 mm and 100 mm, between 60 mm and 100 mm, between 80 mm and 150 mm, between 100 mm, and 200 mm, between 150 mm and 200 mm, between 170 mm and 220 mm, between 180 mm and 210 mm, or an length therebetween.

Figure 16B:
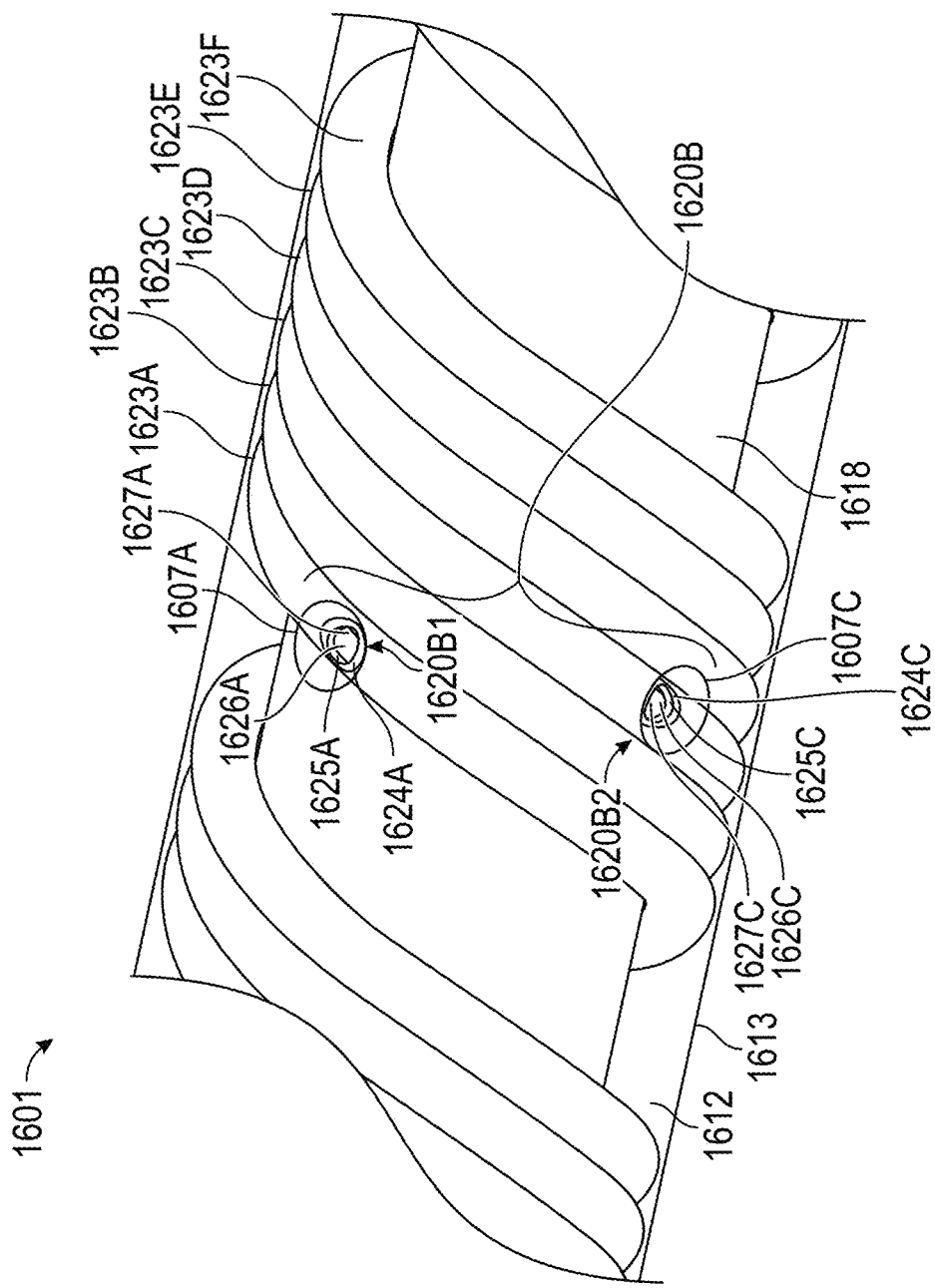

FIG. 16B is an enlarged view of a portion of the IVL catheter 1601. Insulated wire 1623A comprises insulative member 1624A and electrically conductive member 1626A. Insulative member 1624A encases electrically conductive member 1626A and electrically insulates electrically conductive member 1626A. Electrically conductive member 1626A extends along the length of the insulated wire 1623A within insulative member 1624A and is connected with an energy generator. Electrically conductive member 1626A can conduct an electrical current and can hold a voltage with respect to other objects such as other insulated wires. Electrically conductive member 1626A can be formed of a metal or metal allow such as copper. Insulative member 1624A can be formed of a plastic or polymer. Insulated wire 1623C includes insulative member 1624C and electrically conductive member 1626C with similar structural and operational features as described with respect to insulated wire 1623A. Each of the other insulated wires 1623B and 1623D-1623F can also include insulative members and electrically conductive members with similar structural and operational features as described. Insulated wires 1623 can be any gauge wire such as between 30 AWG and 40 AWG, inclusive. In some implementations, all insulated wires 1623 may be the same gauge. In some implementations, one or more of the insulated wires 1623 can have a different gauge than the others.

Carrier 1612 can include one or more carrier openings 1607, such as carrier opening 1607A and carrier opening 1607C. Carrier opening 1607A extends from the outer surface 1613 of the carrier 1612 to the insulated wire 1623A. Insulative member 1624A has an insulative member opening 1625A that exposes a portion of the electrically conductive member 1626A which can be referred to as an exposed portion 1627A. Exposed portion 1627A is an electrically conductive portion. The insulative member opening 1625A (and by consequence the exposed portion 1627A) is positioned within carrier opening 1607A. For example, exposed portion 1627A is aligned with (centered within) carrier opening 1607A. Thus, carrier opening 1607A exposes the exposed portion 1627A of the electrically conductive member 1626A. The exposed portion 1627C of insulated wire 1623C is exposed through insulative member opening 1625C and carrier opening 1607C.

In some implementations, carrier opening 1607A can be formed at the same time as insulative member opening 1625A which can ensure that the exposed portion is aligned with and/or positioned within carrier opening 1607A. For example, a laser can form a carrier opening 1607A and when finished can proceed to also form insulative member opening 1625A immediately after.

In this example, carrier openings 1607A, 1607C are depicted as having a variable width. For example, carrier openings 1607A, 1607C are conically tapered from the outer surface 1613 to the insulated wires 1623A, 1623C, respectively. In some implementations, carrier openings 1607A, 1607C can have uniform widths from the outer surface 1613 to the respective insulated wires 1623.

Carrier 1612 encases insulated wires 1623 such that insulated wires 1623 are positioned between sheath 1618 and outer surface 1613 of the carrier 1612. However, as discussed, carrier openings 1607 are configured such that the carrier 1612 does not cover the exposed portions 1627A, 1627C of insulated wires 1623A, 1623C, respectively. Thus, carrier openings 1607 provide access to the exposed portions 1627A, 1627C such that a solution surrounding the carrier 1612, such as a saline solution within a balloon, can conduct the exposed portions 1627A, 1627C.

Electrode 1620B1 is associated with (e.g., formed from) insulated wire 1623A. Electrode 1620B2 is associated with (e.g., formed from) insulated wire 1623C. Electrodes 1620B1 and 1620B2 are an electrode pair that form emitter 1620B. Electrode 1620B1 can include (e.g., refer to) one or more of carrier opening 1607A, insulative member opening 1625A, and/or exposed portion 1627A. Electrode 1620B2 can include (e.g., refer to) one or more of carrier opening 1607C, insulative member opening 1625C, and/or exposed portion 1627C.

A spark (e.g., electrical current) can travel between electrode 1620B1 and electrode 1620B2. For example, a spark can originate at exposed portion 1627A and can travel through insulative member opening 1625A, through carrier opening 1607A, along and/or over the outer surface 1613 of the carrier 1612, through carrier opening 1607C, through insulative member opening 1625C, and to exposed portion 1627C. A spark travelling from electrode 1620B1 to electrode 1620B2 has been described, however, the spark can travel in either direction between electrodes 1620B1, 1620B2, depending on whether insulated wire 1623A has a higher or lower voltage than insulated wire 1623C. IVL catheter 1601 can be configured such that insulated wire 1623A can alternate between having a higher or lower voltage than insulated wire 1623C. A spark can travel between exposed portions 1627A and 1627C when a voltage differential between the exposed portions 1627A, 1627C exceeds a threshold.

Figure 16C:
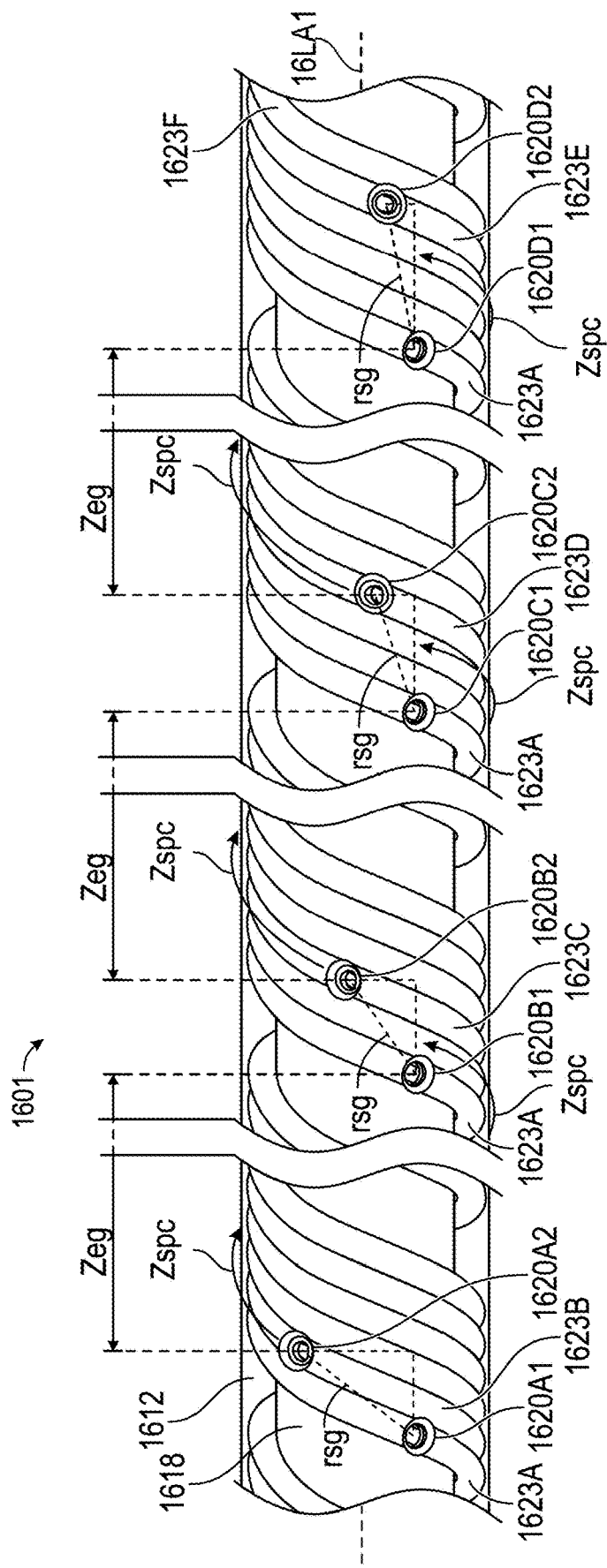

FIG. 16C illustrates a side view of various portions of IVL catheter 1601. Electrodes 1620A1, 1620A2 are shown on the far left portion of IVL catheter 1601 and are an electrode pair of a first emitter, electrodes 1620B1, 1620B2 are shown on the middle, left portion and are an electrode pair of a second emitter, electrodes 1620C1, 1620C2 are shown on the middle, right portion and are an electrode pair of third emitter, and electrodes 1620D1, 1620D2 are shown on the far right portion and are an electrode pair of a fourth emitter. The four portions of IVL catheter 1601 may be circumferentially displaced from each other by an angle rotated about longitudinal axis 16LA1. Thus, although electrodes 1620A1, 1620A2, 1620A3, and 1620A4 are shown here as though they were circumferentially aligned along the IVL catheter 1601, they may not be aligned, but rather may be circumferentially offset from one another by an angle about longitudinal axis 16LA1. Additional details regarding electrodes and/or emitters that are circumferentially offset from one another are shown and/or described with respect to FIG. 17C.

As shown, emitters of electrode pairs are longitudinally displaced from one another along the length of the IVL catheter 1601 by distances Zeg. For example, electrode 1620A2 is separated from electrode 1620B1 by distance Zeg, and electrode 1620B2 is separated from electrode 1620C1 by distance Zeg, etc. In some implementations, each of the Zeg distances may be the same. In some implementations, one or more of the Zeg distances may differ from the others.

Zspc represents the length of insulated wires between electrodes on the same wire. For example, Zspc can represent the length of the insulated wire 1623B between electrodes 1620A2, 1620B1, and can represent the length of insulated wire 1623C between electrodes 1620B2 and 1620C1, etc. In some implementations, each of the Zspc distances may be the same. In some implementations, one or more of the Zspc distances may differ from the others. The relationship of the Zeg distance between certain electrodes to the Zspc length between those electrodes may depend on the pitch at which the insulated wires 1623 are wound around sheath 1618. For example, if the wires 1623 extended longitudinally along IVL catheter 1601 without being wound, the Zeg distance and the Zspc length may be the same, whereas in the example shown, the Zspc length is greater than the corresponding Zeg distance due to the wires 1623 being wound around sheath 1618. Thus, Zeg may decrease relative to Zspc if the insulated wires 1623 are wound closer together with a smaller pitch.

The pair of electrodes 1620A1, 1620A2 are separated from each other by a distance rsg which can be referred to as the spark gap distance. Electrode pairs 1620B1, 1620B2, and 1620C1, 1620C2, and 1620D1, 1620D2, are also separated by spark gap distances rsg. In some implementations, each of the rsg distances may be the same. In some implementations, one or more of the rsg distances may differ from the others.

Because the voltage differential required to create a spark increases as distance increases a larger spark gap distance rsg can result in spark with greater energy due to the higher voltage differential when the spark forms. Similarly, a smaller rsg can result in a spark with less energy. Sparks with greater energy can create sonic waves with greater energy which can more easily eradicate calcified deposits but also bear the risk of damaging healthy tissue (e.g., blood vessel walls). Thus, establishing a proper rsg distance can facilitate treating calcified lesions effectively while also minimizing health risks. The spark gap distance rsg can be between 0.2 mm and 1.5 mm, between 0.25 mm and 1.0 mm, between 0.25 mm and 0.75 m, between 0.35 mm and 0.6 mm, between 0.4 mm and 0.6 mm, between 0.5 and 1.0 mm, between 0.75 and 1.0 mm, or any value therebetween. In some implementations, the spark gap distance rsg can be about 0.4 mm, 0.5 mm, or about 0.6 mm.

The longitudinal distance between adjacent emitters (the Zeg distance) is greater than the spark distance rsg which allows sparks to form at desired locations while inhibiting sparks from forming at undesired locations. For example, to create a spark between electrodes 1620A1 and 1620A2, an energy generator can drive voltage on insulated wires 1623A and 1623B to create a voltage differential between electrodes 1620A1 and 1620A2. However, this will also create a voltage differential between electrodes 1620A2 and 1620B1. But because electrodes 1620A1 and 1620A2 are closer together than electrodes 1620A2 and 1620B1 (e.g., rsg<Zeg), the voltage differential required to form a spark between electrodes 1620A1 and 1620A2 will be less than the voltage differential required to form a spark between electrodes 1620A2 and 1620B1. Thus, maintaining the voltage differential within thresholds by controlling an energy generator output will allow a spark to from between electrodes 1620A1 and 1620A2 but not between electrodes 1620A2 and 1620B1. Moreover, a spark will form between electrodes 1620A1 and 1620A2 thus precluding a spark from forming between electrodes 1620A2 and 1620B1.

Although a large Zeg distance can inhibit undesired sparks from forming, a large Zeg distance also increases the distance between emitters (decreases emitter density on the IVL catheter 1601) which can reduce treatment effectiveness. Thus, Zeg should be appropriately sized to inhibit undesired sparks without unduly sacrificing emitter density. Zeg can be between 1.0 mm and 10.0 mm, between 1.0 mm and 8.0 mm, between 1.0 mm and 6.0 mm, between 1.0 mm and 4.0 mm, between 1.0 mm and 3.0 mm, between 1.5 mm and 2.5 mm, between 2.0 mm and 7.0 mm, between 2.0 mm and 6.0 mm, between 3.0 mm and 6.0 mm, between 4.0 mm and 6.0 mm, between 5.0 mm and 6.0 mm, between 3.0 mm and 8.0 mm, between 4.0 mm and 8.0 mm, between 5.0 mm and 8.0 mm, between 6.0 mm and 8.0 mm, between 5.0 mm and 10.0 mm, or any value therebetween. In some cases, Zeg can be about 2.25 mm, or about 3.5 mm, or about 5.7 mm, or the like.

Zeg can be larger than rsg by about 2 to 15 times, 2 to 12 times, 2 to 10 times, 2 to 8 times, 2 to 6 times, 2 to 5 times, 2 to 4 times, 2 to 3 times, 5 to 15 times, 6 to 15 times, 7 to 15 times, 8 to 15 times, 9 to 15 times, 10 to 15 times, 12 to 15 times. For example, Zeg can be about 2 times larger than rsg, 3 times larger, 4 times larger, 5 times larger, 6 times larger, 7 times larger, 8 times larger, 9 times larger, 10 times larger, 11 times larger, 12 times larger, etc. As an example, if rsg is 0.5 mm, then Zeg can be about 11.4 times larger than rsg, or about 5.7 mm. As another example, if rsg is 0.5 mm, then Zeg can be about 4.5 times larger than rsg, or about 2.25 mm.

In some implementations, such as where insulated wires 1623 are wrapped around sheath 1618 as shown in FIGS. 16A-16C, consecutive electrodes are separated by one or more turns of the wrapped wires 1623. For example, electrode 1620A2 can be separated from electrode 1620B1 by 1 to 30 turns, 1 to 20 turns, 1 to 15 turns, 1 to 10 turns, 1 to 5 turns, 5 to 30 turns, 5 to 20 turns, 5 to 15 turns, 5 to 10 turns, 10 to 30 turns, 10 to 20 turns, 10 to 15 turns, 15 to 25 turns, or any number of turns therebetween. The distance between turns (e.g., the pitch of the wrapped wires 1623) can be between 0.5 mm and 5.0 mm, between 0.5 mm and 4.0 mm, between 0.5 mm and 3.0 mm, between 0.5 mm and 2.0 mm, between 0.5 mm and 1.5 mm, between 0.5 mm and 1.0 mm, between 0.75 mm and 1.5 mm, between 0.75 mm and 1.25 mm, between 0.75 mm and 1.0 mm, between 1.0 mm and 1.5 mm, between 1.0 mm and 1.25 mm, or any distance therebetween. The wires 1623 provide more structural support to the sheath 1618 as pitch decreases and provide more flexibility to the sheath 1618 as pitch increases. Thus, an optimal pitch can be achieved as described herein that provides optimized structural support and flexibility for the IVL catheter 1601.

A transverse cross-section through IVL catheter 1601 that is perpendicular to the longitudinal axis 16LA1 can pass through any of the electrodes without passing through the other electrode in the pair (e.g., can pass through electrode 1620A1 without passing through electrode 1620A1). A longitudinal cross-section through IVL catheter 1601 that is parallel to longitudinal axis 16LA1 (and passes through longitudinal axis 16LA1) can pass through any of the electrodes without passing through the other electrode in the pair (e.g., can pass through electrode 1620A1 without passing through electrode 1620A1). Thus, electrodes in a pair can be circumferentially and/or longitudinally offset from each other.

Figure 17A:
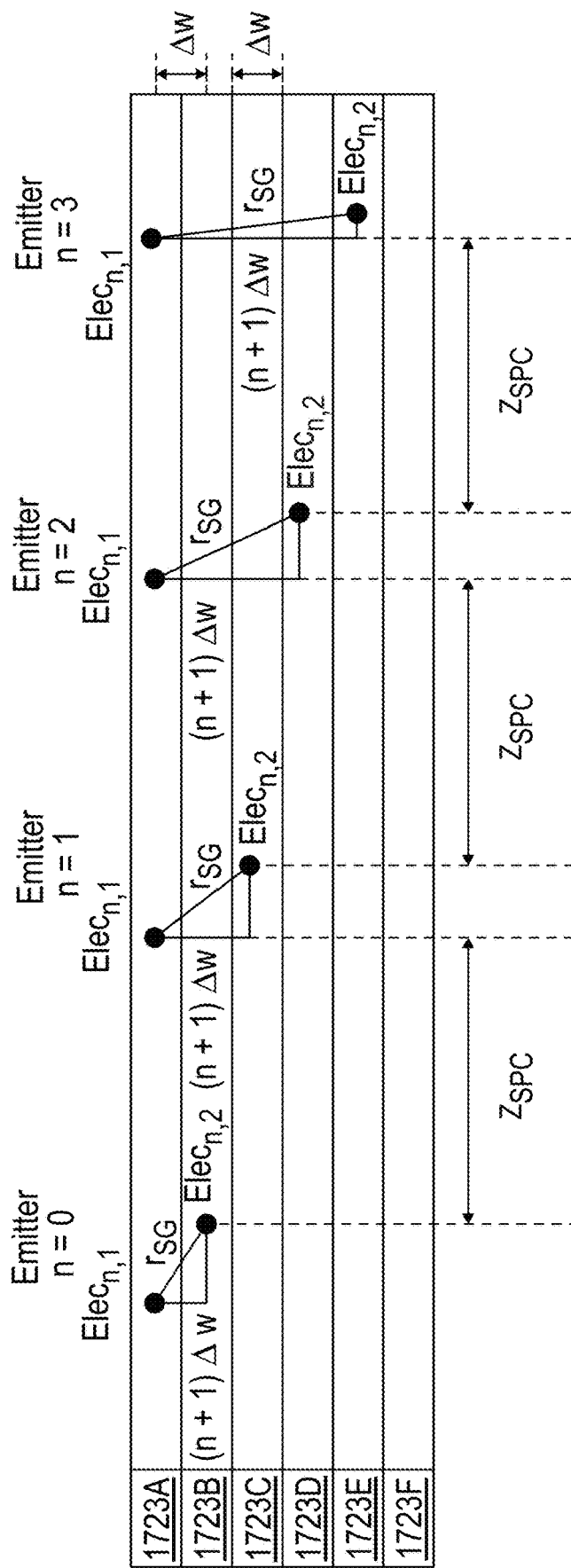
FIG. 17A is a schematic diagram illustrating insulated wires of an IVL catheter with electrodes forming emitters.

FIG. 17A is a schematic diagram illustrating example insulated wires 1723A-1723F arranged in straight rows without being wrapped. FIG. 17A may not be shown to scale. Insulated wires 1723 are configured to form sparks at emitters n=0, 1, 2, and 3. Emitter n=0 is formed from electrode 0,1 on wire 1723A and electrode 0,2 on wire 1723B. Emitter n=1 is formed from electrode 1,1 on wire 1723A and electrode 1,2 on wire 1723C. Emitter n=2 is formed from electrode 2,1 on wire 1723A and electrode 2,2 on wire 1723D. Emitter n=3 is formed from electrode 3,1 on wire 1723A and electrode 3,2 on wire 1723E. Electrodes shown and/or described herein can represent insulative member openings and/or exposed portions of electrically conductive members of insulated wires.

When insulated wires 1723 are arranged in straight rows without being wrapped, as shown here, electrode pairs in an emitter form a right triangle. Moreover, if insulated wires 1723 are wrapped in an IVL catheter, electrode pairs in an emitter may still form the same right triangle, or at least a substantially similar right triangle, ignoring potentially small variations that may arise from wrapping. Example right triangles formed from emitters on wrapped wires are shown and/or described in FIG. 16C. In FIG. 17A, each right triangle of an emitter includes a hypotenuse shown by the spark gap distance rsg, a longitudinal side (the side that is vertical with respect to the page) shown by $(n+1)\Delta w$, and a lateral side (the side that is horizontal with respect to the page). The hypotenuse (e.g., rsg) of each triangle of the various emitters may be the same length. The lengths of the other sides of the triangles may vary from emitter to emitter. Because the spark gap distance rsg is the same for each emitter, the energy differential required to from a spark at each emitter will also be the same or substantially similar.

The width (e.g., the diameter) of the wires 1723 is $\Delta w$. Moreover, the center to center spacing between adjacent wires is also $\Delta w$ in this example because adjacent wires contact each other. The center to center spacing can be greater than $\Delta w$ if adjacent wires do not contact each other. Arranging adjacent wires 1723 to contact each other as shown here can facilitate maintaining a constant center to center spacing between wires which can in turn facilitate maintaining constant spark gap distance rsg in emitters because the spark gap distance rsg is a function of the center to center spacing between adjacent wires 1723. For example, the center to center spacing between any of the wires 1723 is already at a minimum because the wires 1723 are in contact with each other and thus will not decrease. Moreover, the center to center spacing between any of the wires 1723 will likely not increase because the wires 1723 will inhibit themselves from moving away from each other as they contact each other and hold each other in place.

The longitudinal distance $(n+1)\Delta w$ between electrode pairs in an emitter is governed by the center to center spacing $\Delta w$ between adjacent wires 1723 which in this example is also the same as the width of the wires 1723. For example, in emitter n=0, electrode 0,2 is separated from electrode 0,1 by a longitudinal distance of $(0+1)\Delta w$; and in emitter n=1, electrode 1,2 is separated from electrode 1,1 by a longitudinal distance of $(1+1)\Delta w$. Thus, in this example, the longitudinal distances between electrodes in the various emitter pairs is given in increments of $\Delta w$. The longitudinal distance $(n+1)\Delta w$ is parallel with a longitudinal axis of an IVL catheter. The distance $(n+1)\Delta w$ may represent the minimum longitudinal distance that can occur electrodes such as in implementations where wires 1723 touch each other. In some cases, the longitudinal distance between electrodes in an emitter may be greater than $(n+1)\Delta w$, depending, for example, on the pitch with which the wires are wound around the sheath. For example, as shown in FIG. 16C, the longitudinal distances between electrodes in any given emitter may be greater than $(n+1)\Delta w$.

Zspc represents the distance between consecutive emitters. For example, Zspc is shown as the distance between electrode 0,2 and electrode 1,1. The Zspc distance can be the same or different between various emitters. If the insulated wires 1723 are wound in an IVL catheter, the Zspc distance may follow a helical path resulting in a straight longitudinal distance Zeg between consecutive emitters as shown and/or discussed in FIG. 16C. The Zeg distance is a function of Zspc and pitch. If the wires 1723 are not wound, Zspc may equal Zeg.

The distance Zspc can inhibit sparks from unintentionally forming between undesirable electrodes. For example, to form a spark at emitter n=0, an energy generator can drive voltage on wire 1723A and wire 1723B to create an energy differential between electrode 0,1 and electrode 0,2. However, this would also create an energy differential between electrode 1,2 and electrode 0,2 where it may not be desirable to form a spark. By regulating Zspc (and Zeg) to be greater than rsg, the energy differential required to form a spark between electrodes 0,2 and 1,1 may be greater than between electrodes 0,1 and 0,2 (assuming electrodes have the same surface areas). Thus, when Zspc (and Zeg) is greater than rsg, sparks may form between electrode pairs in an emitter but not between non-electrode pairs in adjacent emitters.

Figure 17B:
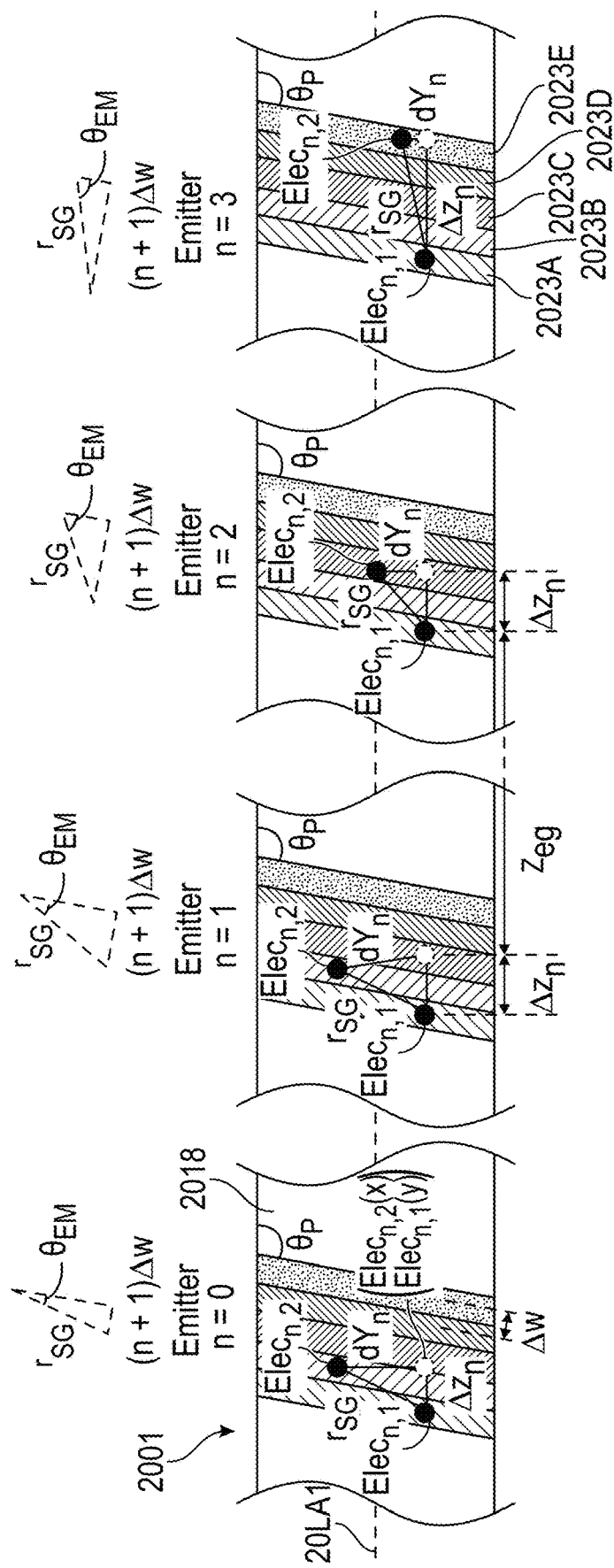
FIG. 17B is a schematic diagram illustrating insulated wires of an IVL catheter with electrodes forming emitters.

FIG. 17B is a schematic diagram illustrating example insulated wires 2023A-2023E wrapped around sheath 2018 of IVL catheter 2001. FIG. 17B may not be shown to scale. In this example, five insulated wires 2023A-2023E are shown although any number of wires may be used. Insulated wires 2023A-2023E can have similar operational and/or structural features as any of the other insulated wires shown and/or described herein. Emitter n=0 is formed from electrode 0,1 on wire 2023A and electrode 0,2 on wire 2023B. Emitter n=1 is formed from electrode 1,1 on wire 2023A and electrode 1,2 on wire 2023C. Emitter n=2 is formed from electrode 2,1 on wire 2023A and electrode 2,2 on wire 2023D. Emitter n=3 is formed from electrode 3,1 on wire 2023A and electrode 3,2 on wire 2023E. Electrodes shown and/or described herein can represent insulative member openings and/or exposed portions of electrically conductive members of insulated wires.

The electrodes n,1 and n,2 form right triangles that are shown as superimposed on IVL catheter 2001. These right triangles include an rsg hypotenuse, a longitudinal side that is parallel with a longitudinal axis 20LA1 of the IVL catheter 2001 and a lateral side that is perpendicular to the longitudinal axis 20LA1. The longitudinal sides have a length of Zn and the lateral sides have a length of dYn. The width of the wires 2023 and/or the center to center spacing between adjacent wires is shown by $\Delta w$.

The insulated wires 2023 are wrapped around the sheath 2018 such that they form an angle $\theta_p$ with the edge of the sheath as shown. The angle $\theta_p$ may be consistent along the length of the IVL catheter 2001.

FIG. 17B also shows other right triangles formed by the electrodes superimposed above IVL catheter 2001, for clarity. These other right triangles include angles $\theta_{EM}$ which may be different for each of the triangles shown. These right triangles are arranged such that the rsg hypotenuse is parallel with the rsg hypotenuse of the triangles that are superimposed on the IVL catheter 2001 and such that the angle $\theta_{EM}$ extends from the rsg hypotenuse to a leg of the triangle that is parallel with the insulated wires 2023. Accordingly, the angle from the edge of the sheath 2018 to the rsg hypotenuse is the sum of the $\theta_{EM}$ and $\theta_p$ angles when moving clockwise from the edge of the sheath 2018 to the rsg hypotenuse. Thus, the lengths of $\Delta Z_z$ and $dY_n$ can be calculated as follows:

$$\begin{bmatrix} \Delta Z_z \\ dY_n \end{bmatrix} = \begin{bmatrix} r_{SG} * |\cos(-\theta_P + \theta_{EM})| \\ r_{SG} * |\sin(-\theta_P + \theta_{EM})| \end{bmatrix}$$

The angles $\theta_{EM}$ can be calculated as follows:

$$\theta_{EM} = \sin^{-1}\left(\frac{(n+1)\Delta w}{r_{SG}}\right)$$

The lateral distance dYn may be a function of the spark gap distance rsg (which may be predetermined) and the longitudinal distance $\Delta Zn$ (which may be dictated by wire width and the number of wires between electrodes in a pair). Thus, as shown here, lateral distance may decrease as longitudinal distance $\Delta Zn$ increases (in order to maintain a constant rsg). In some implementations, the lateral distance dYn may be zero and the longitudinal distance $\Delta Zn$ may be equal to rsg. For example, another emitter can be formed from electrodes on wire 1723A and wire 1723F wherein the spark gap distance rsg is a straight line between the electrodes parallel to longitudinal axis 20LA1 without forming a right triangle. In some cases, wire 2023A may not form an emitter with another wire if the longitudinal distance $\Delta Zn$ between them would be greater than a predetermined spark gap distance rsg. Thus, in some cases, one or more of the wires 1723 may not form an emitter with one or more of the other wires 1723.

Figure 17C:
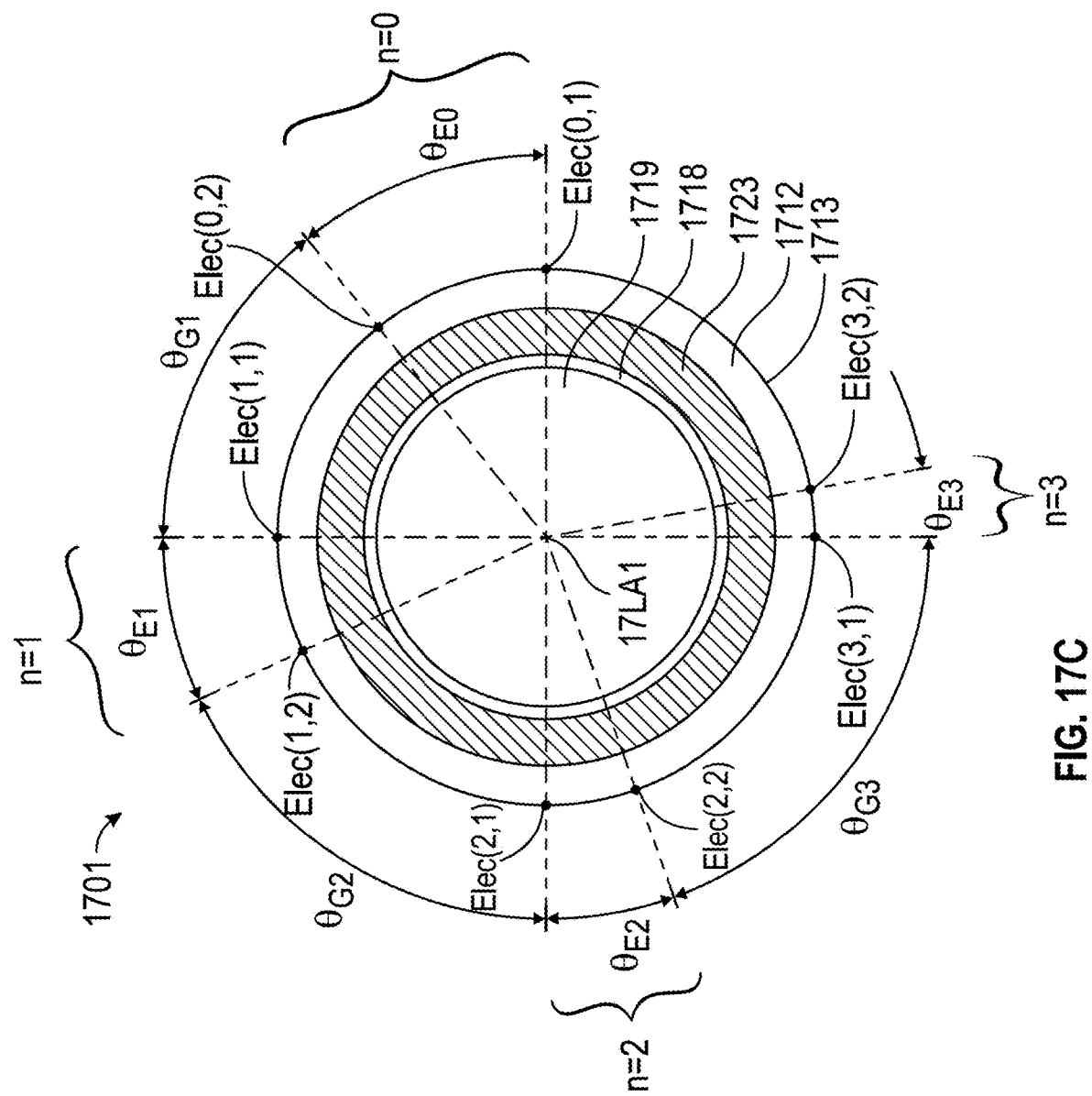
FIG. 17C is a cross-section view of an example IVL catheter with insulated wires having electrodes forming emitters.

FIG. 17C is a cross-section view of a portion of an example IVL catheter 1701 which includes a sheath 1718 having a lumen 1719 configured to receive a guidewire therethrough, insulated wires 1723 wrapped around the sheath 1718, and a carrier 1712 encasing the wires 1723 and the sheath 1718. FIG. 17C may not be shown to scale. Longitudinal axis 17LA1 extends through the center of the lumen 1719 of the sheath 1718. The carrier 1712 has an outer surface 1713. IVL catheter 1701 has a plurality of electrodes (e.g., (0,1), (0,2), (1,1), (1,2), (2,1), (2,2), (3,1), (3,2)). In this example, electrodes are represented at the outer surface 1713 of the carrier 1712 where carrier openings may be positioned through which sparks may pass, however this is not intended to be limiting as "electrodes" may also refer to, and/or be represented by, exposed portions and/or insulative member openings of wires 1723 which may be positioned at between carrier 1712 and the wires 1723. Whether the discussing electrodes with respect to the outer surface 1713 of the carrier 1712 and/or between the carrier 1712 and the wires 1723, the angles between electrodes would remain the same.

Electrode pair 0,1 and 0,2 form an emitter which may correspond to emitter n=0 in FIG. 17A (or FIG. 17B in some cases). Electrode pair 1,1 and 1,2 form an emitter which may correspond to emitter n=1 in FIG. 17A. Electrode pair 2,1 and 2,2 form an emitter which may correspond to emitter n=2 in FIG. 17A. Electrode pair 3,1 and 3,2 form an emitter which may correspond to emitter n=3 in FIG. 17A. The angles $\theta E0, \theta E1, \theta E2, \theta E3$, between respective electrodes in a pair may depend on the lateral distance (e.g., dYn) between respective electrodes in a pair. Thus, the relationship between the various angles may be as follows $\theta E0 > \theta E1 > \theta E2 > \theta E3$. In some implementations, $\theta E0$ may be between about 25° and 45°, $\theta E1$ may be between about 20° and 40°, $\theta E2$ may be between about 15° and 35°, and $\theta E3$ may be between about 5° and 20°.

The angles $\theta G1, \theta G2, \theta G3$, between the various emitters may depend on the distance (e.g., Zspc) between adjacent emitters which may all be equal or substantially equal. Thus, in some cases, the various angles $\theta G1, \theta G2, \theta G3$ may all be equal or substantially equal (assuming a constant pitch). One or more of $\theta G1, \theta G2, \theta G3$ can be between 50° and 85°, between 50° and 75°, between 50° and 60°, between 60° and 75°, between 55° and 70°, between 55° and 65°, or between 65° and 75°.

The emitters are separated by angles $\theta G1, \theta G2, \theta G3$, which may be referred to as the emitters being circumferential offset. For example, the emitter formed by electrode pair 0.1 and 1,1 is circumferentially offset from the emitter formed by electrode pair 1,1, and 1,2 by angle $\theta G1$. A single wire (e.g., wire 1723A) can have a plurality of electrodes that form a plurality of emitters, one or more of which are circumferentially offset from the others. Because the emitters are circumferentially offset (e.g., angular separation) from each other, the various emitters can emit sonic waves in a plurality of directions without having to rotate the IVL catheter 1701 thus allowing for more effective treatment. For example, calcium deposits may form non-uniformly and in more than one place on the surfaces of the vasculature of a patient. Circumferentially and/or longitudinally separating emitters can increase the likelihood of applying sonic waves from the emitters to the calcium deposits wherever they may have formed on the vasculature. In some aspects, consecutive emitters may be longitudinally separated by a distance without being radially separated by an angle or vice versa. Thus, as described, consecutive emitters may be located at different longitudinal positions on the IVL catheter regardless of the angle that separates them radially. Thus, in some cases, emitters, (e.g., emitters that are consecutively spaced without any other emitters between them) may not be circumferentially aligned and/or may not be longitudinally aligned, or in some cases they may be circumferentially aligned and/or longitudinally aligned.

A pair of electrodes of a single emitter can be circumferentially offset (as shown in FIG. 17C) and/or longitudinally offset (as shown in FIGS. 17A-17B). For example, electrodes 0,1 and 1,1 of emitter n=0 are shown in FIG. 17C as being circumferentially offset because they are separated by angle $\theta E0$. As such, a longitudinal cross-section of IVL catheter 1701 along longitudinal axis 17LA1 through the plane of the page that intersects one of electrodes 0,1 and 1,1 may not intersect the other electrode. Electrodes 0,1 and 1,1 can be longitudinally offset (as shown and/or described by the example electrodes in FIGS. 16C and/or 17A-17B) because they may be longitudinally separated by a distance such as the (n=1) w distance. As such, a transverse cross-section of IVL catheter 1701 parallel to the plane of the page that intersects one of electrodes 0,1 and 1,1 may not intersect the other electrode. Thus, in some cases, a pair of electrodes in an emitter may not be circumferentially aligned and/or may not be longitudinally aligned, or in some cases they may be circumferentially aligned and/or longitudinally aligned.

The carrier 1712 can be thicker than the wires 1723 such that the outer surface 1713 of the carrier 1712 extends past the wires 1723 from the sheath 1718 as shown. The thickness of the carrier 1712 can be measured from the outer surface 1713 to a surface of the sheath 1718 that contacts the wires 1723. The thickness of the wires 1723 can correspond to their diameter as determined by their AWG size. In some implementations, the carrier 1712 may be between 100% and 200% thicker than the wires 1723, between 100% and 150% thicker, between 100% and 125% thicker, between 100% and 115% thicker, between 100% and 110% thicker, between 125% and 200% thicker, between 150% and 200% thicker, between 175% and 200% thicker, between 125% and 175% thicker, between 125% and 150% thicker, or between 200% and 250% thicker.

As shown in the cross section of FIG. 17C, the insulated wires 1723 extend no further away from the sheath 1718 than the thickness of the wires 1723 themselves. This may be because the wires 1723 contiguously contact the sheath 1718. For example, the wires 1723 may not overlap with one another or be stacked on top of each other etc. which would cause separation between the sheath 1718 and at least some of the wires 1723. This may be the case along the entire IVL catheter 1701. The diameter of the outer surface 1713 of the carrier 1712 can be between 0.02" and 0.06", between 0.03" and 0.05", between 0.03" and 0.045", between 0.03" and 0.04", between 0.035" and 0.05", between 0.04" and 0.05", or any value therebetween. As discussed, various implementations of IVL catheters can have anywhere from 3 insulated wires to 15 insulated wires, for example, or any other number of wires as shown and/or discussed herein. Thus, an IVL catheter with 10 insulated wires for example can have a diameter (of the carrier) between 0.03" and 0.05". In some cases, the diameter of various IVL catheters may not change regardless of the numbers of wires in each catheter. For example, an IVL catheter with 6 insulated wires can have the same carrier diameter as an IVL catheter with 12 insulated wires (and the diameter of each may be between 0.03" and 0.05").

The outer surface 1713 of the carrier 1712 may be circular. The outer surface 1713 of the carrier 1712 may be smooth without any protrusions being raised from the outer surface 1713. Thus, the outer surface 1713 may be more flexible than if any objects were coupled to the outer surface 1713 or if any portions of the outer surface 1713 protruded from the circular cross-section.

The locations of electrodes on an IVL catheter can be determined to form carrier openings of the electrodes. For example, a laser drilling system can be programmed with locations at which to form carrier openings of electrodes. The locations of electrodes can be represented with cylindrical coordinates (r, $\theta$, z). For example, the location of electrodes (n, 1) and (n,2) in a pair can be shown by the following matrices, respectively:

$$Elec_{n,1} = \begin{bmatrix} R_{GWL} \\ \theta_{OR} \\ Elec_{n-1,2}(Z) + z_{eg} \end{bmatrix}$$

$$Elec_{n,2} = \begin{bmatrix} R_{GWL} \\ \theta_{OR} + \Delta\theta_{En} \\ Elec_{n,1}(Z) + \Delta Z_n \end{bmatrix}$$

$R_{GWL}$ is the distance of the electrode from the longitudinal axis 17LA1 and can be equal to the radius of the outer surface 1713 of the carrier 1712. $R_{GWL}$ may be constant for all electrodes at least because the carrier 1712 may have an outer surface 1713 with a uniform radius. $\theta_{OR}$ is the angular position of the first electrode in a pair measured from a reference point which may be the electrode from a previous pair (e.g., $Elec_{n-1,2}$). $\theta_{OR}$ may be equal to $\theta_{Gn}$ in FIG. 17C. $\theta_{En}$ is the angle between electrodes in a pair. For example, electrodes (0,1) and (0,2) shown in FIG. 17C are separated by angle $\theta_{E0}$. $\theta_{En}$ can vary from emitter to emitter. $\theta_{En}$ can be determined using the following equation, where $dY_n = r_{SG} * |\sin(-(\theta_P + \theta_{EM}))|$ as described in FIG. 17B:

$$\Delta\theta_{En} = 2 * \sin^{-1}\left(\frac{|dY_n|}{2 * R_{GWL}}\right)$$

The longitudinal coordinates of the electrodes are shown with Z coordinates. For example, the longitudinal location of electrode (n,1) is the longitudinal location of the electrode in the prior emitter ($Elec(n-1,2)$) plus the Zeg distance (which is a function of Zspc distance). The longitudinal location of electrode (n,2) is the longitudinal location of the first electrode in the pair ($Elec(n,1)$) plus the $\Delta Z_n$ distance. In some cases, the $\Delta Z_n$ distance can be approximated with $(n+1)\Delta w$, for example such that $(n+1)\Delta w$ is always less than $\Delta Z_n$. In some cases, $\Delta Z_n = r_{SG} * |\cos(-(\theta_P + \theta_{EM}))|$ as described in FIG. 17B.

Substituting the equations above yields the following matrices of electrode coordinates that govern electrode positions in an IVL catheter:

$$Elec_{n,1} = \begin{bmatrix} R_{GWL} \\ \theta_{OR} \\ Elec_{n-1,2}(Z) + z_{eg} \end{bmatrix}$$

$$Elec_{n,2} = \begin{bmatrix} R_{GWL} \\ \theta_{OR} + 2 * \sin^{-1}\left(\frac{|dY_n|}{-2 * R_{GWL}}\right) \\ Elec_{n,1}(Z) + r_{SG} * |\cos(-\theta_P + \theta_{EM}))| \end{bmatrix}$$

These matrices can be programmed into a system to form carrier openings in an IVL catheter. For example, matrices of electrode coordinates can be programmed to a laser system that can use a laser to form carrier openings and/or insulative member openings (e.g., aligned with each other) at precise locations which can be associated with and/or serve as electrodes.

The longitudinal distance Zeg between consecutive emitters can vary depending on the implementation and may be calculated as follows:

$$Z_{eg} = \frac{\left(l_{bln} - (2 * d_{gap}) - \sum_{i=1}^{n} \Delta z_n\right)}{nEM - 1}$$

As shown in the formula above, Zeg can depend on balloon length ($l_{bln}$), a gap on either end of the balloon ($d_{gap}$), the number of emitters (nEM), and the sum of the longitudinal distances of each emitter ($\Delta Zn$). The above formula may provide the maximum distance possible that Zeg could be given the constraints (e.g., number of emitters, working length of catheter). Implementing Zeg as the greatest distance possible may ensure that emitters are maximally spaced from each other and thus evenly distributed between ends of the catheter. The minimum distance of Zeg may be a function of the spark gap distance rsg. For example, Zeg may never be less than 5*rsg, 4*rsg, 3*rsg, 2*rsg, 1.5*rsg, or the like. Such a constraint may inhibit sparks from unintentionally forming between undesired electrodes because a spark may not be capable of bridging a gap greater than rsg given the thresholds (voltage, time) at which an energy generator drives the wires.

Figure 18A:
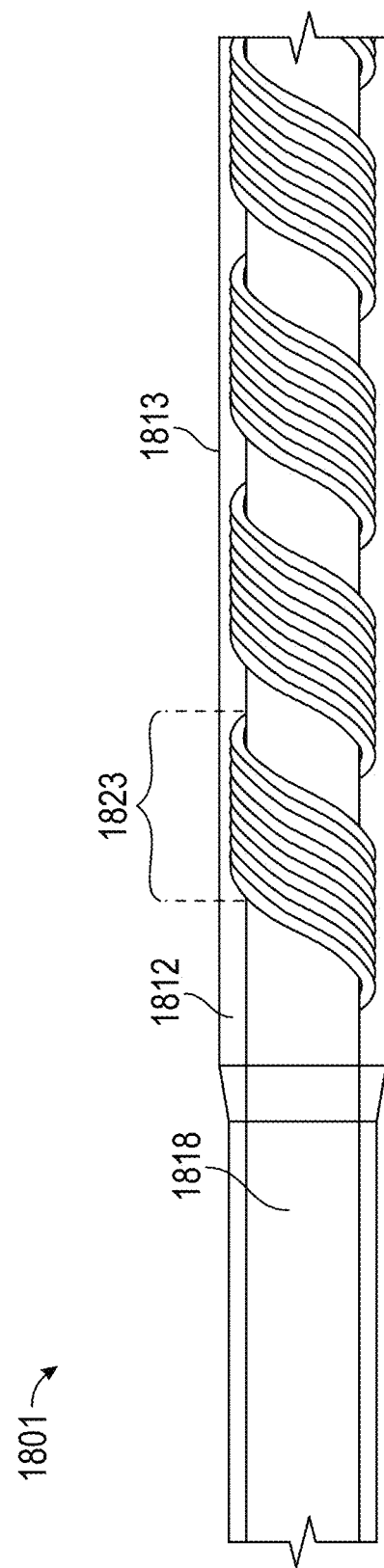
FIG. 18A is a side view of a portion of an example IVL catheter.

FIG. 18A is a side view of a portion of an example IVL catheter 1801 which comprises a sheath 1818, a carrier 1812 having an outer surface 1813, and a plurality of insulated wires 1823. The IVL catheter 1801 can include similar structural and/or operational features as any of the other example IVL catheters shown and/or described herein.

In this example, IVL catheter 1801 has 10 wires. In some implementations, IVL catheter 1801 can have 2 wires, 3 wires, 4 wires, 5 wires, 6 wires, 7 wires, 8 wires, nine wires, 10 wires, 11 wires, 12 wires, 13 wires, 14 wires, 15 wires, between 15 and 20 wires, etc. The insulated wires 1823 can electrically connect to an energy generator and can conduct energy originating from the energy generator. The insulated wires 1823 can change voltage responsive to a change in the energy they conduct. The insulated wires 1823 can each include an electrically conductive member that is enclosed within an electrically insulative member.

The portion of the IVL catheter 1801 shown in FIG. 18A may be a distal portion. For example, the insulated wires 1823 may terminate at this distal portion shown here and may connect to an energy generator a proximal portion on the other end of the IVL catheter 1801. The carrier 1812 tapers at this portion of the IVL catheter 1801 such that the outer surface 1813 changes diameter. The sheath 1818 extends distally beyond the insulated wires 1823.

In this example, the insulated wires 1823 are helically wound around the sheath 1818 along a length of the IVL catheter 1801. The insulated wires 1823 can be wound with a uniform pitch or a variable pitch. The sheath 1818 can be formed of a flexible material that can deform responsive to force. Advantageously, the helically-wound insulated wires 1823 can provide support to the sheath 1818 such as to inhibit the guidewire from breaking when bending and to inhibit the sheath of the IVL catheter 1801 from collapsing when bending. Accordingly, the structural support provided from the helically wound insulated wires 1823 can allow for a longer IVL catheter than may otherwise be possible without such helically wound insulated wires 1823.

Figure 18B:
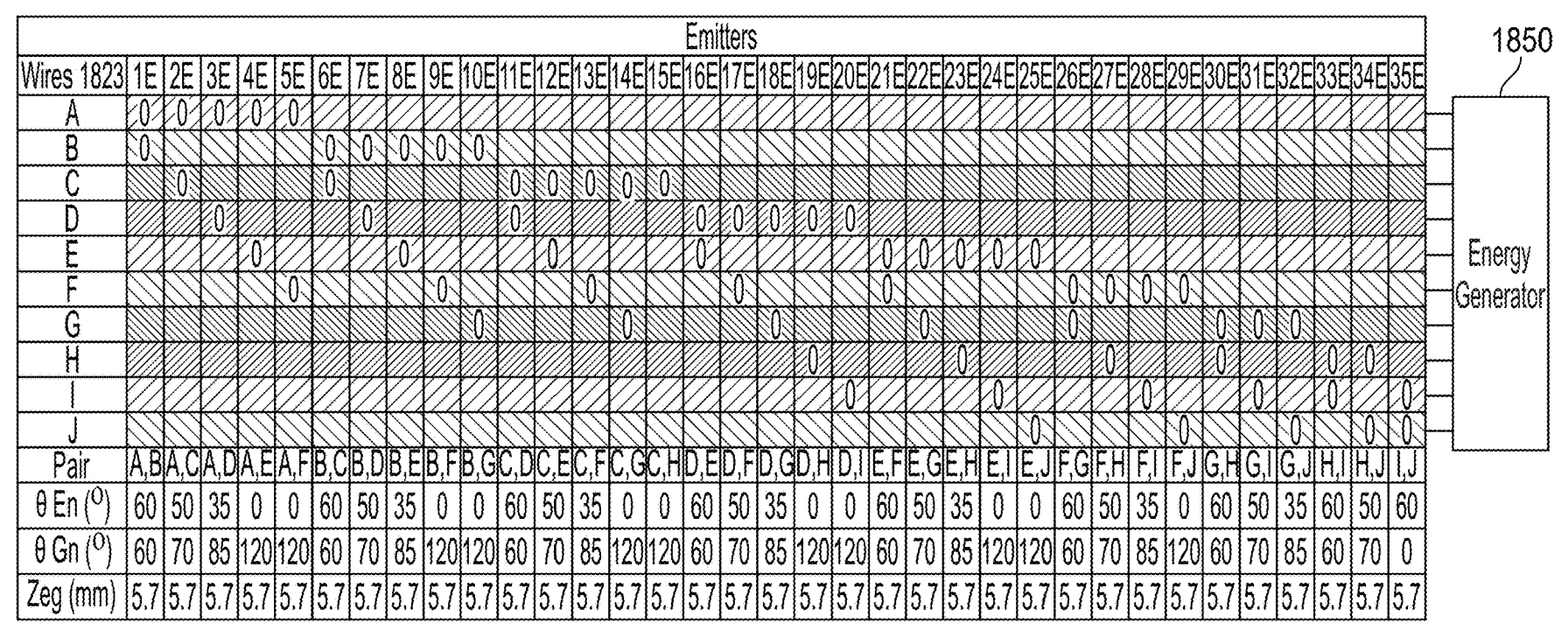

FIG. 18B is a schematic diagram illustrating example insulated wires 1823A-1823J arranged in straight rows without being helically wound. FIG. 18B may not be shown to scale. Insulated wires 1823A-1823J can correspond to insulated wires 1823 of IVL catheter 1801 shown and/or described in FIG. 18A but in a state where they are not wrapped. Although shown in straight rows in FIG. 18B, insulated wires 1823A-1823J can be helically wound as shown and/or described in FIG. 18A.

Insulated wires 1823A-1823J are symbolically divided into columns with each column representing an emitter having an electrode pair. In this example, insulated wires 1823A-1823J form 35 emitters each shown as a distinct column. The electrodes are shown as circles within each cell of the rows and columns and the electrodes represent one or more of an exposed portion of a wire, an insulative member opening of a wire, and/or a carrier opening aligned with an exposed portion. For example, emitter 1E is formed by an electrode in insulated wire 1823A and an electrode in insulated wire 1823B. Electrodes in an emitter pair, are shown as being vertically aligned which may ignore, for simplicity, any horizontal displacement between such electrodes (e.g., the dYn component shown and/or described in FIG. 17B). However, such a dYn component may exist although not explicitly represented in this schematic diagram.

Each of the insulated wires 1823A-1823J can form a plurality of emitters. For example, as shown, insulated wire 1823A can form five emitters (1E-5E) with wires 1823B-1823F, respectively, and each of wires 1823B-1823F can also form an additional five emitters each. The number of emitters that can be formed from a number of wires (n) may be given by the following formula:

$$\# \text{ of emitters} = \frac{n!}{(n-2)!\,2!}$$

Using the above formula, the following table shows example numbers of emitters that are possible given a certain number of wires. The table below is provided as example implementations of IVL catheter with various numbers of wires and emitters.

| # of wires | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|
| # of emitters | 1 | 3 | 6 | 10 | 15 | 21 | 28 | 36 | 45 | 55 | 66 | 78 | 91 | 105 | 120 |

As shown, 45 emitters are possible in implementations with 10 wires. The example implementation of FIG. 18B has 10 wires and 35 emitters. For example, insulated wire 1823A may not form an emitter with wires 1823G-1823J, and insulated wire 1823B may not form an emitter with wires 1823H-1823J, etc. The number emitters that are possible in the implementation of FIG. 18B (and other implementations) can be constrained by the distance between wires. For example, the minimum distance that could be achieved between hypothetical electrodes on wires 1823A and 1823G may be greater than the predetermined spark gap distance that is determined for this implementation. This may be due to the size of the wires. For example, if the insulated wires 1823 have a diameter of about 0.1 mm then the center to center spacing between wires 1823A and 1823G would be about 0.6 mm (assuming the wires are touching adjacent wires). If the spark gap distance is less than 0.6 mm (e.g., 0.5 mm) then a spark could not be formed between insulated wire 1823A and any of wires 1823G-1823J. Thus, in some cases, the number of emitters that are possible for a given number of wires may be constrained from the theoretical maximum given the spark gap distance and wire gauge size.

As shown in the formula and/or table above, the number of emitters that are possible may correspond exponentially with the number of wires. Advantageously, forming a plurality of emitters from each wire (rather than only a single emitter) can reduce the number of wires and/or can increase the number of emitters on the IVL catheter. Reducing the number of wires can reduce the size of an IVL catheter allowing for more precise intravascular treatment. Increasing the number of emitters can allow an IVL catheter to produce more sonic energy (e.g., per length of the catheter). Moreover, a plurality of emitters from each wire can increase emitter density per length of catheter. Accordingly, the systems and devices described herein can implement a long IVL catheter (e.g., longer than 60 mm, longer than 80 mm, longer than 100 mm, longer than 150 mm, longer than 200 mm, etc.) without sacrificing emitter density on the catheter and/or without requiring significantly more wires.

In some implementations, an IVL catheter can have an insulated wire with a plurality of electrodes configured to form an emitter with another insulated wire also having a plurality of electrodes. In some implementations, an IVL catheter can have a plurality of insulated wires with each wire having a plurality of electrodes, such as at least three electrodes, such that each wire can form a plurality of emitters. In some implementations, each insulated wire in an IVL catheter can have the same number of electrodes as the number of wires minus one. For example, in an IVL catheter with six wires, each of those six wires can have five electrodes. In some implementations, each wire in an IVL catheter can have a plurality of electrodes that is less than the number of wires. In some implementations, each wire may have the same number of electrodes as each of the other wires.

As shown in the table above, various IVL catheter configurations are contemplated herein wherein an IVL catheter can form at least twice as many emitters as wires, at least three times as many emitters as wires, at least four times as many emitters as wires, etc. Various IVL catheter configurations are contemplated herein that have twice as many electrodes as wires, at least three times as many electrodes as wires, at least four times as many electrodes as wires, at least five times as many electrodes as wires, etc. The number of electrodes may be twice as much as the number of emitters.

In some implementations, an IVL catheter can have at least 5 wires configured to form between 6 and 10 emitters, inclusive. In some implementations, an IVL catheter can have at least 6 wires configured to form at least 10 emitters, such as between 10 and 15 emitters inclusive. In some implementations, an IVL catheter can have at least 7 wires configured to form at least 10 emitters, such as between 10 and 21 emitters inclusive. In some implementations, an IVL catheter can have at least 8 wires configured to form at least 15 emitters, such as between 15 and 28 emitters inclusive. In some implementations, an IVL catheter can have at least 9 wires configured to form at least 25 emitters, such as between 25 and 36 emitters inclusive. In some implementations, an IVL catheter can have at least 10 wires configured to form at least 30 emitters, such as between 30 and 45 emitters inclusive.

The insulated wires 1823A-1823J are electrically connected with energy generator 1850. Each of the insulated wires 1823A-1823J can be connected with energy generator 1850 independently of each of the other insulated wires, such that energy generator 1850 can drive voltage on any of the wires 1823A-1823J without driving voltage on any of the other wires. Insulated wires 1823A-1823J can be directly electrically connected with energy generator 1850 without any other wires, conductors, points of contact, etc. between respective insulated wires 1823 and the energy generator 1850. A direct electrical connection can include a mechanical connection such as physical contact between the insulated wires 1823 and the energy generator 1850. For example, there may be no gaps between the energy generator 1850 and the wires 1823A-1823J. Accordingly, energy generator 1850 can be directly and/or independently connected to a plurality of insulated wires that is each configured to form a plurality of emitters. Each of the insulated wires 1823A-1823J may be contiguous throughout the length of each wire. For example, insulated wire 1823A may not have any gaps or breaks along the length of the wire 1823A between the energy generator 1850 and one or more of the electrodes on the insulated wire 1823A.

Energy generator 1850 can be configured to drive a voltage on any of insulated wires 1823A-1823J. Driving a voltage on a wire can include conducting electrical current through the wire. Energy generator 1850 can drive the voltage on a wire high or low. For example, energy generator 1850 can drive the voltage on wires 1823A-1823J according to any of the example pulse patterns shown and/or described herein such as in FIGS. 2C-2F. Driving a voltage on a wire can induce a voltage differential between said wire and the other wires which can cause a spark to form. Energy generator 1850 can drive voltage on two of the wires 1823A-1823J simultaneously. For example, energy generator 1850 can drive the voltage on one of the wires 1823A-1823J high while driving the voltage on another one of the wires 1823A-1823J low. Driving the voltage on two wires (e.g., high and low) can cause a single spark to form between the wires. The voltage differential between two wires that are driven high and low respectively may be greater than the voltage differential between other wires. For example, energy generator 1850 can drive a voltage on insulated wire 1823A (either high or low) and can simultaneously drive a voltage on insulated wire 1823F (with an opposite polarity of insulated wire 1823A and which may or may not be equal in magnitude to the voltage on insulated wire 1823A). Accordingly, a voltage differential can form between insulated wires 1823A and 1823F which may be greater than a voltage differential between any other two wires. If said voltage differential between insulated wires 1823A and 1823F exceeds a threshold sufficient to form a spark, a spark can form between electrodes on insulated wires 1823A and 1823F.

The voltage at which the energy generator 1850 drives the wires 1823A-1823J may correspond to a spark gap distance which may be the same for all emitters. For example, the energy generator 1850 can be programmed with limits to constrain the voltage at which it drives the wires within certain thresholds to avoid causing sparks between unintentional electrodes (e.g., a non-emitter pair of electrodes). Thus, for example, driving insulated wire 1823A and insulated wire 1823C can induce a voltage differential the two wires, however, said voltage differential may only be sufficient to induce a spark at emitter 2E but may not be sufficient to induce a spark between the electrode on wire 1823C in emitter 2E and the electrode on wire 1823A in emitter 3E (which is a non-emitter pair), at least because the distance between those electrodes is greater than the spark gap distance between the electrodes in emitter 2E.

Energy generator 1850 can drive voltage on any of the wires 1823A-1823J to selectively cause a spark to form at any of emitters 1E-35E without causing a spark to form at any of the other emitters. Thus, energy generator 1850 can cause sparks to form one at a time. Energy generator 1850 can drive voltage on wires 1823 in rapid succession to cause sparks to form in rapid succession. For example, energy generator 1850 can cause sparks to form sequentially within microseconds, milliseconds, or centiseconds of each other.

When energy generator 1850 drives one of the wires 1823 with a high voltage and another with a low voltage to form a spark, an electrical current can travel distally away from the generator 1850 down a live wire and can return proximally toward the energy generator 1850 via a return wire. For example, if the energy generator 1850 drives wires 1823A and 1823B high and low respectively, electrical current can travel from energy generator 1850 to emitter 1E via wire 1823A which acts as the live wire. The electrical current can continue to travel from wire 1823A to wire 1823B in the form of a spark that bridges the gap between electrodes in emitter 1E. Electrical current can travel from emitter 1E to energy generator 1850 via wire 1823B which acts as the return wire. Accordingly, any of wires 1823A-1823J can act as either a live wire conducting current from the energy generator 1850 or can act as a return wire conducting energy to the energy generator 1850. Moreover, insulated wires 1823 can alternate between acting as live wire or return wire depending on which of the wires the energy generator 1850 drives with voltage. In some implementations, return wire and ground wire may be used interchangeably.

Although FIG. 18B is not shown to scale, the horizontal distribution of the electrodes may be representative. For example, on insulated wire 1823C, the electrode in emitter 11E may be closer to the electrode in emitter 12E than to the electrode in emitter 6E. Accordingly, the electrodes on insulated wire 1823C are non-uniformly distributed along wire 1823C. This may be the case for one or more of the insulated wires 1823. On wire 1823A, the electrodes may be uniformly distributed from each other along the wire 1823A such that the distance between each of the electrodes on wire 1823A is the same. In some implementations, the wires 1823A-1823J may all be the same length.

Wires 1823A-1823J may be defined by a distal end identified by the emitter that is most distal to the energy generator 1850 (e.g., emitter 1E) and a proximal end identified by the emitter that is the most proximal to the energy generator 1850 (e.g., emitter 35E). For one or more of the wires 1823A-1823J, the distance between the most proximal emitter of that wire and the proximal end of the wires is between 25% to 50%, or at least 50% of the distance between the proximal and distal ends of the wires 1823. This can be seen in at least wires 1823A-1823C where emitters 5E, 10E, and 15E, respectively, are more than half the distance from the proximal end on the right to the distal end on the left. For one or more of the wires 1823A-1823J, the distance between the most distal emitter of that wire and the distal end of the wires is between 25% to 50%, or at least 50% of the distance between the proximal and distal ends of the wires 1823. This can be seen in at least wires 1823I-1823J where emitters 20E and 25E, respectively, are more than half the distance from the distal end on the left to the proximal end on the right. In some implementations, at least half the length of one or more of the wires 1823 may not have any electrodes. For example, at least half the length of insulated wire 1823A has no electrodes between emitter 5E and the proximal end shown on the right toward the energy generator 1850.

The distance from the proximal end demarcated by emitter 35E and the distal end demarcated by emitter 1E may be between 40 mm and 250 mm, between 40 mm and 220 mm, between 40 mm and 150 mm, between 40 mm and 100 mm, between 40 mm and 80 mm, between 60 mm and 220 mm, between 80 mm and 220 mm, between 100 mm and 220 mm, between 100 mm and 200 mm, between 100 mm and 180 mm, between 100 mm and 150 mm, between 150 and 200 mm, or any length therebetween. These example distances may also apply if the wires 1823A-1823J are wrapped around a sheath in an IVL catheter. Thus, an IVL catheter can have 35 emitters spanning 200 mm, for example. Or in other words, an emitter spaced about every 5.7 mm along a longitudinal distance of the IVL catheter.

In FIG. 18B, the bottom three rows beneath the rows of wires 1823 show angular and longitudinal distances between the electrodes and/or emitters of the insulated wires 1823 which are provide as non-limiting examples. $\theta_{En}$ shows the angle between electrodes in a pair. $\theta_{Gn}$ shows the angle between consecutive emitters. In this example, $\theta_{En}+\theta_{Gn}$ equals 120° for each emitter. In some implementations, the sum of $\theta_{En}$ and $\theta_{Gn}$ can vary between one or more emitters. In some implementations, $\theta_{Gn}$ can be the same for each emitter. Zeg shows the longitudinal distance between consecutive emitters. In this example, the longitudinal distance between each emitter is 5.7 mm. These bottom three rows showing angular and longitudinal separation can be provided as instructions when forming the electrodes and/or emitters and can be interpreted from top to bottom and from left to right. For example, at emitter 1E, the electrode can be formed on wire 1823A, then the IVL catheter can be rotated 60° (the $\theta_{E1}$ angle). At this stage of the process in some aspects, the IVL catheter can be longitudinally translated by a distance of Zn as shown and/or described in FIGS. 17A-17B. The other electrode in emitter 1E can then be formed on wire 1823B. After both electrodes of emitter 1E are formed, the IVL catheter can be rotated 60° (the $\theta_{G1}$ angle) and translated longitudinally 5.7 mm to emitter 2E where the electrode on wire 1823A can be formed. This process can continue until all electrodes are formed for all emitters 1E-35E.

Figure 19:
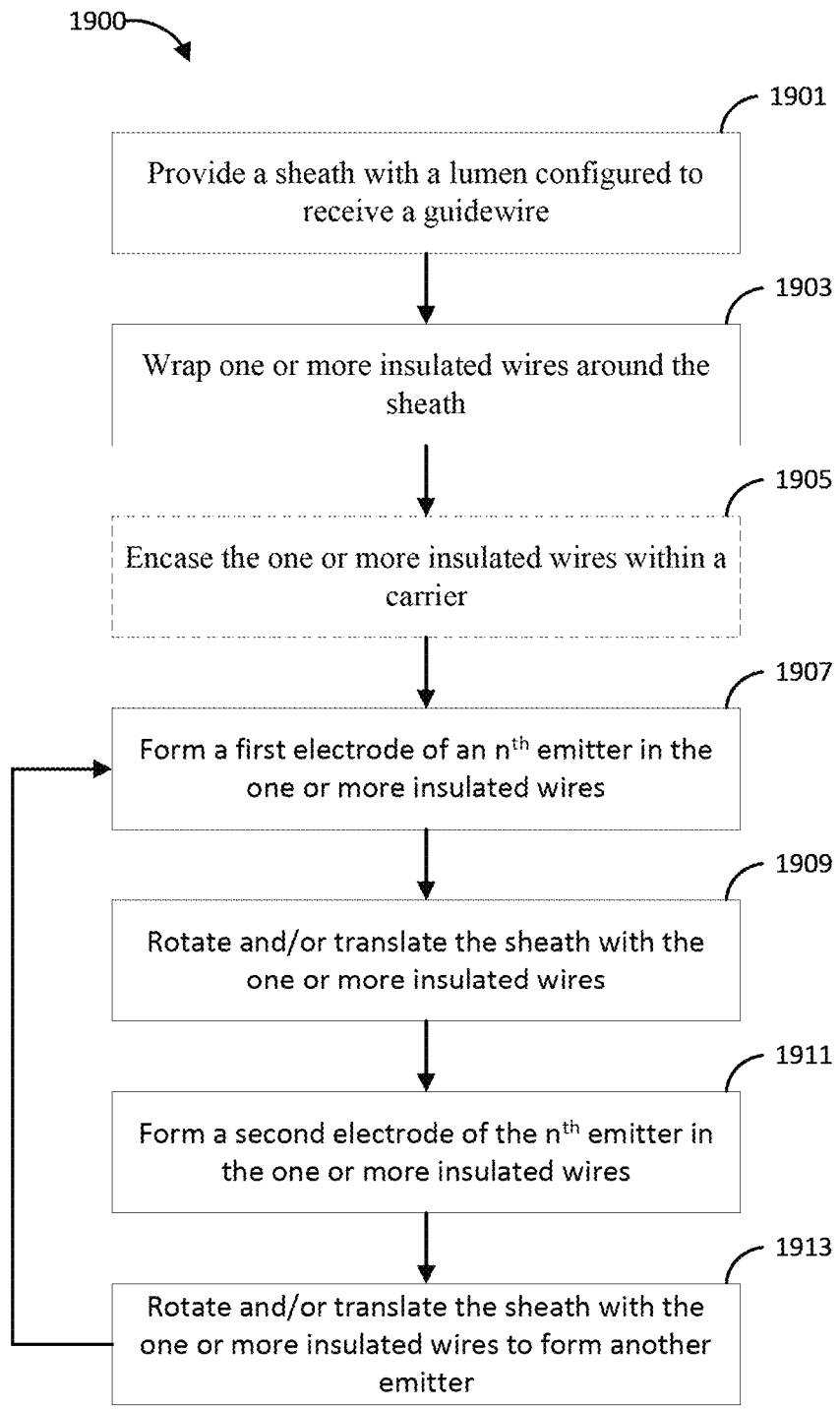
FIG. 19 is a flowchart of an example process of making an IVL catheter or portions thereof.

FIG. 19 is a flowchart of a process of making an IVL catheter, or portions thereof. At block 1901, a sheath can be provided that has a lumen that can received a guidewire therethrough. At block 1903 one or more insulated wires can be wrapped around the sheath. The insulated wires can be helically wrapped with a uniform pitch or with a pitch that varies. At block 1905, the one or more insulated wires can optionally be encased within a carrier that encases the wires and the sheath.

At block 1907, a first electrode of an nth emitter can be formed. Forming an electrode can include forming an insulative member opening within an insulative member of an insulated wire to expose a portion of an electrically conductive member of the insulated wire. In implementations with a carrier, forming an electrode can include forming a carrier opening. The carrier opening can be aligned with the insulative member opening and/or exposed portion of the insulated wire. A laser can form the electrode (e.g., the carrier opening, insulative member opening, and/or exposed portion). For example, the electrode can be formed with a laser etching process that removes portions of the carrier and/or insulative member with optical energy from a laser. In some implementations, the carrier opening can be formed at the same time (e.g., immediately before and/or during a same procedure) as the insulative member opening and/or exposed portion. For example, a laser can form a carrier opening and then can proceed to form the insulative member opening immediately thereafter such as without modifying the energy or position of the laser. Forming the carrier opening and the insulative member openings with the same laser beam can ensure that the carrier opening is aligned with the insulative member opening which can ensure that the exposed portion is exposed through the carrier opening and moreover that each of the exposed portions of the various electrodes have the same amount of surface area that is exposed through the various carrier openings which can ensure consistent energy differentials required to form spark gaps at the various emitters.

At block 1909, the sheath together with the one or more insulated wires wrapped around thereon can be rotated and/or translated. In some implementations, such as when using a laser to form electrodes, the sheath may remain stationary while a laser travels relative to the sheath and/or wires. Rotating can include any of the example $\theta_{En}$ angles shown and/or discussed herein. Translating can include any of the example (n+1) w distances shown and/or discussed herein.

At block 1911, a second electrode of the nth can be formed which may be similar to how the first electrode was formed.

At block 1913, the sheath together with the one or more insulated wires wrapped around thereon can be rotated and/or translated, whether actually moved or an electrode forming device or system is moved relative to it. Rotating can include any of the example $\theta_{EG}$ angles shown and/or discussed herein. Translating can include any of the example Zeg distances shown and/or discussed herein.

The process can continue to iterate through any of blocks 1907-1913 until all of the electrodes and/or emitters have been formed. In some implementations, blocks 1907-1913 can be performed before the wires have been wrapped around the sheath at block 1903 and/or before the carrier encases the insulted wires at block 1905. As such, carrier openings can be formed after exposed portions have been formed in some aspects.

I. Additional Considerations

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the present disclosure. The publications discussed above and throughout the text are provided solely for their disclosure prior to the filing date of the present application. Nothing herein is to be construed as an admission that the inventors are not entitled to antedate any referenced publication by virtue of prior invention.

Although certain implementations and examples have been described herein, it will be understood by those skilled in the art that many aspects of the systems and devices shown and described in the present disclosure may be differently combined and/or modified to form still further implementations or acceptable examples. All such modifications and variations are intended to be included herein within the scope of this disclosure. A wide variety of designs and approaches are possible. No feature, structure, or step disclosed herein is essential or indispensable. The various features and processes described herein may be used independently of one another, or may be combined in various ways. For example, elements may be added to, removed from, or rearranged compared to the disclosed example implementations. All possible combinations and sub-combinations are intended to fall within the scope of this disclosure.

Any methods and processes described herein are not limited to any particular sequence, and the blocks or states relating thereto can be performed in other sequences that are appropriate. For example, described blocks or states may be performed in an order other than that specifically disclosed, or multiple blocks or states may be combined in a single block or state, or certain method or process blocks may be omitted, or certain blocks or states may be performed in a reverse order from what is shown and/or described. The example blocks or states may be performed in serial, in parallel, or in some other manner. Blocks or states may be added to or removed from the disclosed example implementations.

The methods disclosed herein may include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct entities or other users. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames).

Many other variations than those described herein will be apparent from this disclosure. For example, depending on the implementation, certain acts, events, or functions of any of the algorithms described herein can be performed in a different sequence, can be added, merged, or left out altogether (for example, not all described acts or events are necessary for the practice of the algorithms). Moreover, in certain implementations, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

Various illustrative logical blocks, modules, routines, and algorithm steps that may be described in connection with the disclosure herein can be implemented as electronic hardware (e.g., ASICs or FPGA devices), computer software that runs on computer hardware, or combinations of both. Various illustrative components, blocks, and steps may be described herein generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, various illustrative logical blocks and modules that may be described in connection with the implementations disclosed herein can be implemented or performed by a machine, such as a general purpose processor, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A general purpose processor can be a microprocessor, controller, microcontroller, or state machine, combinations of the same, or the like.

A processor can include electrical circuitry configured to process computer-executable instructions. A processor can include an FPGA or other programmable devices that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. For example, some, or all, of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of any method, process, routine, or algorithm described in connection with the disclosure herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain features, elements, and/or steps are optional. Thus, such conditional language is not generally intended to imply that features, elements, and/or steps are in any way required or that one or more embodiments necessarily include logic for deciding, with or without other input or prompting, whether these features, elements, and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 10 degrees, 5 degrees, 3 degrees, or 1 degree. As another example, in certain embodiments, the terms "generally perpendicular" and "substantially perpendicular" refer to a value, amount, or characteristic that departs from exactly perpendicular by less than or equal to 10 degrees, 5 degrees, 3 degrees, or 1 degree.

As used herein, "real-time" or "substantial real-time" may refer to events (e.g., receiving, processing, transmitting, displaying etc.) that occur at a same time as each other, during a same time as each other, or overlap in time with each other. "Real-time" may refer to events that occur at distinct or non-overlapping times the difference between which is imperceptible and/or inconsequential to humans such as delays arising from electrical conduction or transmission. A human may perceive real-time events as occurring simultaneously, regardless of whether the real-time events occur at an exact same time. As a non-limiting example, "real-time" may refer to events that occur within a time frame of each other that is on the order of milliseconds, seconds, tens of seconds, or minutes. For example, "real-time" may refer to events that occur within a time frame of less than 1 minute, less than 30 seconds, less than 10 seconds, less than 1 second, less than 0.05 seconds, less than 0.01 seconds, less than 0.005 seconds, less than 0.001 seconds, etc.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

As used herein, "system," "instrument," "apparatus," and "device" generally encompass both the hardware (for example, mechanical and electronic) and, in some implementations, associated software (for example, specialized computer programs for operational control) components.

It should be emphasized that many variations and modifications may be made to the herein-described implementations, the elements of which are to be understood as being among other acceptable examples. All such modifications and variations are intended to be included herein within the scope of this disclosure. Any section headings used herein are merely provided to enhance readability and are not intended to limit the scope of the implementations disclosed in a particular section to the features or elements disclosed in that section. The foregoing description details certain implementations. It will be appreciated, however, that no matter how detailed the foregoing appears in text, the systems and methods can be practiced in many ways. As is also stated herein, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Those of skill in the art would understand that information, messages, and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

II. Example Clauses

Examples of the implementations of the present disclosure can be described in view of the following example clauses. The features recited in the below example implementations can be combined with additional features disclosed herein. Furthermore, additional inventive combinations of features are disclosed herein, which are not specifically recited in the below example implementations, and which do not include the same features as the specific implementations below. For sake of brevity, the below example implementations do not identify every inventive aspect of this disclosure. The below example implementations are not intended to identify key features or essential features of any subject matter described herein. Any of the example clauses below, or any features of the example clauses, can be combined with any one or more other example clauses, or features of the example clauses or other features of the present disclosure.

Clause 1. An intravascular lithotripsy system configured to modify calcified plaque within a blood vessel of a subject, the system comprising: a sheath comprising a lumen configured to receive a guidewire; a first insulated wire coupled to the sheath and comprising an electrically conductive member, an insulative member encasing the electrically conductive member, a first insulative member opening forming a first exposed portion of the first insulated wire, and a second insulative member opening forming a second exposed portion of the first insulated wire; a second insulated wire coupled to the sheath and comprising an electrically conductive member, an insulative member encasing the electrically conductive member of the second insulated wire, a first insulative member opening forming a first exposed portion of the second insulated wire, and a second insulative member opening forming a second exposed portion of the second insulated wire; a third insulated wire coupled to the sheath and comprising an electrically conductive member, an insulative member encasing the electrically conductive member of the third insulated wire, a first insulative member opening forming a first exposed portion of the third insulated wire, and a second insulative member opening forming a second exposed portion of the third insulated wire, wherein the first insulated wire is helically wound around the sheath, wherein the second insulated wire is helically wound around the sheath adjacent to the first insulated wire, wherein the third insulated wire is helically wound around the sheath, adjacent to the second insulated wire; and an energy generator configured to: induce a first spark between the first exposed portion of the first insulated wire and the first exposed portion of the second insulated wire; induce a second spark between the second exposed portion of the first insulated wire and the first exposed portion of the third insulated wire; and induce a third spark between the second exposed portion of the second insulated wire and the second exposed portion of the third insulated wire, wherein the first insulated wire is directly electrically connected with the energy generator independently from the second and third insulated wires and configured to conduct current between the energy generator and the second exposed portion of the first insulated wire past the first exposed portion of the first insulated wire when forming the second spark without forming the first spark, wherein the second insulated wire is directly electrically connected with the energy generator independently from the first and third insulated wires and configured to conduct current between the energy generator and the second exposed portion of the second insulated wire past the first exposed portion of the second insulated wire when forming the third spark without forming the first spark, wherein the third insulated wire is directly electrically connected with the energy generator independently from the second and second insulated wires and configured to conduct current between the energy generator and the second exposed portion of the third insulated wire past the first exposed portion of the third insulated wire when forming the third spark without forming the second spark.

Clause 2. The intravascular lithotripsy system of Clause 1, wherein the energy generator is configured to conduct current to the first, second, or third insulated wires without a dedicated return wire.

Clause 3. The intravascular lithotripsy system of any of Clauses 1-2, wherein the energy generator is configured to drive voltage on the first, second, and third insulated wires independently to cause the first, second, and third insulated wires to transition between operating at least as a live wire conducting current from the energy generator or as a return wire conducting current to the energy generator.

Clause 4. The intravascular lithotripsy system of any of Clauses 1-3, wherein the energy generator is configured to drive voltage on the first and second insulated wires without driving voltage on the third insulated wire to induce the first spark without inducing the second spark and the third spark.

Clause 5. The intravascular lithotripsy system of any of Clauses 1-4, wherein a first distance between the first exposed portion of the first insulated wire and the first exposed portion of the second insulated wire is less than a second distance between the second exposed portion of the first insulated wire and the first exposed portion of the second insulated wire, wherein the energy generator is configured to induce a voltage differential between the first and second insulated wires within a threshold sufficient to induce the first spark over the first distance and insufficient to induce a fourth spark over the second distance.

Clause 6. The intravascular lithotripsy system of any of Clauses 1-5, wherein a first distance between the first exposed portion of the first insulated wire and the first exposed portion of the second insulated wire is the same as a second distance between the second exposed portion of the second insulated wire and the second exposed portion of the third insulated wire thereby allowing the first and third sparks to form responsive to a same voltage differential caused by the energy generator.

Clause 7. The intravascular lithotripsy system of any of Clauses 1-6, wherein the first exposed portion of the first insulated wire is circumferentially offset from the second exposed portion of the first insulated wire around an outer surface of the sheath.

Clause 8. The intravascular lithotripsy system of any of Clauses 1-7, wherein the first, second, and third insulated wires are a same length.

Clause 9. The intravascular lithotripsy system of any of Clauses 1-8, wherein the second insulated wire extends alongside and contacts the first and third insulated wires.

Clause 10. The intravascular lithotripsy system of any of Clauses 1-9, wherein a distance between the second exposed portion of the first insulated wire and a proximal end of the first insulated wire is at least half a distance between the first exposed portion of the first insulated wire and the proximal end of the first insulated wire.

Clause 11. The intravascular lithotripsy system of any of Clauses 1-10, wherein the first insulated wire comprises a proximal insulative member opening forming a proximal exposed portion of the first insulated wire, wherein a distance between the first and proximal exposed portions of the first insulated wire is less than a distance between the proximal exposed portion and a proximal end of the first insulated wire.

Clause 12. The intravascular lithotripsy system of any of Clauses 1-11, further comprising: a fourth insulated wire coupled to the sheath and comprising an electrically conductive member, an insulative member encasing the electrically conductive member of the fourth insulated wire, and at least three insulative member openings forming at least three exposed portions of the fourth insulated wire; and wherein the first insulated wire comprises a third insulative member opening forming a third exposed portion of the first insulated wire; wherein the energy generator is directly electrically connected with the fourth insulated wire and configured to: induce a fourth spark between the third exposed portion of the first insulated wire and the at least three exposed portions of the fourth insulated wire.

Clause 13. The intravascular lithotripsy system of Clause 12, wherein the first, second, third, and fourth exposed portions of the first insulated wire are uniformly spaced.

Clause 14. The intravascular lithotripsy system of any of Clauses 12-13, wherein the second insulated wire comprises a third insulative member opening forming a third exposed portion of the second insulated wire, wherein the energy generator is configured to: induce a sixth spark between the third exposed portion of the second insulated wire and the at least three exposed portions of the fourth insulated wire.

Clause 15. The intravascular lithotripsy system of Clause 14, wherein the first, second, third, and fourth exposed portions of the second insulated wire are non-uniformly spaced.

Clause 16. The intravascular lithotripsy system of any of Clauses 1-15, further comprising a balloon around at least a portion of the sheath and configured to be expanded with a conductive fluid configured to conduct a sonic wave originating from the spark, wherein the exposed portions of the first and second insulated wires are exposed to the conductive fluid at least when the balloon is expanded, wherein no portion of the balloon contacts the exposed portions of the first and second insulated wires.

Clause 17. The intravascular lithotripsy system of Clause 16, wherein the balloon is coated with medication.

Clause 18. The intravascular lithotripsy system of any of Clauses 1-17, wherein: the first insulated wire is wound around the sheath with a first pitch; and the second insulated wire is wound around the sheath with a second pitch that is substantially equal to the first pitch.

Clause 19. The intravascular lithotripsy system of any of Clauses 1-18, wherein the first insulated wire is wound around the sheath with a uniform pitch along the sheath.

Clause 20. The intravascular lithotripsy system of any of Clauses 1-19, wherein the first insulated wire is wound around the sheath with a variable pitch along the sheath.

Clause 21. The intravascular lithotripsy system of any of Clauses 1-20, wherein the first and second insulated wires are removably electrically connected to the energy generator.

Clause 22. The intravascular lithotripsy system of any of Clauses 1-21, further comprising a carrier encasing the first and second insulated wires and the sheath, the carrier comprising: a first carrier opening aligned with the exposed portion of the electrically conductive member of the first insulated wire; and a second carrier opening spaced from the first carrier opening and aligned with the exposed portion of the electrically conductive member of the second insulated wire.

Clause 23. The intravascular lithotripsy system of Clause 22, wherein the first and second carrier openings are configured such that the exposed portions of the electrically conductive member are not covered by the carrier.

Clause 24. The intravascular lithotripsy system of any of Clauses 1-23, wherein each of the first, second, and third, insulated wires is capable of forming a spark with each of the other insulated wires.

Clause 25. An intravascular lithotripsy system configured to modify calcified plaque within a blood vessel of a subject, the system comprising: a sheath comprising a lumen configured to receive a guidewire; at least three insulated wires, each of the at least three insulated wires comprising at least two exposed portions spaced from one another along a length of the insulated wire, wherein the at least three insulated wires are helically wound around an outer surface of the sheath and independently electrically connected with an energy generator, the exposed portions of the at least three insulated wires defining a plurality of emitters spaced from one another along a length of the sheath and independently operable by the energy generator; and the energy generator configured to induce a spark via each of the plurality of emitters.

Clause 26. The intravascular lithotripsy system of Clause 25, wherein the plurality of emitters comprises: a first emitter defined by a first exposed portion of a first one of the at least three insulated wires and a first exposed portion of a second one of the at least three insulated wires; a second emitter defined by a second exposed portion of the first one of the at least three insulated wires and a first exposed portion of a third one of the at least three insulated wires; and a third emitter defined by a second exposed portion of the second one of the at least three insulated wires and a second exposed portion of the third one of the at least three insulated wires.

Clause 27. The intravascular lithotripsy system of Clause 25, wherein each of the at least three insulated wires is configured to form at least one of the plurality of emitters with each of the other at least three insulated wires.

Clause 28. The intravascular lithotripsy system of Clause 25, wherein the plurality of emitters are formed from the at least three insulated wires without any other insulated wires.

Clause 29. The intravascular lithotripsy system of Clause 25, wherein the at least three insulated wires comprises at least four insulated wires, wherein the plurality of emitters comprises more emitters than the at least four insulated wires.

Clause 30. The intravascular lithotripsy system of Clause 25, wherein the at least three insulated wires does not include a dedicated return wire.

Clause 31. An intravascular lithotripsy catheter for modifying calcified plaque within a blood vessel of a subject, the intravascular lithotripsy catheter comprising:

a sheath comprising a lumen configured to receive a guidewire, wherein a longitudinal axis of the intravascular lithotripsy catheter extends through the lumen; a first insulated wire wound around and contacting an outer surface of the sheath, the first insulated wire comprising an electrically conductive member, an insulative member encasing the electrically conductive member, and an insulative member opening forming an exposed portion of the electrically conductive member; a second insulated wire wound around and contacting the outer surface of the sheath, the second insulated wire arranged adjacent the first insulated wire and comprising an electrically conductive member, an insulative member encasing the electrically conductive member of the second insulated wire, and an insulative member opening forming an exposed portion of the electrically conductive member of the second insulated wire; wherein the exposed portion of the second insulated wire is circumferentially offset from the exposed portion of the first insulated wire by an angle originating at the longitudinal axis; wherein the exposed portion of the second insulated wire is longitudinally offset from the exposed portion of the first insulated wire by a longitudinal distance extending along the intravascular lithotripsy catheter parallel to the longitudinal axis; and a carrier encasing the first and second insulated wires and the sheath, the carrier comprising: a first carrier opening aligned with the exposed portion of the electrically conductive member of the first insulated wire; and a second carrier opening spaced from the first carrier opening and aligned with the exposed portion of the electrically conductive member of the second insulated wire; wherein the intravascular lithotripsy catheter is configured to be electrically connected to an energy generator that is operable to cause a spark to travel longitudinally along the intravascular lithotripsy catheter and circumferentially around the intravascular lithotripsy catheter between the exposed portions of the first and second insulated wires.

Clause 32. The intravascular lithotripsy catheter of Clause 31, wherein the carrier comprises an inner surface configured to contact the first and second insulated wires and an outer surface opposite the inner surface, wherein the intravascular lithotripsy catheter is configured such that the spark travels from the exposed portion of the first insulated wire, through the first carrier opening, above the outer surface of the carrier, through the second carrier opening, and to the exposed portion of the second insulated wire.

Clause 33. The intravascular lithotripsy catheter of any of Clauses 31-32, wherein the carrier has a fixed volume.

Clause 34. The intravascular lithotripsy catheter of any of Clauses 31-33, wherein the carrier comprises a different material than at least one of the electrically conductive members of the insulated wires or the sheath.

Clause 35. The intravascular lithotripsy catheter of any of Clauses 31-34, wherein the first and second carrier openings are configured such that the exposed portions of the electrically conductive member are not covered by the carrier.

Clause 36. The intravascular lithotripsy catheter of any of Clauses 31-35, further comprising a balloon configured to hold conductive fluid around at least a portion of the sheath, wherein the carrier inhibits the balloon from contacting the exposed portions of the electrically conductive members of the first and second insulated wires, wherein the exposed portions of the electrically conductive members of the first and second insulated wires are exposed to the conductive fluid.

Clause 37. The intravascular lithotripsy catheter of Clause 36, wherein the carrier is configured to separate the balloon from the exposed portions of the electrically conductive members of the first and second insulated wires.

Clause 38. The intravascular lithotripsy catheter of Clause 36, wherein the balloon is coated with medication.

Clause 39. The intravascular lithotripsy catheter of any of Clauses 31-38, wherein: the first insulated wire is wound around the outer surface of the sheath with a first pitch; and the second insulated wire is wound around the outer surface of the sheath with a second pitch that is substantially equal to the first pitch.

Clause 40. The intravascular lithotripsy catheter of any of Clauses 31-39, wherein the first insulated wire is wound around the outer surface of the sheath with a uniform pitch along the sheath.

Clause 41. The intravascular lithotripsy catheter of any of Clauses 31-40, wherein the first insulated wire is wound around the outer surface of the sheath with a variable pitch along the sheath.

Clause 42. The intravascular lithotripsy catheter of any of Clauses 31-41, further comprising an energy generator configured to: induce an energy differential between (i) the exposed portion of the electrically conductive member of the first insulated wire and (ii) the exposed portion of the electrically conductive member of the second insulated wire to induce the spark between the exposed portions of the electrically conductive members of the first and second insulated wires.

Clause 43. The intravascular lithotripsy catheter of Clause 42, wherein the first and second insulated wires are removably electrically connected to the energy generator.

Clause 44. An intravascular lithotripsy catheter for modifying calcified plaque within a blood vessel of a subject, the intravascular lithotripsy catheter comprising: a sheath comprising a lumen configured to receive a guidewire; a first insulated wire comprising an electrically conductive member, an insulative member encasing the electrically conductive member, and an insulative member opening forming an exposed portion of the electrically conductive member; a second insulated wire arranged adjacent the first insulated wire and comprising an electrically conductive member, an insulative member encasing the electrically conductive member of the second insulated wire, and an insulative member opening forming an exposed portion of the electrically conductive member of the second insulated wire; and a longitudinal axis extending through the sheath; wherein the first and second insulated wires are wrapped around the sheath such that: the exposed portion of the second insulated wire is arranged at a different longitudinal location than the exposed portion of the first insulated wire relative to said longitudinal axis relative to said longitudinal axis; the exposed portion of the second insulated wire is arranged at a different angular location than the exposed portion of the first insulated wire relative to a plane defined normal to said longitudinal axis.

Clause 45. The intravascular lithotripsy catheter of Clause 44, wherein the first and second insulated wires are configured to be electrically connected to an energy generator that is operable to cause a spark to travel: longitudinally along the intravascular lithotripsy catheter from the exposed portion of the first insulated wire to the exposed portion of the second insulated wire; and circumferentially around the intravascular lithotripsy catheter from the exposed portion of the first insulated wire to the exposed portion of the second insulated wire.

Clause 46. The intravascular lithotripsy catheter of any of Clauses 44-45, wherein: the first insulated wire is wound around the sheath with a first pitch; and the second insulated wire is wound around the sheath with a second pitch that is substantially equal to the first pitch.

Clause 47. An intravascular lithotripsy catheter for modifying calcified plaque within a blood vessel of a subject, the intravascular lithotripsy catheter comprising: a sheath comprising a lumen configured to receive a guidewire; a first insulated wire comprising an electrically conductive member, an insulative member encasing the electrically conductive member, and an insulative member opening forming an exposed portion of the electrically conductive member; a second insulated wire comprising an electrically conductive member, an insulative member encasing the electrically conductive member of the second insulated wire, and an insulative member opening forming an exposed portion of the electrically conductive member of the second insulated wire; and a longitudinal axis extending through the sheath; wherein the first and second insulated wires are wrapped around the sheath such that: a transverse cross-section through the intravascular lithotripsy catheter that is perpendicular to said longitudinal axis passes through the exposed portion of the first insulated wire without passing through the exposed portion of the second insulated wire; and a longitudinal cross-section through the intravascular lithotripsy catheter that is parallel to said longitudinal axis passes through the exposed portion of the first insulated wire without passing through the exposed portion of the second insulated wire.

Clause 48. The intravascular lithotripsy catheter of Clause 47, wherein the first and second insulated wires are configured to be electrically connected to an energy generator that is operable to cause a spark to travel: longitudinally along the intravascular lithotripsy catheter from the exposed portion of the first insulated wire to the exposed portion of the second insulated wire; and circumferentially around the intravascular lithotripsy catheter from the exposed portion of the first insulated wire to the exposed portion of the second insulated wire.

Clause 49. The intravascular lithotripsy catheter of any of Clauses 47-48, wherein: the first insulated wire is wound around the sheath with a first pitch; and the second insulated wire is wound around the sheath with a second pitch that is substantially equal to the first pitch.

Clause 50. An intravascular lithotripsy system configured to modify calcified plaque within a blood vessel of a subject, the system comprising: a sheath comprising a lumen configured to receive a guidewire; a first insulated wire helically wound around and contacting an outer surface of the sheath, the first insulated wire comprising an electrically conductive member, an insulative member encasing the electrically conductive member, and an insulative member opening forming an exposed portion of the first insulated wire; a second insulated wire helically wound around and contacting the outer surface of the sheath, the second insulate wire arranged adjacent to, and in contact with, the first insulated wire and comprising an electrically conductive member, an insulative member encasing the electrically conductive member of the second insulated wire, and an insulative member opening forming an exposed portion of the second insulated wire, wherein the second insulated wire is helically wound parallel to the first insulated wire; and an energy generator electrically connected with the first and second insulated wires and configured to: induce a voltage differential between (i) the exposed portion of the first insulated wire and (ii) the exposed portion of the second insulated wire; and cause said voltage differential to exceed a threshold to induce a spark between the exposed portions of the first and second insulated wires.

Clause 51. The system of Clause 50, wherein: said energy differential is a first energy differential; said insulative member opening of the first insulated wire is a first insulative member opening of the first insulated wire and said exposed portion of the first insulated wire is a first exposed portion of the first insulated wire; said first insulated wire further comprises a second insulative member opening forming a second exposed portion of the first insulated wire; the system further comprises a third insulated wire helically wound around and contacting the outer surface of the sheath, the third insulated wire arranged adjacent one of the first or second insulated wires and comprising an electrically conductive member, an insulative member encasing the electrically conductive member of the third insulated wire, and an insulative member opening forming an exposed portion of the electrically conductive member of the third insulated wire; and the energy generator is electrically connected with the third insulated wire and further configured to: induce a second voltage differential between (i) the second exposed portion of the first insulated wire and (ii) the exposed portion of the third insulated wire; and cause said second energy differential to exceed the energy threshold to induce a spark between the second exposed portion of the first insulated wire and the exposed portion of the third insulated wire.

Clause 52. The system of Clause 51, wherein the first voltage differential is the same amount of energy as the second voltage differential.

Clause 53. The system of any of Clauses 51-52, wherein each of the first, second, and third insulated wires are independently electrically connected to the energy generator.

Clause 54. The system of any of Clauses 51-53, wherein the sheath comprises a length; and the first and second exposed portions of the first insulated wire and the exposed portions of the second and third insulated wires are arranged such that: the spark induced between the first exposed portion of the first insulated wire and the exposed portion of the second insulated wire is induced at a first location along the length of the sheath; the spark induced between the second exposed portion of the first insulated wire and the exposed portion of the third insulated wire is induced at a second location along the length of the sheath; and the second location is spaced from the first location.

Clause 55. The system of any of Clauses 51-54, wherein the system is configured to cause said first energy differential between (i) the first exposed portion of the first insulated wire and (ii) the exposed portion of the second insulated wire without causing said second energy differential between (i) the second exposed portion of the first insulated wire and (ii) the exposed portion of the third insulated wire.

Clause 56. The system of any of Clauses 51-55, wherein: said insulative member opening of the second insulated wire is a first insulative member opening of the second insulated wire and said exposed portion of the second insulated wire is a first exposed portion of the second insulated wire; said second insulated wire further comprises a second insulative member opening forming a second exposed portion of the second insulated wire; said insulative member opening of the third insulated wire is a first insulative member opening of the third insulated wire and said exposed portion of the third insulated wire is a first exposed portion of the third insulated wire; said third insulated wire further comprises a second insulative member opening forming a second exposed portion of the third insulated wire; the energy generator is further configured to: induce the third voltage differential between (i) the second exposed portion of the second insulated wire and (ii) the second exposed portion of the third insulated wire; and cause said third energy differential to exceed the energy threshold to induce a spark between the second exposed portion of the second insulated wire and the second exposed portion of the third insulated wire.

Clause 57. The system of any of Clauses 50-56, further comprising a balloon around at least a portion of the sheath and configured to be expanded with a conductive fluid configured to conduct a sonic wave originating from the spark, wherein the exposed portions of the first and second insulated wires are exposed to the conductive fluid at least when the balloon is expanded, wherein no portion of the balloon contacts the exposed portions of the first and second insulated wires.

Clause 58. The system of any of Clauses 50-57, wherein: the first insulated wire is wound around the outer surface of the sheath with a first pitch; and the second insulated wire is wound around the outer surface of the sheath with a second pitch that is substantially equal to the first pitch.

Clause 59. The system of any of Clauses 50-58, wherein the first insulated wire is wound around the outer surface of the sheath with a uniform pitch along the sheath.

Clause 60. The system of any of Clauses 50-59, wherein the first insulated wire is wound around the outer surface of the sheath with a variable pitch along the sheath.

Clause 61. The system of any of Clauses 50-60, wherein the first and second insulated wires are removably electrically connected to the energy generator.

Clause 62. The system of any of Clauses 50-61, further comprising a carrier encasing the first and second insulated wires and the sheath, the carrier comprising: a first carrier opening aligned with the exposed portion of the electrically conductive member of the first insulated wire; and a second carrier opening spaced from the first carrier opening and aligned with the exposed portion of the electrically conductive member of the second insulated wire.

Clause 63. The system of Clause 62, wherein the first and second carrier openings are configured such that the exposed portions of the electrically conductive member are not covered by the carrier.

Clause 64. An intravascular lithotripsy system configured to modify calcified plaque within a blood vessel of a subject, the system comprising: a sheath comprising a lumen configured to receive a guidewire; a first insulated wire wound around and contacting an outer surface of the sheath, the first insulated wire comprising an electrically conductive member, an insulative member encasing the electrically conductive member, and an insulative member opening forming an exposed portion of the first insulated wire; a second insulated wire wound around and contacting the outer surface of the sheath, the second insulate wire arranged adjacent the first insulated wire and comprising an electrically conductive member, an insulative member encasing the electrically conductive member of the second insulated wire, and an insulative member opening forming an exposed portion of the second insulated wire; and an energy generator electrically connected with the first and second insulated wires and configured to induce a spark between the exposed portions of the first and second insulated wires.

Clause 65. The system of Clause 64, further comprising a balloon around at least a portion of the sheath and configured to be expanded with a conductive fluid configured to conduct a sonic wave originating from the spark.

Clause 66. The system of Clause 65, wherein the balloon is configured to be transitioned between an expanded state and a non-expanded state, and wherein the exposed portions of the first and second insulated wires are exposed to the conductive fluid at least when the balloon is in the expanded state.

Clause 67. The system of any of Clauses 65-66, wherein the balloon is configured to be transitioned between an expanded state and a non-expanded state, and wherein the exposed portions of the first and second insulated wires are exposed to the conductive fluid when the balloon is in the expanded state and when the balloon is in the non-expanded state.

Clause 68. The system of any of Clauses 65-67, wherein the system is configured such that no portion of the balloon contacts the exposed portions of the first and second insulated wires.

Clause 69. The system of any of Clauses 65-68, wherein the balloon is configured to be transitioned between an expanded state and a non-expanded state, and wherein the system is configured such that: no portion of the balloon contacts the exposed portions of the first and second insulated wires when the balloon is in the expanded state; and no portion of the balloon contacts the exposed portions of the first and second insulated wires when the balloon is in the non-expanded state.

Clause 70. The system of any of Clauses 64-69, wherein: the first insulated wire is wound around the outer surface of the sheath with a first pitch; and the second insulated wire is wound around the outer surface of the sheath with a second pitch that is substantially equal to the first pitch.

Clause 71. The system of any of Clauses 64-70, wherein the first insulated wire is wound around the outer surface of the sheath with a uniform pitch along the sheath.

Clause 72. The system of any of Clauses 64-71, wherein the first insulated wire is wound around the outer surface of the sheath with a variable pitch along the sheath.

Clause 73. The system of any of Clauses 64-72, wherein the first and second insulated wires are independently electrically connected to the energy generator.

Clause 74. The system of any of Clauses 64-73, wherein the first and second insulated wires are removably electrically connected to the energy generator.

Clause 75. The system of any of Clauses 64-74, further comprising a carrier encasing the first and second insulated wires and the sheath, the carrier comprising: a first carrier opening aligned with the exposed portion of the electrically conductive member of the first insulated wire; and a second carrier opening spaced from the first carrier opening and aligned with the exposed portion of the electrically conductive member of the second insulated wire.

Clause 76. The system of Clause 75, wherein the first and second carrier openings are configured such that the exposed portions of the electrically conductive member are not covered by the carrier.

Clause 77. The system of any of Clauses 64-76, wherein: the sheath comprises a sheath length; the first insulated wire comprises a first length; the second insulated wire comprises a second length; each of the first and second lengths are greater than the sheath length.

Clause 78. A method of manufacturing an intravascular lithotripsy catheter, comprising: providing a sheath comprising a lumen configured to receive a guidewire; helically winding a first insulated wire around the sheath, the first insulated wire comprising an electrically conductive member, an insulative member encasing the electrically conductive member; helically winding a second insulated wire around the sheath, the second insulated wire comprising an electrically conductive member, an insulative member encasing the electrically conductive member of the second insulated wire; and forming an insulative member opening in the first insulated wire to form an exposed portion of the first insulated wire; forming an insulative member opening in the second insulated wire to form an exposed portion of the second insulated wire to allow a spark to form between the exposed portions of the first and second insulated wires.

Clause 79. The method of Clause 78, further comprising forming the insulative member openings in the first and second insulated wires with a laser.

Clause 80. The method of any of Clauses 78-79, further comprising helically winding the second insulated wire adjacent to the first insulated wire.

Clause 81. The method of any of Clauses 78-80, further comprising: helically winding the first insulated wire around the sheath with a first pitch; and helically winding the second insulated wire around the sheath with a second pitch, wherein the first pitch and the second pitch are the same.

Clause 82. The method of any of Clauses 78-81, further comprising helically winding the first insulated wire around the sheath with a uniform pitch.

Clause 83. The method of any of Clauses 78-82, further comprising helically winding the first insulated wire around the sheath with a variable pitch.

Clause 84. The method of any of Clauses 78-83, further comprising helically winding the first insulated wire around the sheath before forming the insulative member opening in the first insulated wire.

Clause 85. The method of any of Clauses 78-84, further comprising forming the insulative member opening in the first insulated wire before helically winding the first insulated wire around the sheath.

Clause 86. The method of any of Clauses 78-85, further comprising providing a carrier encasing the first and second insulated wires and the sheath.

Clause 87. The method of Clause 86, further comprising: forming a first carrier opening aligned with the exposed portion of the electrically conductive member of the first insulated wire; and forming a second carrier opening spaced from the first carrier opening and aligned with the exposed portion of the electrically conductive member of the second insulated wire.

Clause 88. The method of Clause 87, further comprising: forming the first carrier opening when forming the exposed portion of the electrically conductive member of the first insulated wire; and forming the second carrier opening when forming the exposed portion of the electrically conductive member of the second insulated wire.

Clause 89. The method of any of Clauses 87-88, further comprising forming the first and second carrier openings with a laser.

What is claimed is:

1. An intravascular lithotripsy catheter for modifying calcified plaque within a blood vessel of a subject, the intravascular lithotripsy catheter comprising:
    a sheath comprising a lumen configured to receive a guidewire, wherein a longitudinal axis of the intravascular lithotripsy catheter extends through the lumen;
    a first insulated wire wound around and contacting an outer surface of the sheath, the first insulated wire comprising an electrically conductive member, an insulative member encasing the electrically conductive member, and an insulative member opening forming an exposed portion of the electrically conductive member;
    a second insulated wire wound around and contacting the outer surface of the sheath, the second insulated wire comprising an electrically conductive member, an insulative member encasing the electrically conductive member of the second insulated wire, and an insulative member opening forming an exposed portion of the electrically conductive member of the second insulated wire;
    wherein the exposed portion of the second insulated wire is circumferentially offset from the exposed portion of the first insulated wire by an angle originating at the longitudinal axis;
    wherein the exposed portion of the second insulated wire is longitudinally offset from the exposed portion of the first insulated wire by a longitudinal distance extending along the intravascular lithotripsy catheter parallel to the longitudinal axis, wherein the second insulated wire is arranged in contact with the first insulated wire along the longitudinal distance between the exposed portion of the second insulated wire and the exposed portion of the first insulated wire; and
    a carrier encasing the first and second insulated wires and the sheath, the carrier comprising:
        a first carrier opening aligned with the exposed portion of the electrically conductive member of the first insulated wire; and
        a second carrier opening spaced from the first carrier opening and aligned with the exposed portion of the electrically conductive member of the second insulated wire;
        wherein the intravascular lithotripsy catheter is configured to be electrically connected to an energy generator that is operable to cause a spark to form longitudinally along the intravascular lithotripsy catheter and circumferentially around the intravascular lithotripsy catheter from the exposed portion of the first insulated wire to the exposed portion of the second insulated wire.

2. The intravascular lithotripsy catheter of claim 1, wherein the carrier comprises an inner surface configured to contact the first and second insulated wires and an outer surface opposite the inner surface, wherein the intravascular lithotripsy catheter is configured such that the spark travels from the exposed portion of the first insulated wire, through the first carrier opening, above the outer surface of the carrier, through the second carrier opening, and to the exposed portion of the second insulated wire.

3. The intravascular lithotripsy catheter of claim 1, wherein the carrier has a fixed volume.

4. The intravascular lithotripsy catheter of claim 1, wherein the carrier comprises a different material than at least one of the electrically conductive members of the first and second insulated wires or the sheath.

5. The intravascular lithotripsy catheter of claim 1, wherein the first and second carrier openings are configured such that the exposed portions of the electrically conductive members of the first and second insulated wires are not covered by the carrier.

6. The intravascular lithotripsy catheter of claim 1, further comprising a balloon configured to hold conductive fluid around at least a portion of the sheath, wherein the carrier inhibits the balloon from contacting the exposed portions of the electrically conductive members of the first and second insulated wires, wherein the exposed portions of the electrically conductive members of the first and second insulated wires are exposed to the conductive fluid.

7. The intravascular lithotripsy catheter of claim 6, wherein the carrier is configured to separate the balloon from the exposed portions of the electrically conductive members of the first and second insulated wires.

8. The intravascular lithotripsy catheter of claim 6, wherein the balloon is coated with medication.

9. The intravascular lithotripsy catheter of claim 1, wherein:
    the first insulated wire is wound around the outer surface of the sheath with a first pitch; and
    the second insulated wire is wound around the outer surface of the sheath with a second pitch that is substantially equal to the first pitch.

10. The intravascular lithotripsy catheter of claim 1, wherein the first insulated wire is wound around the outer surface of the sheath with a uniform pitch along the sheath.

11. The intravascular lithotripsy catheter of claim 1, wherein the first insulated wire is wound around the outer surface of the sheath with a variable pitch along the sheath.

12. The intravascular lithotripsy catheter of claim 1, wherein the first and second insulated wires are removably electrically connected to the energy generator.

13. The intravascular lithotripsy catheter of claim 1, wherein the energy generator is operable to selectively drive voltage on the first insulated wire independently of the second insulated wire to cause the first insulated wire to transition between operating as a live wire and operating as a return wire.

14. An intravascular lithotripsy catheter for modifying calcified plaque within a blood vessel of a subject, the intravascular lithotripsy catheter comprising:
- a sheath comprising a lumen configured to receive a guidewire;
- a first insulated wire comprising an electrically conductive member, an insulative member encasing the electrically conductive member, and an insulative member opening forming an exposed portion of the electrically conductive member;
- a second insulated wire comprising an electrically conductive member, an insulative member encasing the electrically conductive member of the second insulated wire, and an insulative member opening forming an exposed portion of the electrically conductive member of the second insulated wire;
- a carrier encasing the first and second insulated wires and the sheath, the carrier comprising:
  - a first carrier opening aligned with the exposed portion of the electrically conductive member of the first insulated wire; and
  - a second carrier opening spaced from the first carrier opening and aligned with the exposed portion of the electrically conductive member of the second insulated wire; and
- a longitudinal axis extending through the sheath;
- wherein the first and second insulated wires are wrapped around the sheath such that:
  - the exposed portion of the second insulated wire is arranged at a different longitudinal location than the exposed portion of the first insulated wire relative to said longitudinal axis;
  - the exposed portion of the second insulated wire is arranged at a different angular location than the exposed portion of the first insulated wire relative to a plane defined normal to said longitudinal axis; and
  - the second insulated wire contacts the first insulated wire between a longitudinal location of the exposed portion of the first insulated wire and a longitudinal location of the exposed portion of the second insulated wire;
- wherein the first and second insulated wires are configured to be electrically connected to an energy generator that is operable to cause a spark to form from the exposed portion of the first insulated wire to the exposed portion of the second insulated wire.

15. The intravascular lithotripsy catheter of claim 14, wherein the spark forms:
- longitudinally along the intravascular lithotripsy catheter from the exposed portion of the first insulated wire to the exposed portion of the second insulated wire; and
- circumferentially around the intravascular lithotripsy catheter from the exposed portion of the first insulated wire to the exposed portion of the second insulated wire.

16. The intravascular lithotripsy catheter of claim 14, wherein:
- the first insulated wire is wound around the sheath with a first pitch; and
- the second insulated wire is wound around the sheath with a second pitch that is substantially equal to the first pitch.

17. The intravascular lithotripsy catheter of claim 14, wherein the first insulated wire is wound around the sheath with a uniform pitch along the sheath.

18. An intravascular lithotripsy catheter for modifying calcified plaque within a blood vessel of a subject, the intravascular lithotripsy catheter comprising:
- a sheath comprising a lumen configured to receive a guidewire;
- a first insulated wire comprising an electrically conductive member, an insulative member encasing the electrically conductive member, and an insulative member opening forming an exposed portion of the electrically conductive member;
- a second insulated wire comprising an electrically conductive member, an insulative member encasing the electrically conductive member of the second insulated wire, and an insulative member opening forming an exposed portion of the electrically conductive member of the second insulated wire;
- a carrier encasing the first and second insulated wires and the sheath, the carrier comprising:
  - a first carrier opening aligned with the exposed portion of the electrically conductive member of the first insulated wire; and
  - a second carrier opening spaced from the first carrier opening and aligned with the exposed portion of the electrically conductive member of the second insulated wire; and
- a longitudinal axis extending through the sheath;
- wherein the first and second insulated wires are wrapped around the sheath such that:
  - a transverse cross-section through the intravascular lithotripsy catheter that is perpendicular to said longitudinal axis passes through the exposed portion of the first insulated wire without passing through the exposed portion of the second insulated wire;
  - a longitudinal cross-section through the intravascular lithotripsy catheter that is parallel to said longitudinal axis passes through the exposed portion of the first insulated wire without passing through the exposed portion of the second insulated wire; and
  - the second insulated wire contacts the first insulated wire between the transverse cross-section and the exposed portion of the second insulated wire;
- wherein the first and second insulated wires are configured to be electrically connected to an energy generator that is operable to cause a spark to form from the exposed portion of the first insulated wire to the exposed portion of the second insulated wire.

19. The intravascular lithotripsy catheter of claim 18, wherein the spark forms:
- longitudinally along the intravascular lithotripsy catheter from the exposed portion of the first insulated wire to the exposed portion of the second insulated wire; and
- circumferentially around the intravascular lithotripsy catheter from the exposed portion of the first insulated wire to the exposed portion of the second insulated wire.

20. The intravascular lithotripsy catheter of claim 18, wherein:
- the first insulated wire is wound around the sheath with a first pitch; and
- the second insulated wire is wound around the sheath with a second pitch that is substantially equal to the first pitch.

\* \* \* \* \*